(12) United States Patent
Masuyama et al.

(10) Patent No.: US 10,781,198 B2
(45) Date of Patent: Sep. 22, 2020

(54) COMPOUND, RESIN, PHOTORESIST COMPOSITION AND PROCESS FOR PRODUCING PHOTORESIST PATTERN

(71) Applicant: SUMITOMO CHEMICAL COMPANY, LIMITED, Tokyo (JP)

(72) Inventors: Tatsuro Masuyama, Osaka (JP); Hiromu Nakamura, Osaka (JP); Koji Ichikawa, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 279 days.

(21) Appl. No.: 16/003,497

(22) Filed: Jun. 8, 2018

(65) Prior Publication Data
US 2018/0354927 A1 Dec. 13, 2018

(30) Foreign Application Priority Data
Jun. 13, 2017 (JP) .................................. 2017-115708

(51) Int. Cl.
| | | |
|---|---|---|
| *G03F 7/039* | (2006.01) | |
| *C07D 313/10* | (2006.01) | |
| *C08F 220/68* | (2006.01) | |
| *G03F 7/004* | (2006.01) | |
| *G03F 7/30* | (2006.01) | |
| *G03F 7/16* | (2006.01) | |
| *G03F 7/20* | (2006.01) | |
| *G03F 7/38* | (2006.01) | |

(52) U.S. Cl.
CPC .......... *C07D 313/10* (2013.01); *C08F 220/68* (2013.01); *G03F 7/0045* (2013.01); *G03F 7/0046* (2013.01); *G03F 7/039* (2013.01); *G03F 7/0397* (2013.01); *G03F 7/16* (2013.01); *G03F 7/20* (2013.01); *G03F 7/30* (2013.01); *G03F 7/38* (2013.01)

(58) Field of Classification Search
CPC ..... C07D 313/10; C08F 220/68; G03F 7/039; G03F 7/0397; G03F 7/0382
USPC ...................................................... 430/270.1
See application file for complete search history.

(56) References Cited

U.S. PATENT DOCUMENTS

| | | | | |
|---|---|---|---|---|
| 2006/0003254 A1* | 1/2006 | Saito | ...................... | G03F 7/0397 430/270.1 |
| 2013/0022914 A1* | 1/2013 | Tanaka | .................... | G03F 7/322 430/270.1 |
| 2013/0143157 A1* | 6/2013 | Tanaka | .................. | C08F 220/28 430/270.1 |
| 2016/0077432 A1* | 3/2016 | Shimada | ............... | C08F 222/18 430/270.1 |
| 2016/0168115 A1 | 6/2016 | Miyagawa et al. | | |

FOREIGN PATENT DOCUMENTS

| | | | |
|---|---|---|---|
| JP | 2012-073398 A | * | 4/2012 |
| JP | 2013-122041 A | | 6/2013 |
| JP | 2016-206459 A | * | 12/2016 |
| WO | WO 2012/153869 A1 | | 11/2012 |

OTHER PUBLICATIONS

Belgian Search Report dated Oct. 8, 2018 for corresponding Belgian Application No. 201805385.
Belgian Written Opinion dated Oct. 8, 2018, for corresponding Belgian Application No. 201805385.

* cited by examiner

*Primary Examiner* — John A McPherson
(74) *Attorney, Agent, or Firm* — Birch, Stewart, Kolasch & Birch, LLP

(57) ABSTRACT

A compound represented by the formula (I):

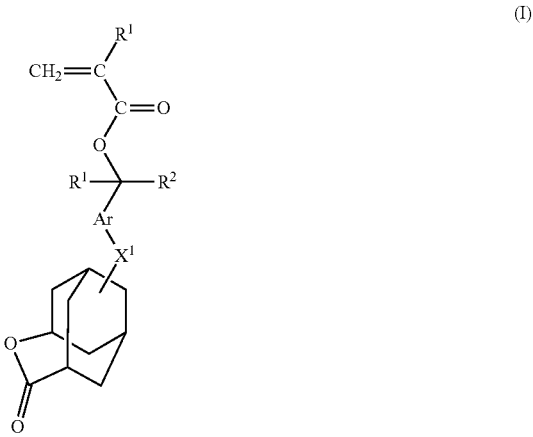

wherein the values of $R^1$, $R^2$, $R^3$, Ar and $X^1$ in formula (I) are defined in the specification.

11 Claims, No Drawings

COMPOUND, RESIN, PHOTORESIST COMPOSITION AND PROCESS FOR PRODUCING PHOTORESIST PATTERN

This nonprovisional application claims priority under 35 U.S.C. § 119(a) on Patent Application No. 2017-115708 filed in JAPAN on Jun. 13, 2017, the entire contents of which are hereby incorporated by reference.

FIELD OF THE INVENTION

The present invention relates to a compound, a resin, a photoresist composition and a process for producing a photoresist pattern.

BACKGROUND OF THE INVENTION

JP2013-122041A1 mentions the following compounds and a composition which comprises a resin having a structural unit derived from one of the compounds.

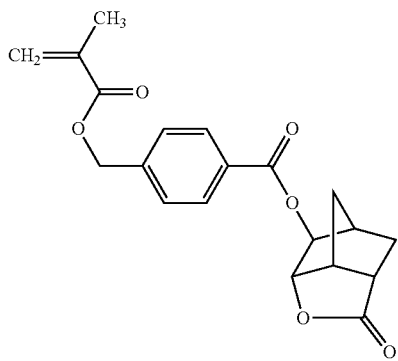

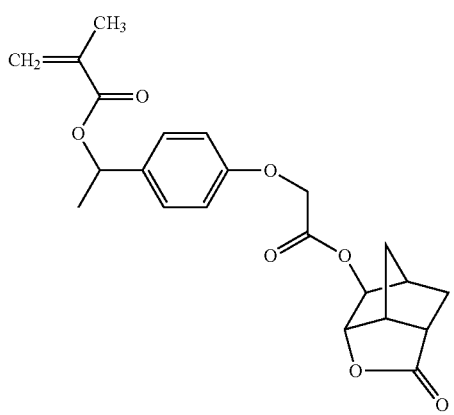

SUMMARY OF THE INVENTION

The present invention relates to the followings:
<1> A compound represented by the formula (I):

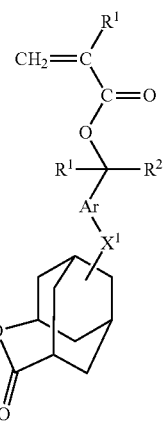

wherein $R^1$ represents a hydrogen atom or a methyl group,
$R^2$ represents a C1-C6 saturated hydrocarbon group,
$R^3$ represents a hydrogen atom or a C1-C6 saturated hydrocarbon group,
Ar represents a C6-C36 aromatic hydrocarbon group in which a hydrogen atom can be replaced by a substituent, and
$X^1$ represents a divalent group which has —CO—O—, —O—CO—, —O—CO—O— or —O—.
<2> The compound according to <1> wherein $R^3$ represents a hydrogen atom.
<3> The compound according to <2> wherein $R^2$ represents a C1-C6 alkyl group.
<4> The compound according to any one of <1> to <3> wherein $X^1$ represents *—$X^{11}$-$A^{11}$-$X^{12}$— or *—$X^{18}$— where $A^{11}$ represents a C1-C6 alkanediyl group, $X^{11}$, $X^{12}$ and $X^{18}$ each independently represents —CO—O—, —O—CO—, —O—CO—O— or —O—, and* represents a binding position to Ar.
<5> A resin comprising a structural unit derived from the compound according to any one of <1> to <4>.
<6> The resin according to <5>, further comprising a structural unit which comprises an acid-labile group and being different from the structural unit derived from the compound represented by the formula (I).
<7> A photoresist composition comprising the resin according to <5> or <6> and an acid generator.
<8> The photoresist composition according to <7> in which an acid generator comprises a salt represented by the formula (B1):

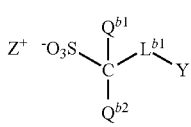

in which $Q^{b1}$ and $Q^{b2}$ independently each represent a fluorine atom or a C1-C6 perfluoroalkyl group,
$L^{b1}$ represents a C1-C24 divalent saturated hydrocarbon group in which a methylene group can be replaced by —CO— or —O— and in which a hydrogen atom can be replaced by a fluorine atom or a hydroxyl group, Y represents a methyl group in which a hydrogen atom can be replaced by a substituent or a C3-C18 alicyclic hydrocarbon group in which a hydrogen atom can be replaced by a substituent and in which a methylene group has been replaced by —O—, —S(O)$_2$— or —CO—, and $Z^+$ represents an organic cation.

<9> The photoresist composition according to <7> or <8> which further comprises a salt generating an acid weaker in acidity than an acid generated from the acid generator.

<10> The photoresist composition according to any one of <7> to <9> which further comprises another resin than the resin recited in <7>, said another resin comprising a structural unit which has a fluorine atom.

<11> A process for producing a photoresist pattern comprising the following steps (1) to (5):
(1) a step of applying the photoresist composition according to any one of <7> to <10> on a substrate,
(2) a step of forming a composition film by conducting drying,
(3) a step of exposing the composition film to radiation,
(4) a step of baking the exposed composition film, and
(5) a step of developing the baked composition film, thereby forming a photoresist pattern.

DESCRIPTION OF EMBODIMENTS

<Compound (I)>

The compound of the disclosure is represented by the formula (I) Hereinafter, the compound is sometimes referred to as "Compound (I)".

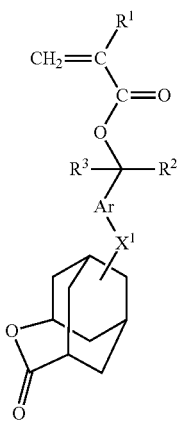

(I)

In the formula, $R^1$ represents a hydrogen atom or a methyl group, $R^2$ represents a C1-C6 saturated hydrocarbon group, $R^3$ represents a hydrogen atom or a C1-C6 saturated hydrocarbon group, Ar represents a C6-C36 aromatic hydrocarbon group in which a hydrogen atom can be replaced by a substituent, and $X^1$ represents a divalent group which has —CO—O—, —O—CO—, —O—CO—O— or —O—.

For $R^2$ and $R^3$, examples of saturated hydrocarbon group include C1-C6 alkyl group such as a methyl group, an ethyl group, a propyl group, a butyl group, a pentyl group and a hexyl group; C3-C6 cycloalkyl group such as a cyclopropyl group, a cyclobutyl group, a cyclopentyl group and a cyclohexyl group; and any combinations of them such as a (cycloalkyl)alkyl group.

$R^2$ is preferably a C1-C6 alkyl group, more preferably a methyl group or an ethyl group, and still more preferably a methyl group.

$R^3$ is preferably a hydrogen atom, a methyl group or an ethyl group, and more preferably a hydrogen atom or a methyl group, and still more preferably a hydrogen atom.

Examples of a divalent aromatic hydrocarbon group represented by Ar include a C6-C36 arylene group such as a phenylene group, a naphthylene group, or an anthrylene group.

The aromatic hydrocarbon group has preferably 6 to 24 carbon atoms, more preferably 6 to 18 carbon atoms.

Examples of the substituent on the aromatic hydrocarbon group include a hydroxy group, a halogen atom, a cyano group, a C1-C12 alkyl group, a C1-C12 alkoxy group, a C2-C13 alkoxycarbonyl group, a C2-C13 alkylcarbonyl group, a C2-C13 alkylcarbonyloxy group, a C3-C12 alicyclic hydrocarbon group, a C6-C10 aromatic hydrocarbon group, and any combinations consisting of the these groups.

Examples of a halogen atom include a fluorine atom, a chlorine atom, a bromine atom and an iodine atom.

Examples of the alkyl group include a methyl group, an ethyl group, a propyl group, a butyl group, a pentyl group, a hexyl group, a heptyl group, an octyl group, a nonyl group, a decyl group, an undecyl group and a dodecyl group.

Examples of the alkoxy group include a methoxy group, an ethoxy group, a propoxy group, a butoxy group, a pentyloxy group, a hexyloxy group, an octyloxy group, a 2-ethylhexyloxy group, a nonyloxy group, a decyloxy group, an undecyloxy group, and a dodecyloxy group.

Examples of the alkoxycarbonyl group include a methoxycarbonyl group, an ethoxycarbonyl group and a butoxycarbonyl group.

Examples of the alkylcarbonyl group include an acetyl group, a propionyl group and a butyryl group.

Examples of the alkylcarbonyloxy group include an acetyloxy group, a propionyloxy group and a butyryloxy group.

The alicyclic hydrocarbon group may be a monocyclic one or polycyclic one, examples of which include the following ones.

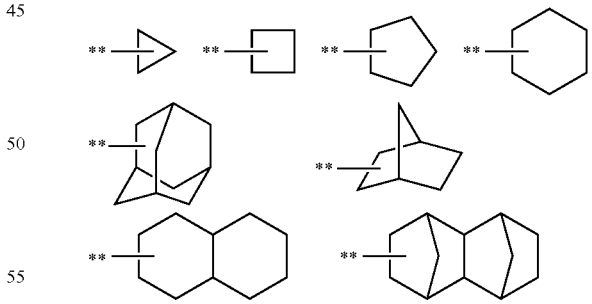

In each group, ** represents a binding position to an aromatic hydrocarbon group.

Examples of the aromatic hydrocarbon group include a phenyl group, a naphthyl group, a tolyl group, a xylyl group, and a cyclohexylphenyl group.

Other substituents on the aromatic hydrocarbon group include a C1-C12 hydroxyalkyl group such as a hydroxymethyl group and a hydroxyethyl group; a C2-C24 alkoxyalkoxy group such as ethoxyethoxy group; and a C7-C22 aralkyl group such as a benzyl group.

Examples of the divalent group represented by $X^1$ include $*-X^{11}-A^{11}-X^{12}-$, $*-X^{13}-A^{12}-X^{14}-A^{13}-$, $*-X^{15}-A^{14}-X^{16}-A^{15}-X^{17}-$ and $*-X^{18}-$ in which * represents a binding position to Ar.

Here, $A^{11}$, $A^{12}$, A13, $A^{14}$ and $A^{15}$ each independently represent a C1-C6 alkanediyl group.

$X^{11}$, $X^{12}$, $X^{13}$, $X^{14}$, $X^{15}$, $X^{16}$, $X^{17}$ and $X^{18}$ each independently represent —O—, —CO—O—, —O—CO— or —O—CO—O—.

Examples of $*-X^{11}-A^{11}-X^{12}-$ include $*-O-CH_2-CO-O-$, $*-O-CO-CH_2-O-$, $*-CO-O-CH_2-O-$, $*-CO-O-CH_2-O-CO-$, $*-CO-O-CH_2-O-CO-O-$, $*-CO-O-CH_2-CO-O-$, and $*-O-CO-O-CH_2-CO-O-$.

Examples of $*-X^{13}-A^{12}-X^{14}-A^{13}-$ include $*-O-CH_2-CO-O-CH_2-$, $*-O-CH_2-O-CO-CH_2-$, $*-CO-O-CH_2-O-CH_2-$, $*-O-CO-O-CH_2-O-CH_2-$, $*-CO-O-CH_2-O-CO-CH_2-$ and $*-CO-O-CH_2-CO-O-CH_2-$.

Examples of $*-X^{15}-A^{14}-X^{16}-A^{15}-X^{17}-$ include $*-O-CH_2-CO-O-CH_2-CO-O-$, $*-O-CO-O-CH_2-CO-O-CH_2-CO-O-$, $*-O-CH_2-O-CO-CH_2-CO-O-$, $*-CO-O-CH_2-O-CH_2-CO-O-$, $*-CO-O-CH_2-OCO-CH_2-CO-O-$ and $*-CO-O-CH_2-CO-O-CH_2-CO-O-$.

Examples of $*-X^{18}-$ include —O—, $*-CO-O-$, $*-O-CO-$ and —O—CO—O—.

$X^1$ is preferably $*-X^{11}-A^{11}-X^{12}-$ or $*-X^{18}-$, more preferably $*-O-CH_2-CO-O-$, $*-O-CO-CH_2-O-$, $*-CO-O-CH_2-CO-O-$, $*-O-CO-O-CH_2-O-$, $*-CO-O-CH_2-O-$, $*-CO-O-CH_2-O-CO-$, —O—CO—O—, or $*-CO-O-$, still more preferably $*-O-CH_2-CO-O-$, $*-O-CO-CH_2-O-$, $*-CO-O-CH_2-CO-O-$, $*-CO-O-$, $*-O-CO-$ or —O—CO—O—, and further more preferably $*-O-CH_2-CO-O-$, $*-CO-O-$ or —O—CO—O—.

Examples of Compound (I) include the following ones and the compounds represented by formulae (I-1) to (I-8) in which a methyl group bonded to $CH_2=CH-$ has been replaced by a hydrogen atom.

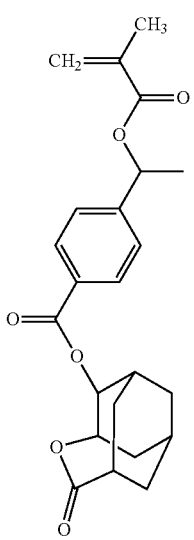

(I-1)

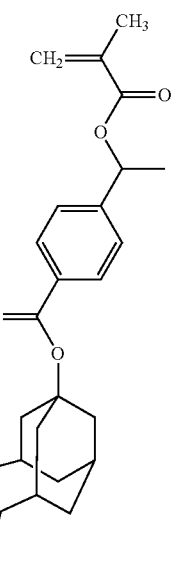

(I-2)

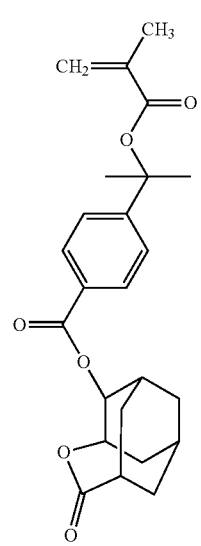

(I-3)

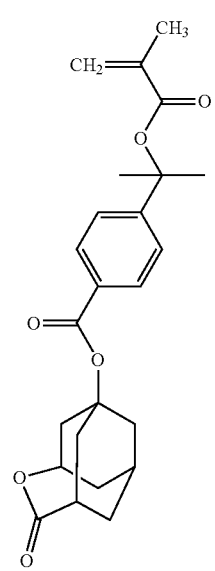

(I-4)

(I-5)

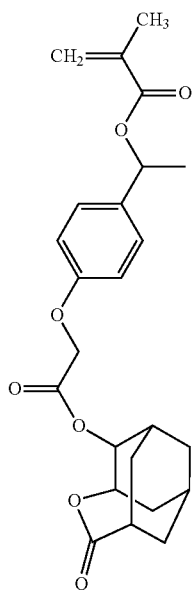

(I-6)

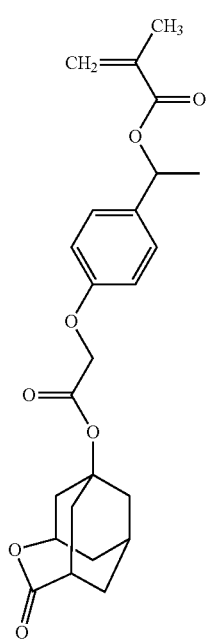

(I-7)

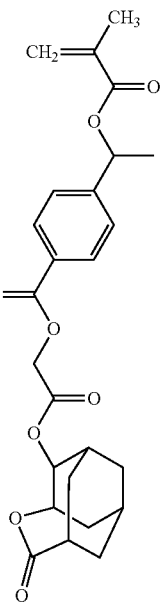

(I-8)

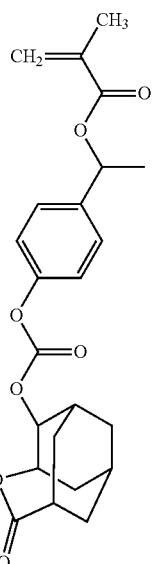

Among them, preferred are the compounds represented by formulae (I-1), (I-2), (I-5), (I-6), (I-7) and (I-8), more preferred are the compounds represented by formulae (I-1), (I-2), (I-5), (I-6) and (I-8), and still more preferred are the compounds represented by formulae (I-1), (I-2), (I-5) and (I-6).

<Process for Producing Compound (I)>

Compound (I) can be produced by reacting a compound represented by formula (I-a) and a compound represented by formula (I-b) in the presence of a base catalyst in a solvent.

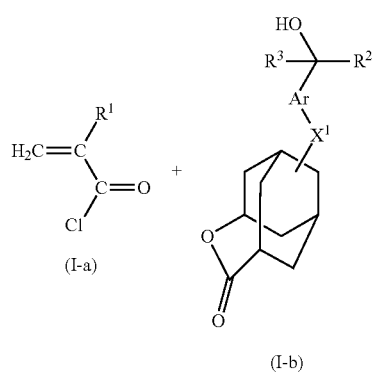

(I-a)
(I-b)

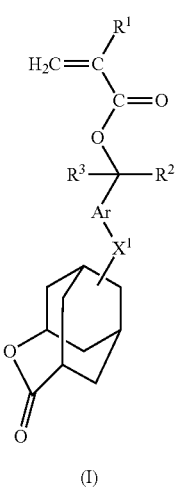

(I)

In the reaction formula, $R^1$, $R^2$, $R^3$, Ar and $X^1$ are as defined above.

Examples of the base catalyst include pyridine.

Examples of the solvent include tetrahydrofuran, chloroform and acetonitrile.

The reaction temperature is usually from 0 to 80° C., and the reaction time is usually from 0.5 to 24 hours.

Examples of the compound represented by the formula (I-a) include the following compounds, which are available in the market.

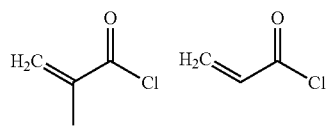

The compound represented by the formula (I1-b), i.e. the compound represented by the formula (I-b) in which $R^2$ is a methyl group, $R^3$ is a hydrogen atom and $X^1$ is —CO—O—, can be produced by reducing a compound represented by the formula (I1-c) in a solvent.

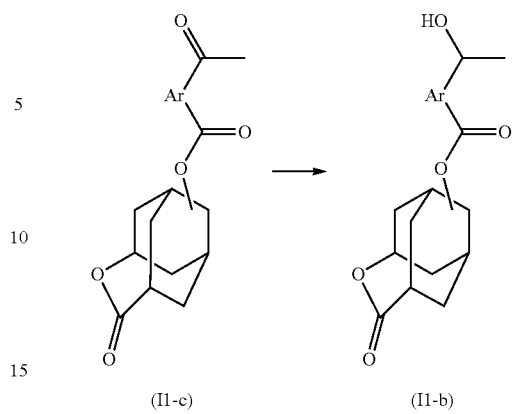

(I1-c)
(I1-b)

In the reaction formula, Ar is as defined above.

Examples of the solvent include tetrahydrofuran, chloroform and acetonitrile.

Examples of the reducing agent include lithium aluminum hydride and sodium borohydride.

The reaction temperature is usually from 0 to 80° C., and the reaction time is usually from 0.5 to 24 hours.

The compound represented by formula (I1-c) can be produced by reacting a compound represented by formula (I1-d) and carbonyldiimidazole in a solvent, and further reacting with a compound represented by formula (I1-e).

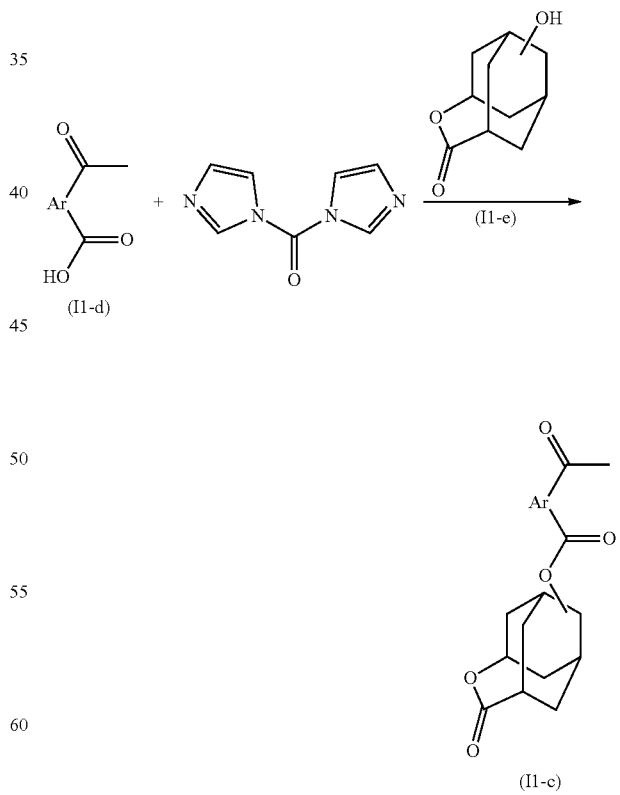

(I1-d)
(I1-e)

(I1-c)

Examples of the compound represented by the formula (I1-d) include the following compound, which is available in the market.

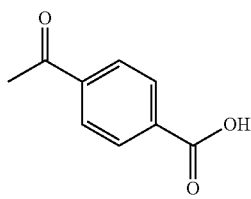

Examples of the compound represented by the formula (I1-e) include the following compounds, which are available in the market.

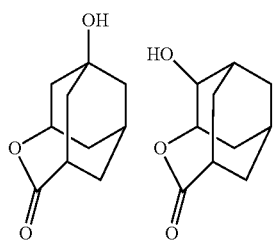

The compound represented by the formula (I-b), i.e. the compound represented by the formula (I1-b) in which $R^3$ is a hydrogen atom and $X^1$ is —O—CO—, can be produced by reducing a compound represented by the formula (I2-c) in a solvent.

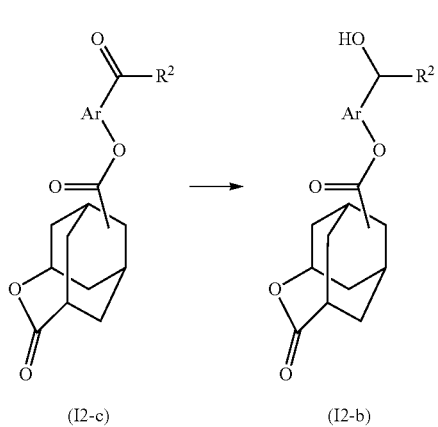

In the reaction formula, $R^2$ and Ar are as defined above.

Examples of the solvent include tetrahydrofuran, chloroform and acetonitrile.

The reaction temperature is usually from 15 to 80° C., and the reaction time is usually from 0.5 to 24 hours.

The compound represented by the formula (I2-c) can be produced by reacting a compound represented by the formula (I2-e) with carbonyldiimidazole and further reacting with a compound represented by the formula (I2-d).

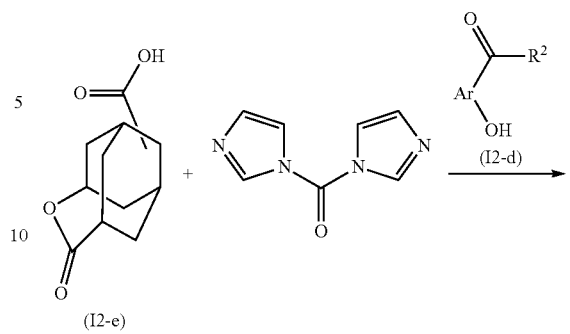

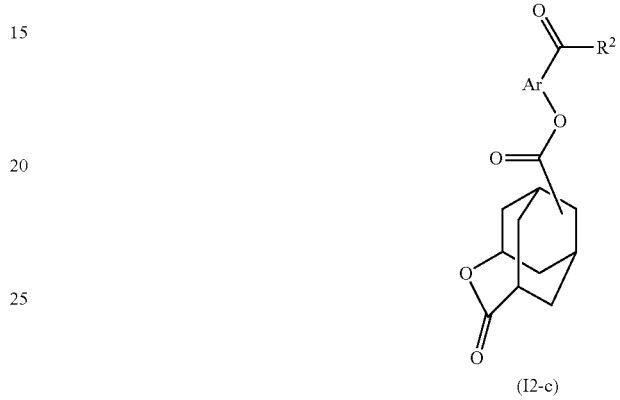

Examples of the solvent include tetrahydrofuran, chloroform and acetonitrile.

The reaction temperature is usually from 15 to 80° C., and the reaction time is usually from 0.5 to 24 hours.

Examples of the compound represented by the formula (I2-d) include the following compound, which are available in the market.

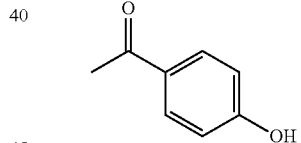

Examples of the compound represented by the formula (I2-e) include the following compound, which are available in the market.

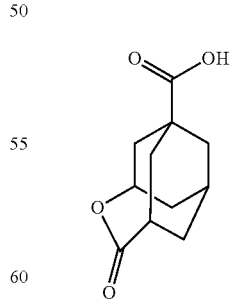

The compound represented by the formula (I3-b), i.e. the compound represented by the formula (I-b) in which $R^3$ is a hydrogen atom and $X^1$ is —O—CO—O—, can be produced by reducing a compound represented by the formula (I3-c) in a solvent.

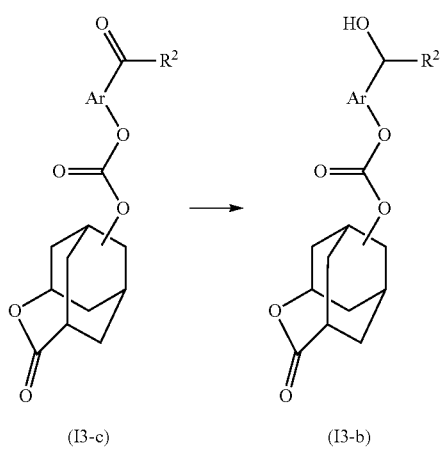

(I3-c)   (I3-b)

In the reaction formula, R² and Ar are as defined above.

Examples of the solvent include tetrahydrofuran, chloroform and acetonitrile.

Examples of the reducing agent include lithium aluminum hydride and sodium borohydride.

The reaction temperature is usually from 0 to 80° C., and the reaction time is usually from 0.5 to 24 hours.

The compound represented by the formula (I3-c) can be produced by reacting a compound represented by formula (I1-e) and carbonyldiimidazole in a solvent, followed by reacting a compound represented by formula (I2-d).

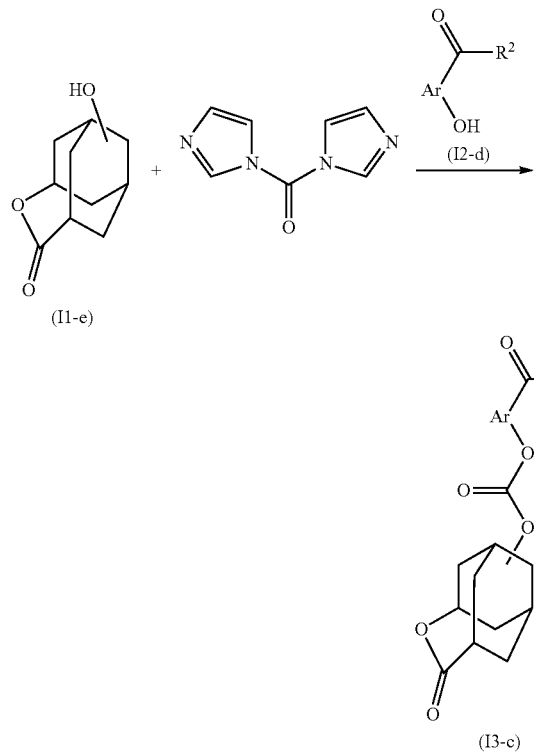

(I3-c)

Examples of the solvent include tetrahydrofuran, chloroform and acetonitrile.

The reaction temperature is usually from 15 to 80° C., and the reaction time is usually from 0.5 to 24 hours.

The compound represented by the formula (I4-b), i.e. the compound represented by the formula (I-b) in which R³ is a hydrogen atom and X¹ is —O—, can be produced by reducing a compound represented by the formula (I4-c) in solvent.

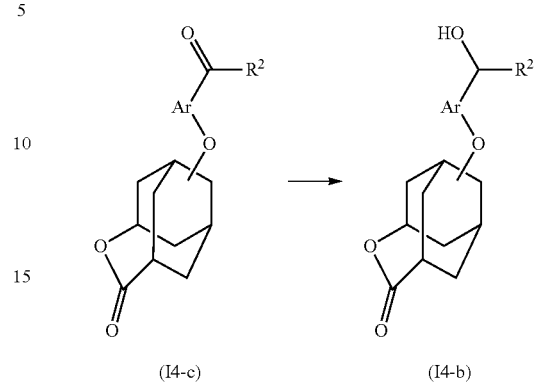

(I4-c)   (I4-b)

In the reaction formula, R² and Ar are as defined above.

Examples of the solvent include tetrahydrofuran, chloroform and acetonitrile.

Examples of the reducing agent include lithium aluminum hydride and sodium borohydride.

The reaction temperature is usually from 0 to 80° C., and the reaction time is usually from 0.5 to 24 hours.

The compound represented by formula (I4-c) can be produced by reacting a compound represented by formula (I1-e) and a compound represented by formula (I2-d) in the presence of a base catalyst in a solvent.

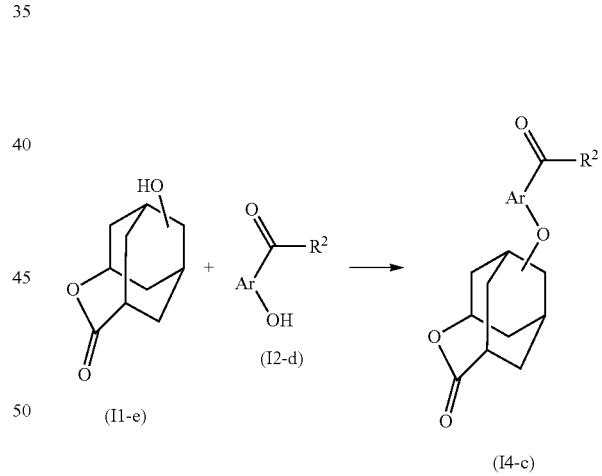

(I1-e)   (I2-d)   (I4-c)

In the reaction formula, R² and Ar are as defined above.

Examples of the base catalyst include potassium hydroxide.

Examples of the solvent include acetonitrile.

The reaction temperature is usually from 5 to 80° C., and the reaction time is usually from 0.5 to 24 hours.

The compound represented by the formula (I5-b), i.e. the compound represented by the formula (I-b) in which X¹ is —CO—O—, can be produced by reacting a compound represented by formula (I5-d) and carbonyldiimidazole in a solvent, and further reacting with a compound represented by formula (I1-e).

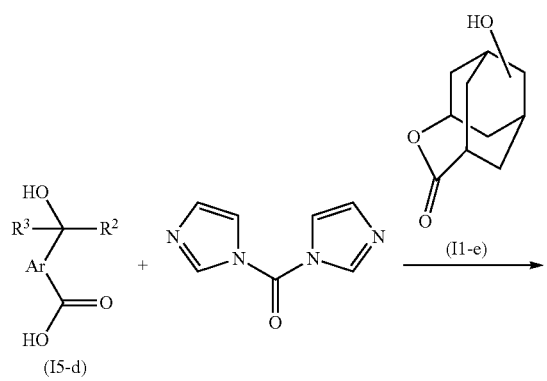

(I5-d)

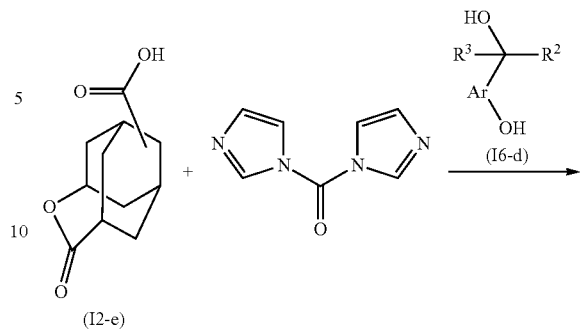

(I2-e) (I6-d)

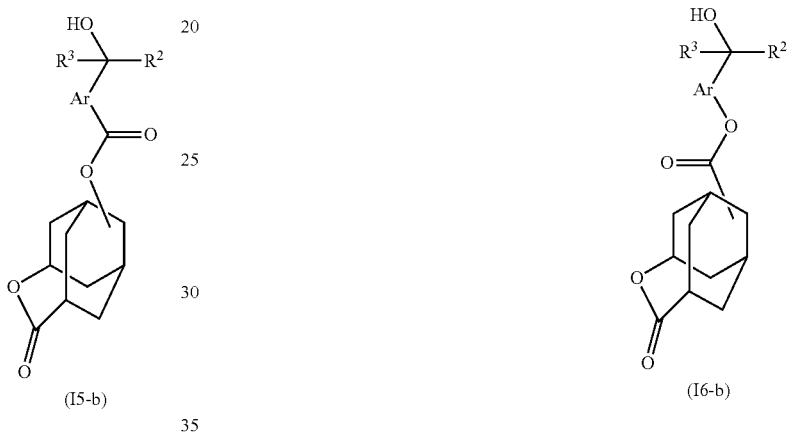

(I5-b)  (I6-b)

In the reaction formula, $R^2$, $R^3$ and Ar are as defined above.

Examples of the solvent include tetrahydrofuran, chloroform and acetonitrile.

The reaction temperature is usually from 15 to 80° C., and the reaction time is usually from 0.5 to 24 hours.

Examples of the compound represented by the formula (I5-d) include the following compound, which is available in the market.

In the reaction formula, $R^2$, $R^3$ and Ar are as defined above.

Examples of the solvent include tetrahydrofuran, chloroform and acetonitrile.

The reaction temperature is usually from 15 to 80° C., and the reaction time is usually from 0.5 to 24 hours.

Examples of the compound represented by the formula (I6-d) include the following compound, which is available in the market.

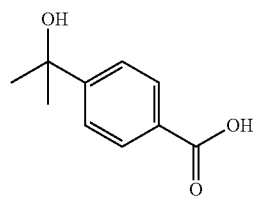

The compound represented by the formula (I6-b), i.e. the compound represented by the formula (I-b) in which $X^1$ is —O—CO—, can be produced by reacting a compound represented by formula (I2-e) and carbonyldiimidazole in a solvent, and further reacting with a compound represented by formula (I6-d).

The compound represented by the formula (I7-b), i.e. the compound represented by the formula (I-b) in which $X^1$ is —O—CO—O—, can be produced by reacting a compound represented by formula (I1-e) and carbonyldiimidazole in a solvent, and further reacting with a compound represented by formula (I6-d).

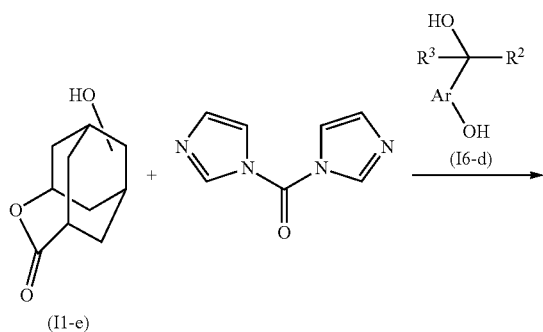

(I1-e) + (I6-d) →

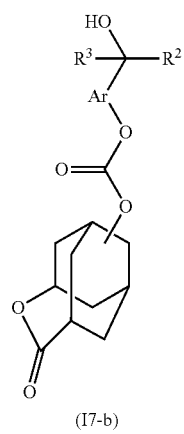

(I7-b)

In the reaction formula, $R^2$, $R^3$ and Ar are as defined above.

Examples of the solvent include tetrahydrofuran, chloroform and acetonitrile.

The reaction temperature is usually from 15 to 80° C., and the reaction time is usually from 0.5 to 24 hours.

The compound represented by formula (I8-b) can be produced by reacting a compound represented by formula (I1-e) and a compound represented by formula (I6-d) in the presence of a base catalyst in a solvent.

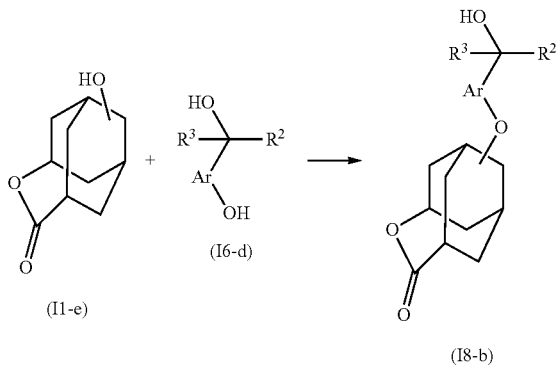

(I1-e) + (I6-d) → (I8-b)

In the reaction formula, $R^2$, $R^3$ and Ar are as defined above.

Examples of the base catalyst include potassium hydroxide.

Examples of the solvent include acetonitrile.

The reaction temperature is usually from 5 to 80° C., and the reaction time is usually from 0.5 to 24 hours.

<Resin>

The resin of the disclosure comprises a structural unit derived from the compound (I). Hereinafter, the resin and the structural unit are sometimes referred to as "Resin (A)" and "structural unit (I)".

Resin (A) may consist of a single structural unit (I) or two or more kinds of the structural units (I), or may further comprise another structural unit than the structural unit (I).

When Resin (A) further comprises the another structural unit, the structural unit represented by the formula (I) is present in an amount of usually 5% to 90% by mole, preferably 10% to 80% by mole, more preferably 10% to 50% by mole.

Examples of the another structural unit include other structural units having an acid-labile group and being different from the structural unit (I) [which structural unit is sometimes referred to as "the structural unit (a1)"], and structural units having no acid-labile group [which structural unit is sometimes referred to as "the structural unit (s)"].

Herein, "an acid-labile group" means a group which has a hydrophilic group, such as a hydroxy group or a carboxy group, resulting from removing a leaving group therefrom by the action of an acid.

<Structural Unit (a1)>

The structural unit (a1) is derived from a compound having an acid-labile group which compound is sometimes referred to as "Monomer (a1)".

For Resin (A), the acid-labile groups represented by formulae (1) and (2) are preferred.

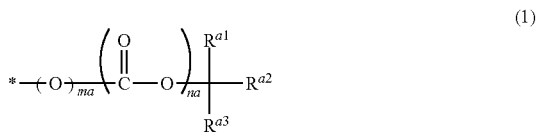

(1)

In formula (1), $R^{a1}$, $R^{a2}$ and $R^{a3}$ independently each represent a C1-C8 alkyl group, a C3-C20 alicyclic hydrocarbon group or a group consisting of them, and $R^{a1}$ and $R^2$ can be bonded each other to form a C3-C20 alicyclic hydrocarbon group together with the carbon atom to which $R^{a1}$ and $R^{a2}$ are bonded, "na" and "ma" each represent an integer of 0 or 1 provided that at least one of them represents 1, and * represents a binding position.

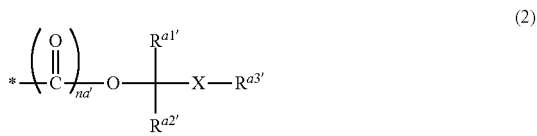

(2)

In formula (2), $R^{a1'}$ and $R^{a2'}$ independently each represent a hydrogen atom or a C1-C12 hydrocarbon group, and $R^{a3'}$ represents a C1-C20 hydrocarbon group, and $R^{a2'}$ and $R^{a3'}$ can be bonded each other to form a C3-C20 heterocyclic group together with X and the carbon atom to which $R^{a2'}$ and $R^{a3'}$ are bonded, and one or more —$CH_2$— in the hydrocarbon group and the heterocyclic group can be replaced by —O— or —S—, X represents an oxygen atom or a sulfur atom, "na'" represents an integer of 0 or 1, and * represents a binding position.

For $R^{a1}$, $R^{a2}$ and $R^{a3}$, specific examples of the alkyl group include a methyl group, an ethyl group, a propyl group, an isopropyl group, a butyl group, a pentyl group, a hexyl group, a heptyl group and an octyl group.

The alicyclic hydrocarbon group may be monocyclic or polycyclic.

Examples of the alicyclic hydrocarbon group include a monocyclic alicyclic hydrocarbon group such as a C3-C20 cycloalkyl group (e.g. a cyclopentyl group, a cyclohexyl group, a cycloheptyl group and a cyclooctyl group) and a polycyclic alicyclic hydrocarbon group such as a decahydronaphthyl group, an adamantyl group, a norbornyl group, and the followings:

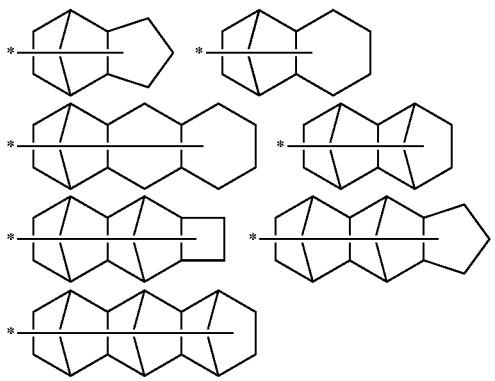

in which * represents a binding position.

The alicyclic hydrocarbon group preferably has 3 to 16 carbon atoms.

Examples of the group consisting of alkyl and alicyclic hydrocarbon group include a methylcyclohexyl group, a dimethylcyclohexyl group, a methylnorbornyl group, an adamantylmethyl group, and a norbornylethyl group.

The "ma" is preferably 0. The "na" is preferably 1.

When the alicyclic hydrocarbon group is formed by bonding $R^{a1}$ and $R^{a2}$ each other, examples of the moiety —C($R^{a1}$)($R^{a2}$)($R^{a3}$) include the following groups and the alicyclic hydrocarbon group preferably has 3 to 12 carbon atoms.

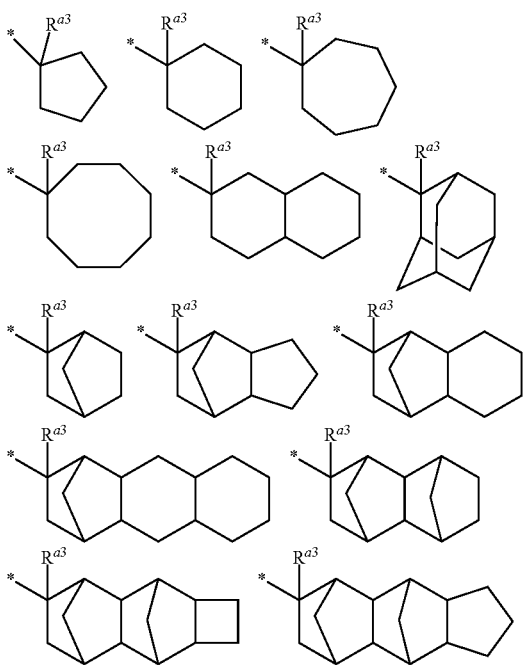

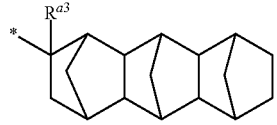

wherein $R^{a3}$ is the same as defined above and * represents a binding position.

For formula (2), examples of the hydrocarbon group include an alkyl group, an alicyclic hydrocarbon group, an aromatic hydrocarbon group and any combination of these groups.

Examples of the aliphatic hydrocarbon group and the alicyclic hydrocarbon group include the same as described above. Examples of the aromatic hydrocarbon group include an aryl group such as a phenyl group, a naphthyl group, a p-methylphenyl group, a p-tert-butylphenyl group, a p-adamantylphenyl group, a tolyl group, a xylyl group, a cumyl group, a mesityl group, a biphenyl group, an anthryl group, a phenanthryl group, a 2,6-diethylphenyl group and a 2-methyl-6-ethylphenyl group.

Examples of the combination of these groups include a group which consists of an alkyl group and an alicyclic hydrocarbon group, e.g. cycloalkyl groups; aralkyl groups such as a benzyl group; and aryl-cyclohexyl groups such as a phenylcyclohexyl group.

Examples of the heterocyclic group formed by bonding $R^{a2'}$ and $R^{a3'}$ together with X and the carbon atom to which $R^{a2'}$ and $R^{a3'}$ are bonded include the following ones.

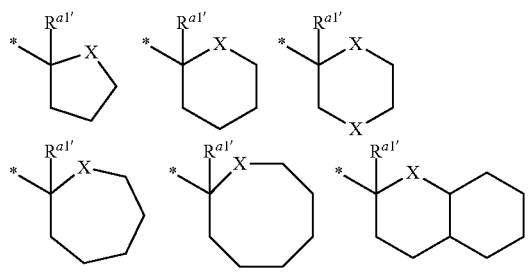

wherein * represents a binding position.

In formula (2), at least one of $R^{a1'}$ and $R^{a2'}$ is preferably a hydrogen atom.

The "na'" is preferably 0.

Examples of the group represented by formula (1) include the following ones:

The group represented by formula (1) wherein $R^{a1}$, $R^{a2}$ and $R^{a3}$ independently each represent a C1-C8 alkyl group, ma is 0, and na is 1, such as a tert-butyl group The group represented by formula (1) wherein $R^{a1}$ and $R^{a2}$ are bonded each other to form an adamantyl ring, $R^{a3}$ is a C1-C8 alkyl group, ma is 0, and na is 1, such as a 2-alkyl-2-adamantyl group The group represented by formula (1) wherein $R^{a1}$ and $R^{a2}$ are C1-C8 alkyl groups, $R^{a3}$ is an adamantyl group, ma is 0, and na is 1, such as a 1-(1-adamantyl)-1-alkylalkoxycarbonyl group.

Specific examples of the group represented by formula (1) include the followings.

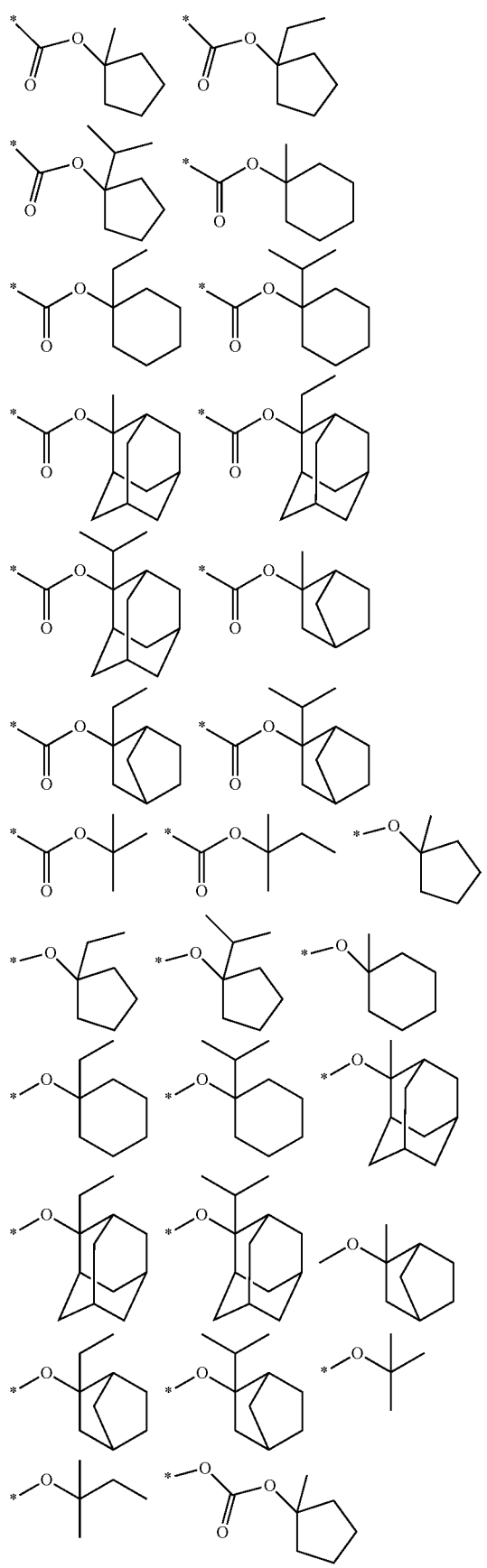
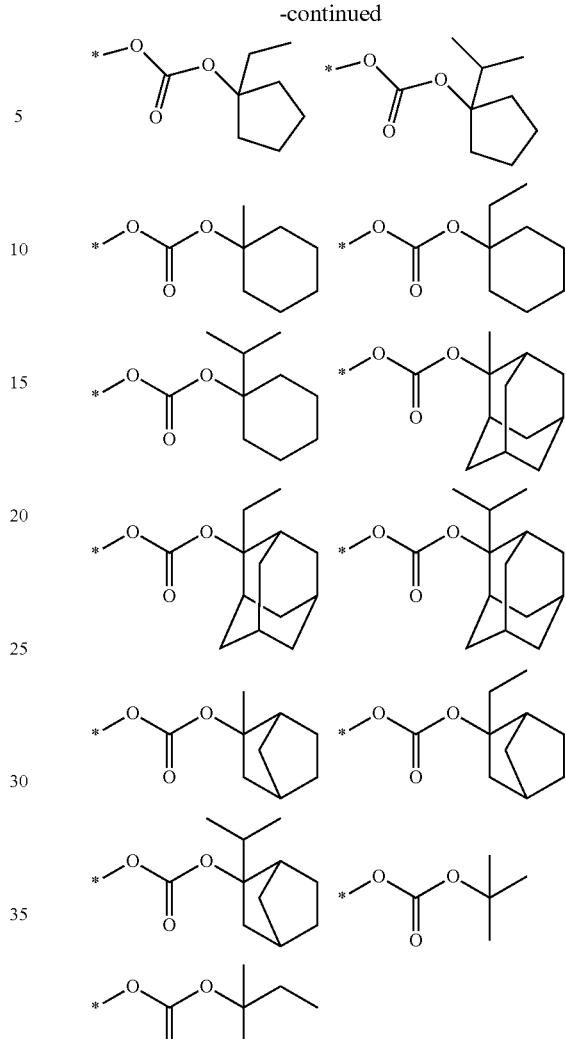
Specific examples of the group represented by formula (2) include the following.
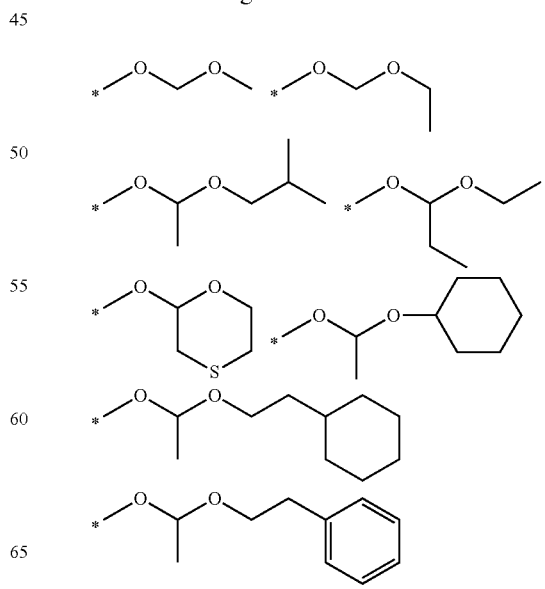

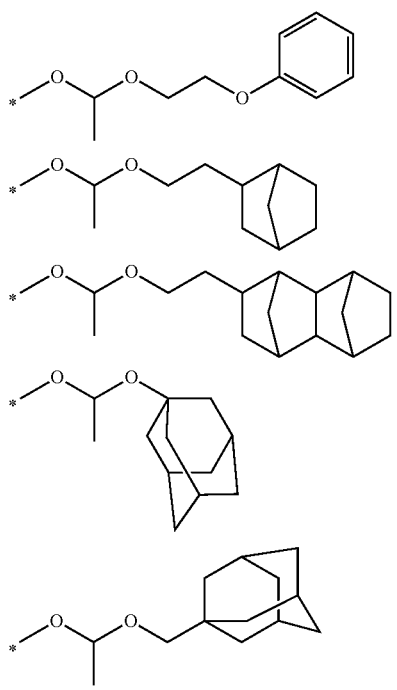

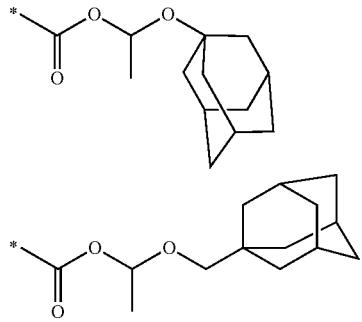

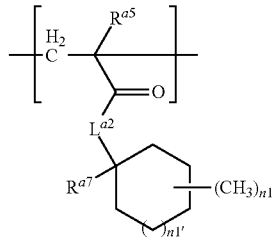

Monomer (a1) is preferably a monomer having an acid-labile group in its side chain and an ethylenic unsaturated group, more preferably a (meth)acrylate monomer having an acid-labile group in its side chain, and still more preferably a (meth)acrylate monomer having the group represented by formula (1) or (2).

The (meth)acrylate monomer having an acid-labile group in its side chain is preferably those which comprise a C5-C20 alicyclic hydrocarbon group. The resin which comprises a structural unit derived from such monomers can provide improved resolution for a photoresist pattern to be prepared therefrom.

The structural unit derived from a (meth)acrylate monomer having the group represented by formula (1) is preferably one of structural units represented by formulae (a1-0), (a1-1) and (a1-2).

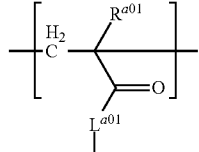
(a1-0)

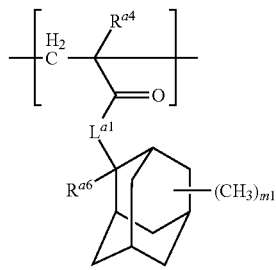
(a1-1)

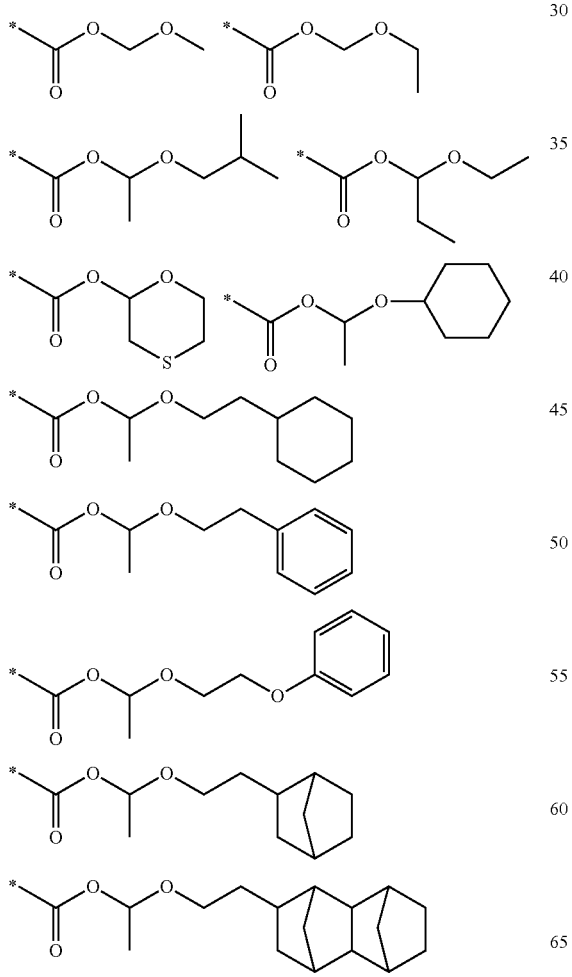

(a1-2)

In each formula, $L^{a01}$, $L^{a1}$ and $L^{a2}$ each independently represent —O— or *—O—$(CH_2)_{k1}$—CO—O— in which k1 represents an integer of 1 to 7 and * represents a binding position to —CO—, $R^{a01}$, $R^{a4}$ and $R^{a5}$ each independently represent a hydrogen atom or a methyl group, $R^{a02}$, $R^{a03}$, $R^{a04}$, $R^{a6}$ and $R^{a7}$ each independently represent a C1-C8 alkyl group, a C3-C18 alicyclic hydrocarbon group, or a group formed by combining them, m1 represents an integer of 0 to 14, n1 represents an integer of 0 to 10, and n1' represents an integer of 0 to 3.

Hereinafter, the structural units represented by formulae (a1-0), (a1-1) and (a1-2) are referred to as "structural unit (a1-0)", "structural unit (a1-1)" and "structural unit (a1-2)", respectively.

Resin (A) may comprise two or more of such structural units.

$L^{a01}$ is preferably *—O— or *—O—$(CH_2)_{f1}$—CO—O— in which * represents a binding position to —CO—, and f1 represents an integer of 1 to 4, and is more preferably *—O— or *—O—$CH_2$—CO—O—, and is especially preferably *—O—.

$R^{a01}$ is preferably a methyl group.

For $R^{a02}$, $R^{a03}$ and $R^{a04}$, examples of the alkyl group, the alicyclic hydrocarbon group and the group formed by combining them include the same as referred for $R^{a1}$, $R^{a2}$ and $R^{a3}$.

The alkyl group has preferably 1 to 6 carbon atoms. The alkyl group is more preferably a methyl group, an ethyl group or an isopropyl group, still more preferably an ethyl group or an isopropyl group. The alicyclic hydrocarbon group preferably has 5 to 12 carbon atoms and more preferably 5 to 10 carbon atoms. The alicyclic hydrocarbon group is preferably a saturated aliphatic cyclic hydrocarbon group.

The group formed by combining them preferably has 18 carbon atoms or less in total, examples of which include a methylcyclohexyl group, a dimethylcyclohexyl group, and a methylnorbornyl group. Each of $R^{a02}$ and $R^{a03}$ is preferably a C1-C6 alkyl group, more preferably a methyl group and an ethyl group.

$R^{a04}$ is preferably a C1-C6 alkyl group and a C5-C12 alicyclic hydrocarbon group, more preferably a methyl group, an ethyl group, a cyclohexyl group, and an adamantyl group.

Each of $L^{a1}$ and $L^{a2}$ is preferably *—O— or *—O—$(CH_2)_{f1}$—CO—O— in which * represents a binding position to —CO—, and f1 is the same as defined above, and is more preferably *—O— or *—O—$CH_2$—CO—O—, and is especially preferably *—O—.

Each of $R^{a4}$ and $R^{a5}$ is preferably a methyl group.

For $R^{a6}$ and $R^{a7}$, examples of the alkyl group include a methyl group, an ethyl group, a propyl group, an isopropyl group, a butyl group, a tert-butyl group, a pentyl group, a heptyl group, a 2-ethylheptyl group and an octyl group.

For $R^{a6}$ and $R^{a7}$, examples of the alicyclic hydrocarbon group include a monocyclic alicyclic hydrocarbon group such as a cyclohexyl group, a methylcyclohexyl group, a dimethylcyclohexyl group, a cycloheptyl group and a methylcycloheptyl group, and a polycyclic alicyclic hydrocarbon group such as a decahydronaphthyl group, an adamantyl group, a norbornyl group, and a methylnorbornyl group.

For $R^{a6}$ and $R^{a7}$, examples of the group consisting of an alkyl group and an alicyclic hydrocarbon group include an aralkyl group such as a benzyl group, and a phenethyl group.

The alkyl group represented by $R^{a6}$ and $R^{a7}$ is preferably a C1-C6 alkyl group, more preferably a methyl group, an ethyl group or an isopropyl group, and still more preferably an ethyl group, or an isopropyl group.

The alicyclic hydrocarbon group represented by $R^{a6}$ and $R^{a7}$ is preferably a C3-C8 alicyclic hydrocarbon group, more preferably a C3-C6 alicyclic hydrocarbon group.

The "m1" is preferably an integer of 0 to 3, and is more preferably 0 or 1.

The "n1" is preferably an integer of 0 to 3, and is more preferably 0 or 1.

The "n1'" is preferably 0 or 1.

Examples of the structural unit (a1-0) include those represented by formulae (a1-0-1) to (a1-0-12) and such groups that a methyl group has been replaced by a hydrogen atom in any one of formulae (a1-0-1) to (a1-0-12), preferably those represented by formulae (a1-0-1) to (a1-0-10) and such groups that a methyl group has been replaced by a hydrogen atom in any one of formulae (a1-0-1) to (a1-0-10).

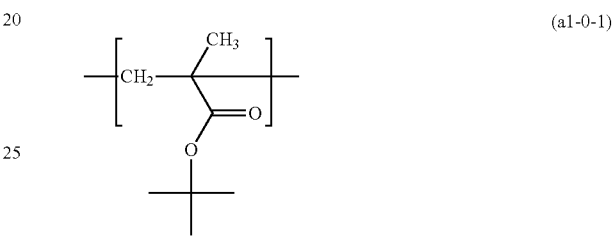

(a1-0-1)

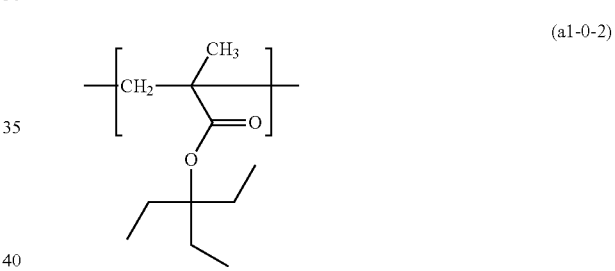

(a1-0-2)

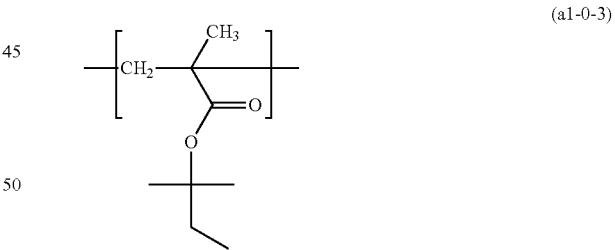

(a1-0-3)

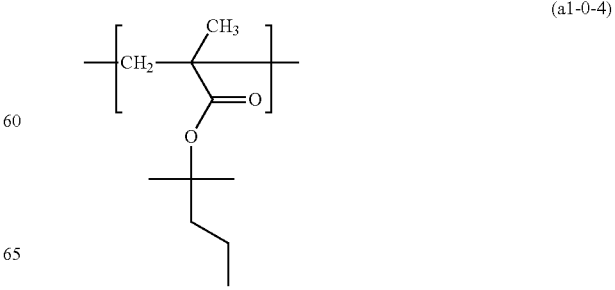

(a1-0-4)

(a1-0-5) 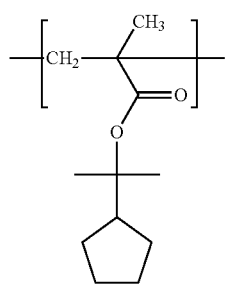
(a1-0-6) 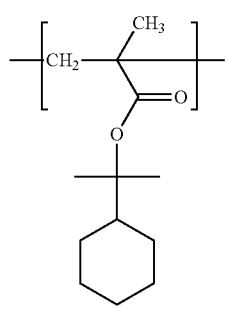
(a1-0-7) 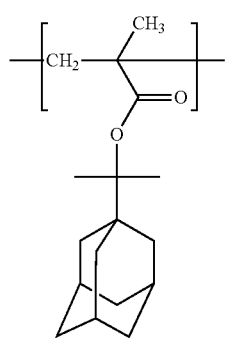
(a1-0-8) 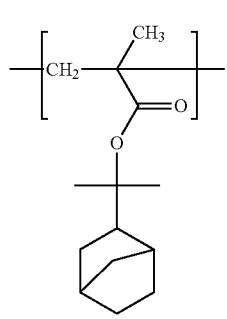
(a1-0-9) 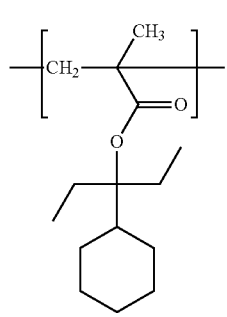
(a1-0-10) 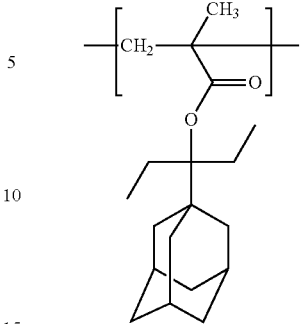
(a1-0-11) 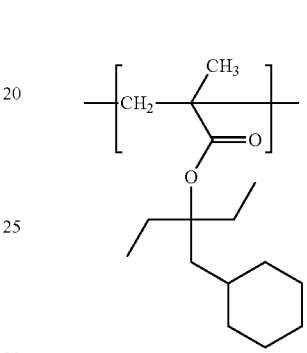
(a1-0-12) 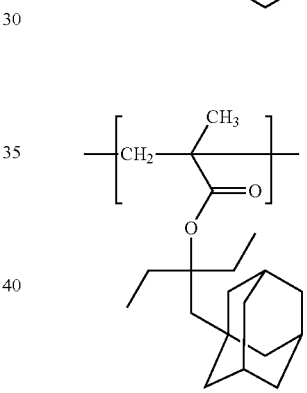
Examples of the monomer from which the structural unit (a1-1) is derived include the monomers described in JP2010-204646A1, and the following monomers represented by the formulae (a1-1-1) to (a1-1-4) and such groups that a methyl group has been replaced by a hydrogen atom in any one of formulae (a1-1-1) to (a1-1-4), preferably the following monomers represented by the formulae (a1-1-1) to (a1-1-4).
(a1-1-1) 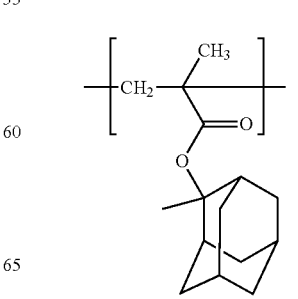

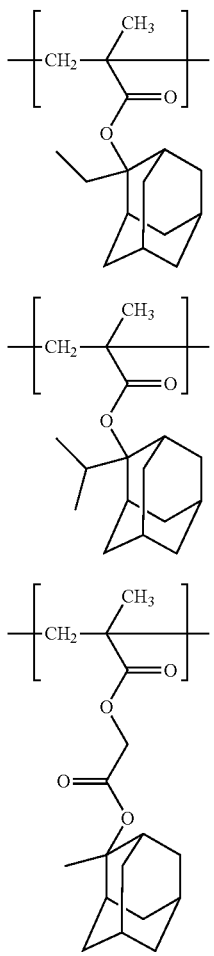

(a1-1-2)

(a1-1-3)

(a1-1-4)

Preferred examples of the structural unit (a1-2) include ones represented by formulae (a1-2-1) to (a1-2-6) and those represented by the formulae in which a methyl group corresponding to $R^{a5}$ has been replaced by a hydrogen atom, more preferably the monomers represented by formulae (a1-2-2), (a1-2-5) and (a1-2-6).

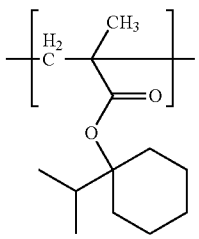

(a1-2-1)

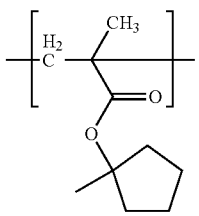

(a1-2-2)

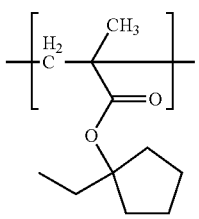

(a1-2-3)

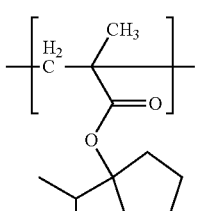

(a1-2-4)

(a1-2-5)

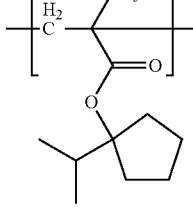

(a1-2-6)

When the resin comprises one or more of the structural units represented by formulae (a1-0), (a1-1) and (a1-2), the total content of the structural units is usually 10 to 95% by mole, preferably 15 to 70% by mole and more preferably 15 to 65% by mole, still more preferably 20 to 60% by mole, and further more preferably 20 to 55% by mole, based on 100% by mole of all the structural units of the resin.

Examples of the structural unit (a1) having the group represented by formula (2) include a structural unit represented by formula (a1-4). The structural unit is sometimes referred to as "structural unit (a1-4)".

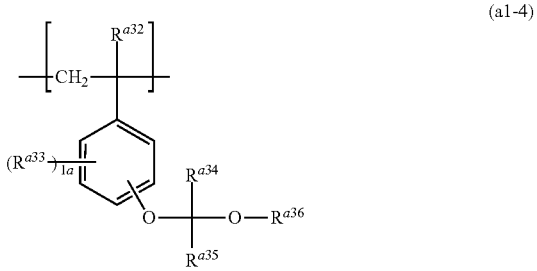

(a1-4)

In the formula, $R^{a32}$ represents a hydrogen atom, a halogen atom or a C1-C6 alkyl group that may have a halogen atom, $R^{a33}$ in each occurrence independently represent a halogen atom, a hydroxy group, a C1-C6 alkyl group, a C1-C6 alkoxy group, a C2-C4 acyl group, a C2-C4 acyloxy group, an acryloyloxy group or methacryloyloxy group, "la" represents an integer 0 to 4, $R^{a34}$ and $R^{a35}$ each independently represent a hydrogen atom or a C1-C12 hydrocarbon group; and $R^{a36}$ represents a C1-C20 hydrocarbon group, or $R^{a35}$ and $R^{a36}$ may be bonded together with a C—O bonded thereto to form a divalent C3-C20 heterocyclic group, and a methylene group contained in the hydrocarbon group or the divalent heterocyclic group may be replaced by an oxygen atom or a sulfur atom.

Examples of the alkyl group of $R^{a32}$ and $R^{a33}$ include methyl, ethyl, propyl, isopropyl, butyl, pentyl and hexyl groups. The alkyl group is preferably a C1-C4 alkyl group, and more preferably a methyl group or an ethyl group, and still more preferably a methyl group.

Examples of the halogen atom of $R^{a32}$ and $R^{a33}$ include a fluorine, chlorine, bromine and iodine atoms.

Examples of the alkyl group that may have a halogen atom include trifluoromethyl, difluoromethyl, methyl, perfluoroethyl, 2,2,2-trifluoroethyl, 1,1,2,2-tetrafluoroethyl, ethyl, perfluoropropyl, 2,2,3,3,3-pentafluoropropyl, propyl, perfluorobutyl, 1,1,2,2,3,3,4,4-octafluorobutyl, butyl, perfluoropentyl, 2,2,3,3,4,4,5,5-nonafluoropentyl, n-pentyl, n-hexyl and n-perfluorohexyl groups.

Examples of an alkoxy group include methoxy, ethoxy, propoxy, butoxy, pentyloxy and hexyloxy groups. The alkoxy group is preferably a C1-C4 alkoxy group, more preferably a methoxy group or an ethoxy group, and still more preferably a methoxy group.

Examples of the acyl group include acetyl, propionyl and butyryl groups. Examples of the acyloxy group include acetyloxy, propionyloxy and butyryloxy groups. Examples of the hydrocarbon group for $R^{a34}$ and $R^{a35}$ are the same examples as described in $R^{a1'}$ to $R^{a2'}$ in the formula (2).

Examples of hydrocarbon group for $R^{a36}$ include a C1-C18 alkyl group, a C3-C18 alicyclic hydrocarbon group, a C6-C18 aromatic hydrocarbon group or a group formed by combining thereof.

In the formula (a1-4), $R^{a32}$ is preferably a hydrogen atom.

$R^{a33}$ is preferably a C1-C4 alkoxy group, more preferably a methoxy group or an ethoxy group, and still more preferably a methoxy group.

"la" is preferably 0 or 1, and more preferably 0. $R^{a34}$ is preferably a hydrogen atom. $R^{a35}$ is preferably a C1-C12 hydrocarbon group, and more preferably a methyl group or an ethyl group.

The hydrocarbon group for $R^{a36}$ is preferably a C1-C18 alkyl group, a C3-C18 alicyclic hydrocarbon group, a C6-C18 aromatic hydrocarbon group or a combination thereof, and more preferably a C1-C18 alkyl group, a C3-C18 alicyclic hydrocarbon group or a C7-C18 aralkyl group. The alkyl group and the alicyclic hydrocarbon group for $R^{a36}$ are preferably unsubstituted. When the aromatic hydrocarbon group of $R^{a36}$ has a substituent, the substituent is preferably a C6-C10 aryloxy group.

Examples of the structural unit (a1-4) include those derived from the monomers described in JP2010-204646A1. Among them, the structural unit is preferably the following ones represented by formula (a1-4-1) to formula (a1-4-8), and more preferably the structural units represented by formula (a1-4-1) to formula (a1-4-5).

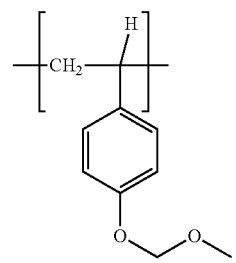
(a1-4-1)

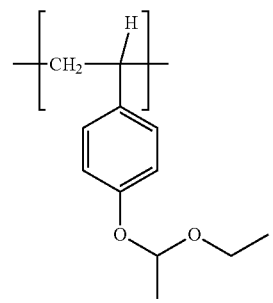
(a1-4-2)

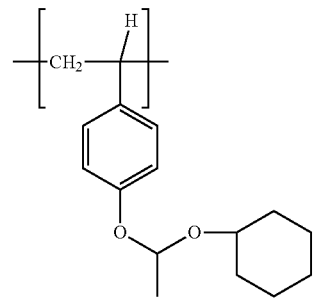
(a1-4-3)

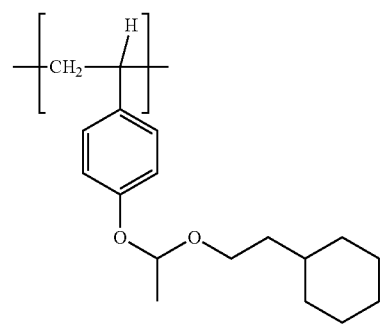
(a1-4-4)

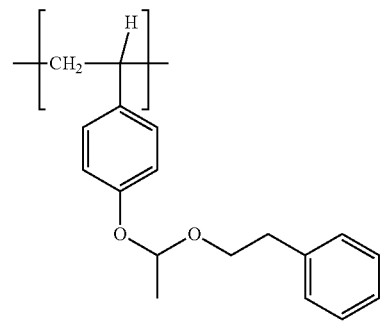
(a1-4-5)

-continued (a1-4-6)

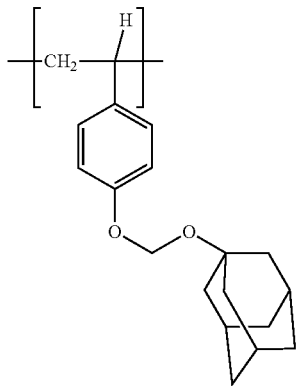

(a1-4-7)

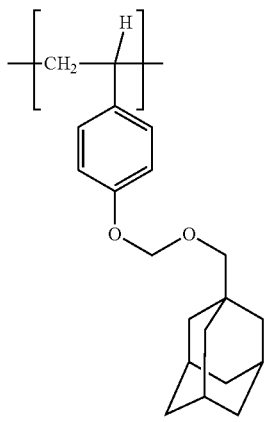

(a1-4-8)

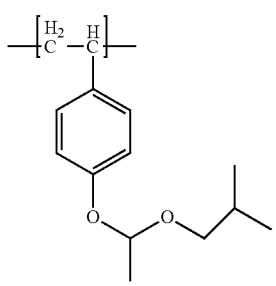

When the resin (A) has the structural unit (a1-4), the proportion thereof is preferably 5% by mole to 60% by mole, more preferably 5% by mole to 50% by mole, and still more preferably 10% by mole to 40% by mole, based on the all the structural units of the resin (A) (100% by mole).

Examples of the structural unit having an acid-labile group represented by formula (2) include one represented by formula (a1-5)

(a1-5)

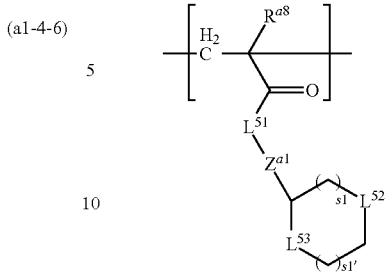

In formula (a1-5), $R^{a8}$ represents a hydrogen atom, a halogen atom, or a C1-C6 alkyl group which may have a halogen atom, $Z^{a1}$ represents a single bond or *—$(CH_2)_{h3}$—CO-$L^{54}$- in which h3 represents an integer of 1 to 4 and * represents a binding position to $L^{51}$, $L^{51}$, $L^{52}$, $L^{53}$ and $L^{54}$ each independently represent an oxygen atom or a sulfur atom, and s1 represents an integer of 1 to 3, and s1' represents an integer of 0 to 3.

Herein, the structural unit represented by formula (a1-5) is sometimes referred to as "structural unit (a1-5)".

Examples of halogen atoms include a fluorine atom and chlorine atom, preferably a fluorine atom.

Examples of the alkyl group which may have a halogen atom include a methyl group, an ethyl group, n-propyl group, an isopropyl group, n-butyl group, sec-butyl group, tert-butyl group, a pentyl group, a hexyl group, a heptyl group, a 2-ethylhexyl group, an octyl group, a fluoromethyl group, and a trifluoromethyl group.

In the formula (a1-5), $R^{a8}$ preferably represents a hydrogen atom, a methyl group, or trifluoromethyl group.

$L^{51}$ represents preferably an oxygen atom.

It is preferred that one of $L^{52}$ and $L^{53}$ represents an oxygen atom, while the other represents a sulfur atom.

s1 preferably represents 1. s1' represents an integer of 0 to 2.

$Z^{a1}$ preferably represents a single bond or *—$CH_2$—CO—O— wherein * represents a binding position to $L^{51}$.

Examples of the structural unit (a1-5) include one derived from monomer mentioned in JP2010-61117A1, which preferably include the following ones.

(a1-5-1)

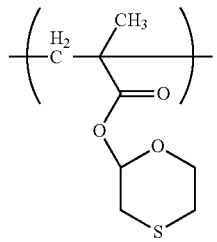

(a1-5-2)

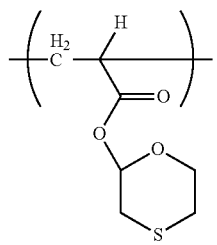

-continued

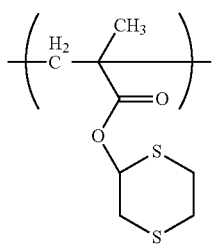

(a1-5-3)

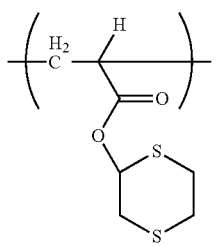

(a1-5-4)

Among them, the structural units represented by the formula (a1-5-1) and (a1-5-2) are more preferred.

When Resin (A) has a structural unit (a1-5), its content is usually 1 to 50% by mole, preferably 3 to 45% by mole and more preferably 5 to 40% by mole, and still more preferably 5 to 30% by mole, based on 100% by mole of all the structural units of the resin.

Another example of the structural unit (a1) includes one represented by formula (a1-0X) which is sometimes referred to as "the structural unit (a1-0X)".

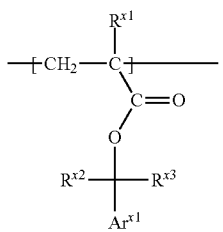

(a1-0X)

In the formula, $R^{x1}$ represents a hydrogen atom, a methyl group or an ethyl group, $R^{x2}$ and $R^{x3}$ each independently represent a C1-C6 saturated hydrocarbon group, and $Ar^{x1}$ represents a C6-C36 aromatic hydrocarbon group.

Resin (A) may comprise two or more of such structural units.

For $R^{x2}$ and $R^{x3}$, examples of the saturated hydrocarbon group include an alkyl group, an alicyclic hydrocarbon group and a group formed by combining them.

Examples of the alkyl group include a methyl group, an ethyl group, an n-propyl group, an isopropyl group, an n-butyl group, a sec-butyl group, a tert-butyl group, a pentyl group and a hexyl group.

The alicyclic hydrocarbon group may be monocyclic or polycyclic, and examples of the monocyclic alicyclic hydrocarbon group include a cyclopropyl group, a cyclobutyl group, a cyclopentyl group, and a cyclohexyl group.

For $Ar^{x1}$, examples of the aromatic hydrocarbon group include a C6-C36 aryl group such as a phenyl group, a naphthyl group and an anthryl group.

The aromatic hydrocarbon group has preferably 6 to 24 carbon atoms, more preferably 6 to 18 carbon atoms, and still more preferably a phenyl group.

$Ar^{x1}$ is preferably a C6-C36 aromatic hydrocarbon group, more preferably a phenyl group or a naphthyl group, and still more preferably a phenyl group.

Preferably, $R^{x1}$, $R^{x2}$ and $R^{x3}$ is each independently a methyl group or an ethyl group. More preferably, $R^{x1}$, $R^{x2}$ and $R^{x3}$ is a methyl group.

Examples of the structural unit (a1-0X) include the following ones and those represented by the following formulae in which a methyl group represented by $R^{x1}$ has been replaced by a hydrogen atom, and more preferably the structural units represented by formula (a1-0X-1) to formula (a1-0X-3).

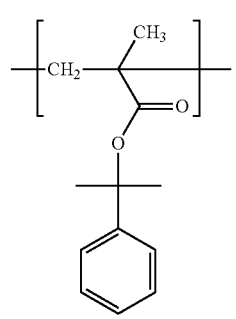

(a1-0X-1)

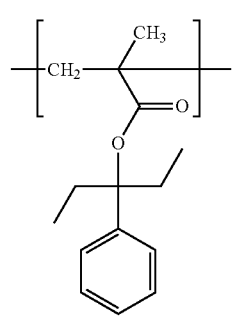

(a1-0X-2)

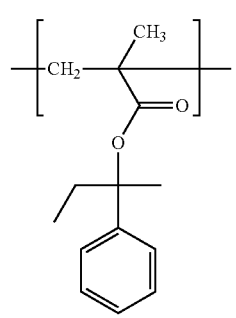

(a1-0X-3)

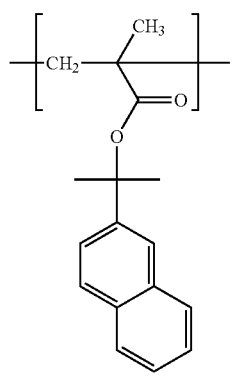
(a1-0X-4)
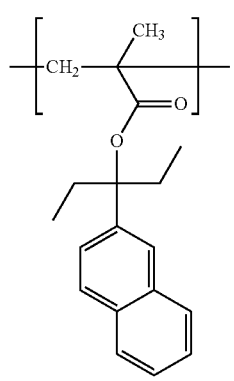
(a1-0X-5)
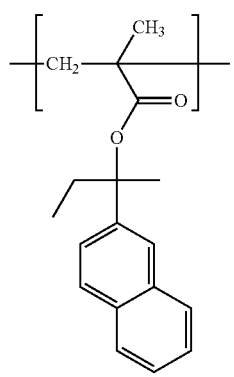
(a1-0X-6)
When Resin (A) has a structural unit (a1-0X), its content is usually 5 to 60% by mole, preferably 5 to 50% by mole, and more preferably 10 to 40% by mole, based on 100% by mole of all the structural units of the resin.
Another example of the structural unit (a1) further includes the following ones.
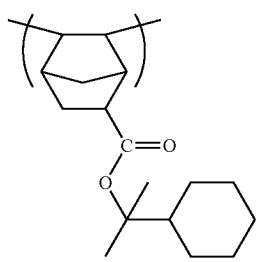
(a1-3-1)
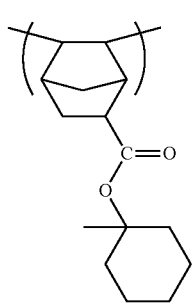
(a1-3-2)
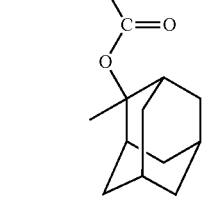
(a1-3-3)
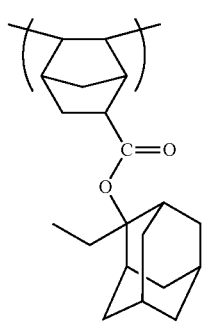
(a1-3-4)
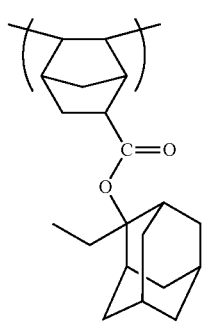
(a1-3-5)
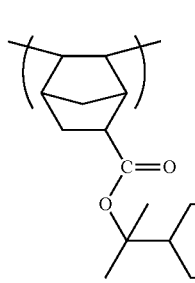
(a1-3-6)

-continued

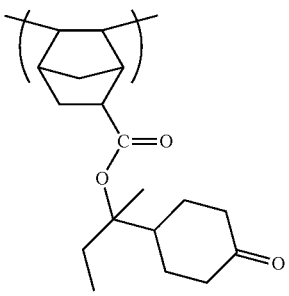

(a1-3-7)

When Resin (A) has any one of these structural units, its content is usually 5 to 60% by mole, preferably 5 to 50% by mole, more preferably 10 to 40% by mole, based on 100% by mole of all the structural units of the resin.

The structural unit (s) is derived from a monomer having no acid-labile group.

The structural unit (s) preferably has a hydroxy group or a lactone ring.

Hereinafter, the structural unit (s) having a hydroxy group is referred to as "structural unit (a2)", and the structural unit (s) having a lactone ring is referred to as "structural unit (a3)".

The hydroxy group which the structural unit (a2) has may be an alcoholic hydroxy group or a phenolic hydroxy group.

When KrF excimer laser (wavelength: 248 nm) lithography system, or a high energy laser such as electron beam and extreme ultraviolet issued as an exposure system, the resin which comprises the structural unit (a2) having a phenolic hydroxy group is preferred. When ArF excimer laser (wavelength: 193 nm) is used as an exposure system, the resin which comprises the structural unit (a2) having an alcoholic hydroxy group is preferred and the resin which comprises the structural unit (a2-1) described later is more preferred.

Resin (A) may have two or more of the structural units (a2). Examples of the structural unit (a2) having a phenolic hydroxy group include one represented by formula (a2-A):

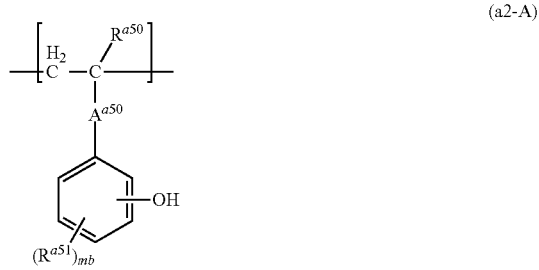

(a2-A)

In formula (a2-A), $R^{a50}$ represents a hydrogen atom, a halogen atom, a C1-C6 alkyl group or a C1-C6 halogenated alkyl group, $A^{a50}$ represents a single bond or *—$X^{a51}$-($A^{a52}$-$X^{a52}$)$_{nb}$, where * represents a binding position to the carbon atom bonded to $R^{a50}$, $A^{a52}$ represents a C1-C6 alkanediyl group, $X^{a51}$ and $X^{a52}$ represents —O—, —CO—O—, or —O—CO—, and nb represents an integer of 0 or 1, $R^{a51}$ is independently in each occurrence a halogen atom, a hydroxy group, a C1-C6 alkyl group, a C1-C6 alkoxy group, a C2-C4 acyl group, a C2-C4 acyloxy group, an acryloyl group or a methacryloyl group, and mb represents an integer of 0 to 4.

In the formula (a2-A), examples of the halogen atom include a fluorine atom, a chlorine atom, a bromine atom or iodine atom, examples of the C1-C6 alkyl group include a methyl group, an ethyl group, a propyl group, an isopropyl group, a butyl group, an isobutyl group, a sec-butyl group, a tert-butyl group, a pentyl group and a hexyl group, and a C1-C4 alkyl group is preferred and a C1-C2 alkyl group is more preferred and a methyl group is especially preferred.

Examples of the C1-C6 halogenated alkyl group include a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group and a perfluorohexyl group.

Examples of the C1-C6 alkoxy group include a methoxy group, an ethoxy group, a propoxy group, an isopropoxy group, a butoxy group, an isobutoxy group, a sec-butoxy group, a tert-butoxy group, a pentyloxy group and a hexyloxy group, and a C1-C4 alkoxy group is preferred and a C1-C2 alkoxy group is more preferred and a methoxy group is especially preferred.

Examples of the C2-C4 acyl group include an acetyl group, a propionyl group and a butyryl group, and examples of the C2-C4 acyloxy group include an acetyloxy group, a propionyloxy group and a butyryloxy group.

$R^{a51}$ is preferably a methyl group.

$R^{a50}$ is preferably a hydrogen atom and a C1-C4 alkyl group, more preferably a hydrogen atom, a methyl group and an ethyl group, and still more preferably a hydrogen atom and a methyl group.

As to $A^{a50}$, examples of *—$X^{a51}$-($A^{a52}$-$X^{a52}$)$_{nb}$— include *—O—, *—CO—O—, *—O—CO—, *—CO—O-$A^{a52}$-CO—O—, *—O—CO-$A^{a52}$-O—, *—O-$A^{a52}$-CO—O—, *—CO—O-$A^{a52}$-O—CO—, *—O—CO-$A^{a52}$-O—CO—, preferably *—CO—O—, *—CO—O-$A^{a52}$-CO—O— and *—O-$A^{a52}$-CO—O—.

As to $A^{a52}$, examples of the alkanediyl group include an ethylene group, a propane-1,3-diyl group, a propane-1,2-diyl group, a butane-1,4-diyl group, a pentane-1,5-diyl group, a hexane-1,6-diyl group, a butane-1,3-diyl group, a 2-methylpropane-1,3-diyl group, a 2-methylpropane-1,2-diyl group, a pentane-1,4-diyl group and a 2-methylbutane-1,4-diyl group.

$A^{a50}$ is preferably a single bond, *—CO—O— or *—CO—O-$A^{a52}$-O—CO—, more preferably a single bond, *—CO—O— or *—CO—O—$CH_2$—O—CO—, and still more preferably a single bond or *—CO—O—.

In the formula (a2-A), mb is preferably 0, 1 or 2, and is more preferably 0 or 1, and especially preferably 0.

In formula (a2-A), a hydroxyl group on the phenyl group is positioned preferably on o-position or p-position, and more preferably on p-position.

Examples of the structural unit (a2) include those derived from the monomers described in JP2010-204634A1 and JP2012-12577A1.

Preferred examples of the structural unit (a2) include the structural units represented by formulae (a2-2-1) to (a2-2-4) and those represented by formulae in which a methyl group corresponding to $R^{a50}$ has been replaced by a hydrogen atom.

Among them, the structural units represented by formulae (a2-2-1) and (a2-2-3) and those represented by formulae in which a methyl group corresponding to $R^{a50}$ has been replaced by a hydrogen atom are more preferred.

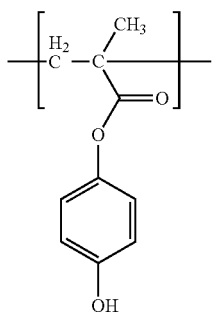
(a2-2-1)

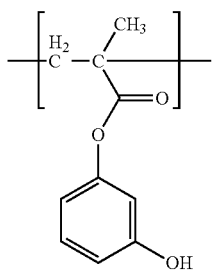
(a2-2-2)

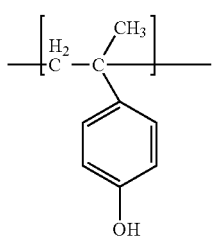
(a2-2-3)

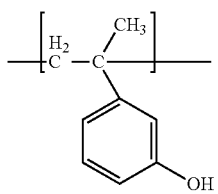
(a2-2-4)

When Resin (A) has the structural unit represented by formula (a2-A), its content is usually 5 to 80% by mole and preferably 10 to 70% by mole, more preferably 15 to 65% by mole, and still more preferably 20 to 65% by mole, based on the sum of the structural units of the resin.

Examples of the structural unit (a2) having an alcoholic hydroxy group include one represented by formula (a2-1):

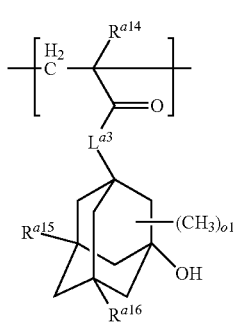
(a2-1)

wherein $R^{a14}$ represents a hydrogen atom or a methyl group, $R^{a15}$ and $R^{a16}$ each independently represent a hydrogen atom, a methyl group or a hydroxy group, $L^{a3}$ represents *—O— or *—O—$(CH_2)_{k2}$—CO—O— in which * represents a binding position to —CO—, and k2 represents an integer of 1 to 7, and o1 represents an integer of 0 to 10.

Hereinafter, the structural unit represented by formula (a2-1) is referred to as "structural unit (a2-1)".

In the formula (a2-1), $R^{a14}$ is preferably a methyl group. $R^{a15}$ is preferably a hydrogen atom. $R^{a16}$ is preferably a hydrogen atom or a hydroxy group. $L^{a3}$ is preferably *—O— or *—O—$(CH_2)_{f2}$—CO—O— in which * represents a binding position to —CO—, and f2 represents an integer of 1 to 4, is more preferably *—O— and *—O—$CH_2$—CO—O—, and is still more preferably *—O—, and o1 is preferably 0, 1, 2 or 3 and is more preferably 0 or 1.

Examples of monomers from which the structural unit (a2-1) is derived include compounds mentioned in JP2010-204646A.

Preferred examples of the structural unit (a2-1) include those represented by formulae (a2-1-1) to (a2-1-6).

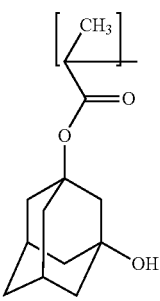
(a2-1-1)

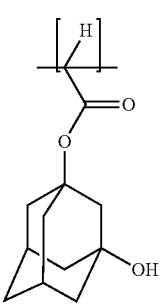
(a2-1-2)

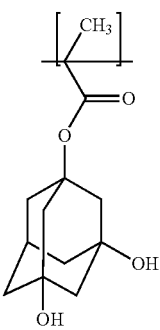
(a2-1-3)

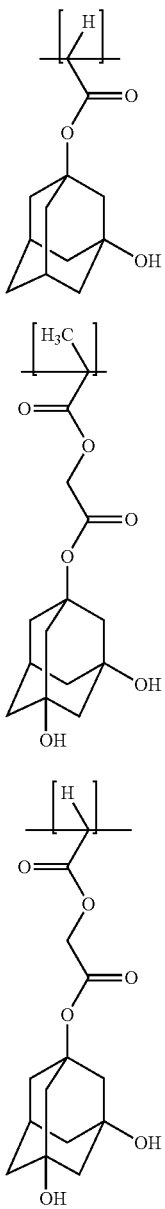

(a2-1-4)

(a2-1-5)

(a2-1-6)

(a3-1)

(a3-2)

(a3-3)

(a3-4)

Among them, more preferred are the structural units represented by formulae (a2-1-1), (a2-1-2), (a2-1-3) and (a2-1-4), still more preferred are the structural units represented by formulae (a2-1-1) and (a2-1-3).

When Resin (A) has the structural unit (a2-1), its content is usually 1 to 45% by mole, preferably 1 to 40% by mole, and more preferably 1 to 35% by mole, still more preferably 2 to 20% by mole, further still more preferably 2 to 10% by mole, based on the sum of the structural units of the resin.

Examples of the lactone ring for the structural unit (a3) include a monocyclic lactone ring such as β-propiolactone ring, γ-butyrolactone ring and γ-valerolactone ring, and a condensed ring formed from a monocyclic lactone ring and the other ring. Among them, preferred are γ-butyrolactone ring and a condensed lactone ring formed from γ-butyrolactone ring and the other ring.

Preferred examples of the structural unit (a3) include those represented by formulae (a3-1), (a3-2), (a3-3) and (a3-4).

In formulae, $L^{a4}$, $L^{a5}$ and $L^{a6}$ each independently represent *—O— or *—O—$(CH_2)_{k3}$—CO—O— in which * represents a binding position to a carbonyl group and k3 represents an integer of 1 to 7, $R^{a18}$, $R^{a19}$ and $R^{a20}$ each independently represent a hydrogen atom or a methyl group, $R^{a21}$ represents a C1-C4 monovalent aliphatic hydrocarbon group, $R^{a24}$ represents a hydrogen atom, a halogen atom, or a C1-C6 alkyl group which may have a halogen atom, $R^{a22}$, $R^{a23}$ and $R^{25}$ each independently represent a carboxy group, a cyano group, or a C1-C4 aliphatic hydrocarbon group, $L^{a7}$ represents an oxygen atom, $*^1$—O-$L^{a8}$-O—, $*^1$—O-$L^{a8}$-CO—O—, $*^1$—O-$L^{a8}$-CO—O-$L^{a9}$-CO—O— or $*^1$—O-$L^{a8}$-CO—O-$L^{a9}$-O— in which $L^{a8}$ and $L^{a9}$ each independently represent C1-C6 divalent alkanediyl group, $*^1$ represents a binding position to a carbonyl group, p1 represents an integer of 0 to 5,
q1 and r1 independently each represent an integer of 0 to 3, and
w1 represents an integer of 0 to 8.

Examples of the aliphatic hydrocarbon group represented by $R^{a21}$, $R^{a22}$, $R^{a23}$ and $R^{a25}$ include alkyl groups such as a methyl group, an ethyl group, a propyl group, or a butyl group.

Examples of the alkyl group represented by $R^{a24}$ include a methyl group, an ethyl group, a propyl group, a butyl group, a pentyl group, and a hexyl group, preferably a C1-C4 alkyl group, and more preferably a methyl group and an ethyl group.

Examples of halogen atom represented by $R^{a24}$ include a fluorine atom, a chlorine atom, a bromine atom and an iodine atom.

As to $R^{a24}$, examples of the alkyl group which has an halogen atom include a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group, a perfluorohexyl group, a trichloromethyl group, a tribromomethyl group, and a triiodomethyl group.

As to $L^{a8}$ and $L^{a9}$, examples of the alkanediyl group include a methylene group, an ethylene group, a propane-1,3-diyl group, a butane-1,4-diyl group, a pentane-1,5-diyl group and a hexane-1,6-diyl group, a butane-1,3-diyl group, 2-methylpropane-1,3-diyl group, a 2-methylpropane-1,2-diyl group, a pentane-1,4-diyl group and a 2-methylbutane-1,4-diyl group.

Preferably, $L^{a4}$, $L^{a5}$ and $L^{a6}$ each independently represent *—O— or *—O—$(CH_2)_{d1}$—CO—O— in which * represents a binding position to —CO— and d1 represents an integer of 1 to 4. More preferably, $L^{a4}$, $L^{a5}$ and $L^{a6}$ are *—O— and *—O—$CH_2$—CO—O—, and still more preferably $L^{a4}$, $L^{a5}$ and $L^{a6}$ are *—O—.

$R^{a18}$, $R^{a19}$ and $R^{a20}$ are preferably methyl groups. $R^{a21}$ is preferably a methyl group. Preferably, $R^{a22}$ and $R^{a23}$ are independently in each occurrence a carboxyl group, a cyano group or a methyl group.

Preferably, p1, q1 and r1 each independently represent an integer of 0 to 2, and more preferably p1, q1 and r1 each independently represent 0 or 1.

$R^{a24}$ is preferably a hydrogen atom or a C1-C4 alkyl group, more preferably a hydrogen atom, a methyl group or an ethyl group, and still more preferably a hydrogen atom or a methyl group.

$L^{a7}$ represents preferably an oxygen atom or $*^1$—O-$L^{a8}$-CO—O—, more preferably an oxygen atom, $*^1$—O—$CH_2$—CO—O— or $*^1$—O—$C_2H_4$—CO—O—.

The formula (a3-4)' is preferably one.

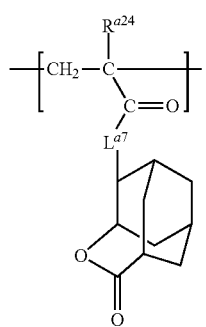

(a3-4)'

In the formula, $R^{a24}$ and $L^{a7}$ are as defined above, respectively.

Examples of the monomer from which the structural unit (a3) is derived include those mentioned in US2010/203446A1, US2002/098441A1 and US2013/143157A1.

Examples of the structural unit (a3) include the following ones.

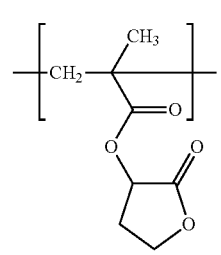

(a3-1-1)

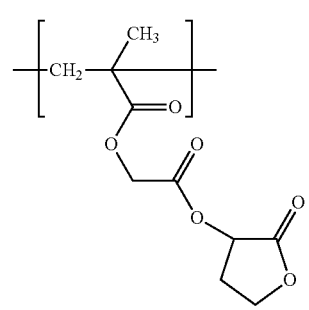

(a3-1-2)

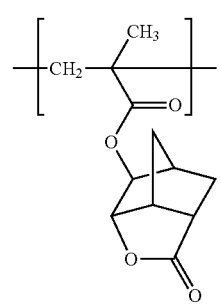

(a3-2-1)

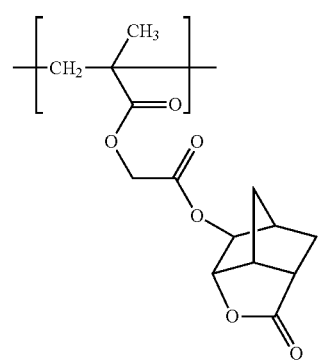

(a3-2-2)

(a3-3-1) 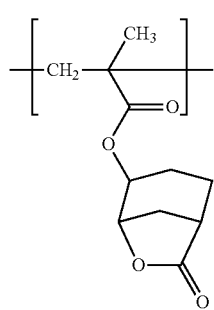
(a3-3-2) 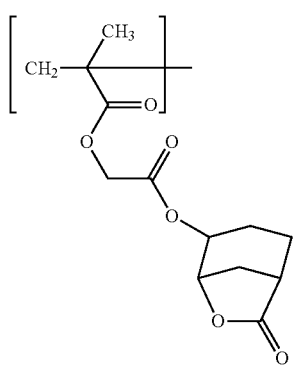
(a3-4-1) 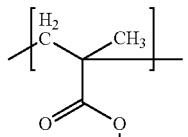
(a3-4-2) 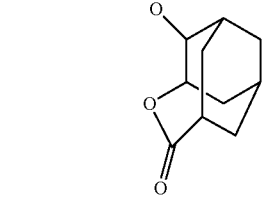
(a3-4-3) 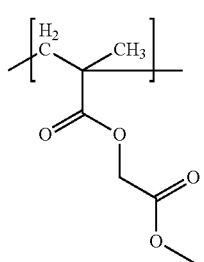
(a3-4-4) 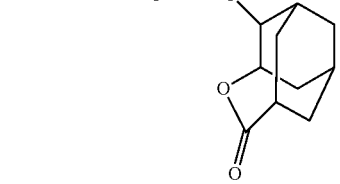
(a3-4-5) 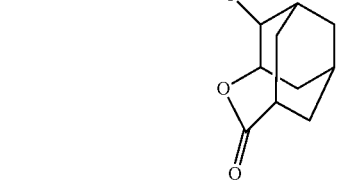

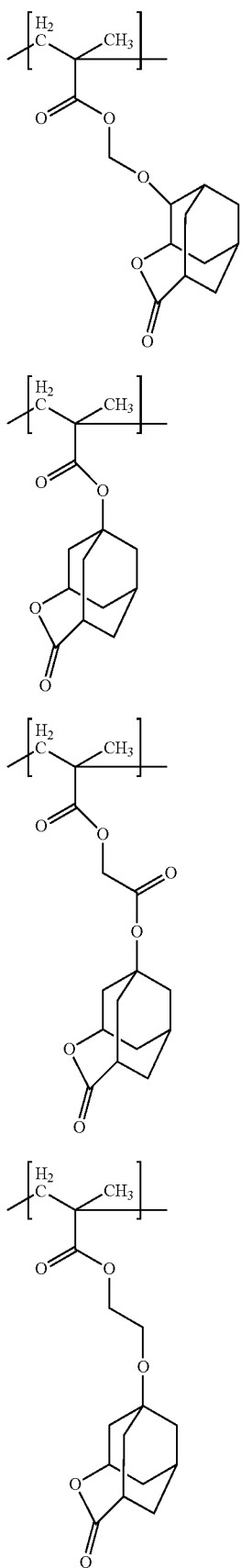
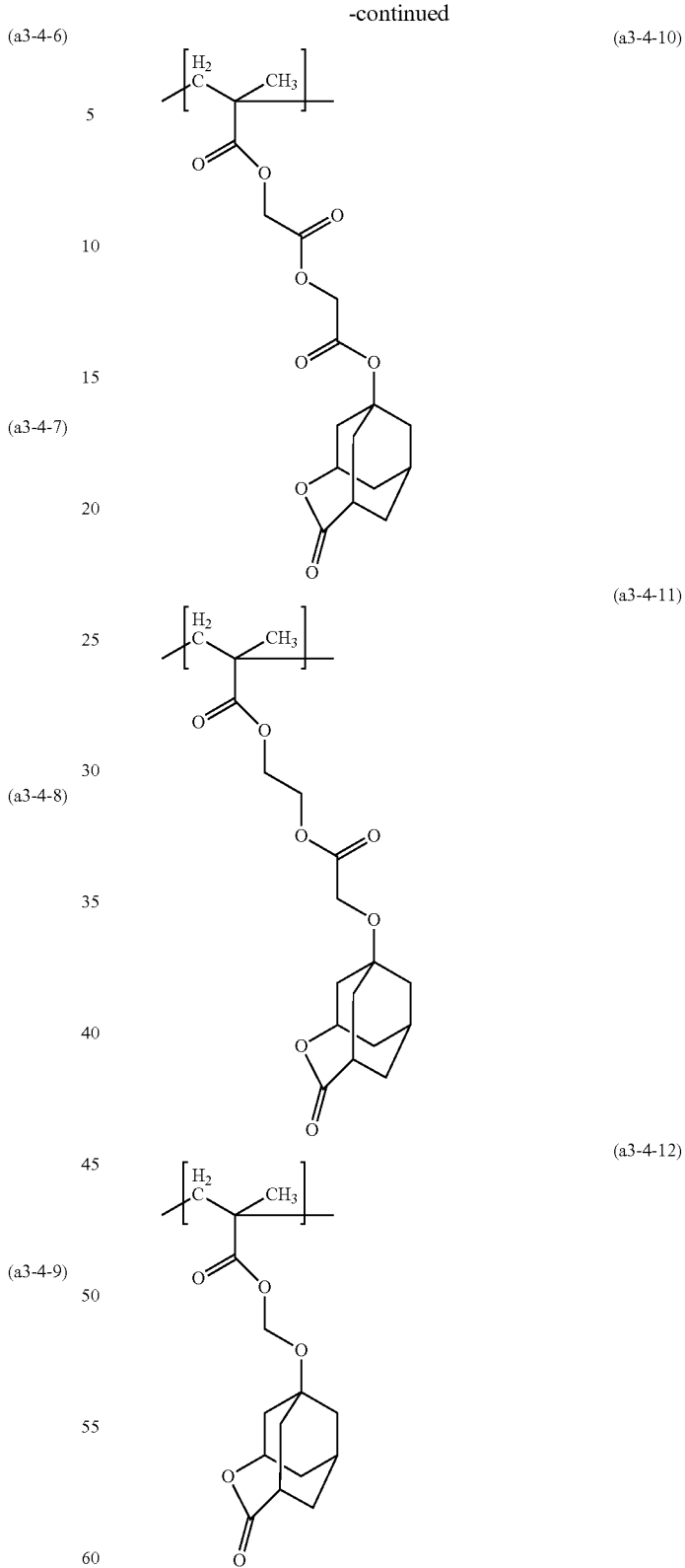
Other examples of the structural unit (a3) include those represented by formulae (a3-1) to (a3-4) in which the methyl group corresponding to $R^{a18}$, $R^{a19}$, $R^{a20}$ and $R^{a24}$ of formulae (a3-1) to (a3-4) has been replaced by a hydrogen atom.

When Resin (A) has the structural unit (a3), its content thereof is preferably 5 to 70% by mole, and more preferably 10 to 65% by mole and more preferably 10 to 60% by mole, based on the sum of the structural units of the resin.

When Resin (A) has the structural unit (a3-1), (a3-2), (a3-3) or (a3-4), its content thereof is preferably 5 to 60% by mole, and more preferably 5 to 50% by mole and more preferably 10 to 50% by mole, based on the sum of the structural units of the resin.

Other examples of the structural unit (s) include a structural unit having a fluorine atom and a structural unit which has a hydrocarbon not being removed therefrom by action of an acid.

Hereinafter, the structural unit (s) having a halogen atom is referred to as "structural unit (a4)".

Halogen atoms for the structural unit (a4) may be a fluorine atom, a chlorine atom, a bromine atom, or an iodine atom. The structural unit (a4) has preferably a fluorine atom.

Examples of the structural unit (a4) include the following one.

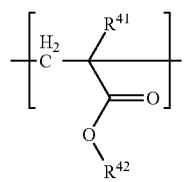

(a4)

In the formula, $R^{41}$ represents a hydrogen atom or a methyl group, $R^{42}$ represents a C1-C24 saturated hydrocarbon group having a fluorine atom in which hydrocarbon group a methylene group can be replaced by an oxygen atom or a carbonyl group.

Examples of the saturated hydrocarbon group include C1-C24 chain hydrocarbon group, an alicyclic hydrocarbon group including a monocyclic or polycyclic hydrocarbon group, and any combinations of these groups.

Examples of the chain hydrocarbon group include a methyl group, an ethyl group, a propyl group, a butyl group, a pentyl group, a hexyl group, a heptyl group, an octyl group, a decyl group, a dodecyl group, a pentadecyl group, a hexadecyl group, a heptadecyl group and an octadecyl group.

Examples of the alicyclic hydrocarbon group include a cyclopentyl group, a cyclohexyl group, a cycloheptyl group, and a cyclooctyl group, decahydronaphthyl group, an adamantyl group, a norbornyl group and the following groups:

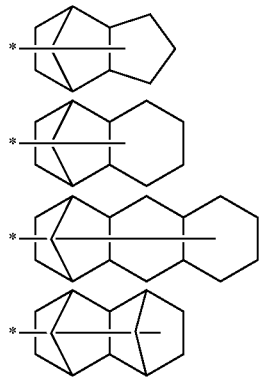

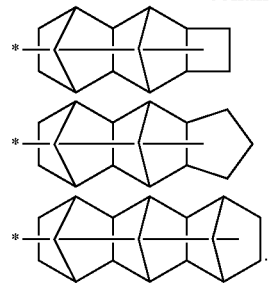

Examples of the combinations of these groups include any combination of an alkyl or alkanediyl group with an alicyclic hydrocarbon group, which specifically include -[alkanediyl group]-[alicyclic hydrocarbon group], -[alicyclic hydrocarbon group]-[alkyl group] and -[alkanediyl group]-[alicyclic hydrocarbon group]-[alkyl group].

Typical examples of the structural unit (a4) include structural units represented by formulae (a4-0), (a4-1), (a4-2), (a4-3) and (a4-4).

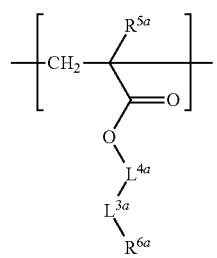

(a4-0)

In the formula (a4-0), $R^{5a}$ represents a hydrogen atom or a methyl group, $L^{4a}$ represents a single bond or a C1-C4 alkanediyl group, $L^{3a}$ represents a C1-C8 perfluoroalkanediyl group, or a C3-C12 perfluorocycloalkanediyl group, and $R^{6a}$ represents a hydrogen atom or a fluorine atom.

For $L^{4a}$, examples of the alkanediyl group include a linear alkanediyl group such as a methylene group, an ethylene group, a propane-1,3-diyl group, and butane-1,4-diyl group, and a branched alkanediyl group such as an ethane-1,1-diyl group, a propane-1,2-diyl group, a butane-1,3-diyl group, a 2-methylpropane-1,3-diyl group and 2-methylpropane-1,2-diyl group.

Examples of the perfluoroalkanediyl group for $L^{3a}$ include difluoromethylene, perfluoroethylene, perfluoropropane-1,1-diyl, perfluoropropane-1,2-diyl, perfluoropropane-2,2-diyl, perfluorobutane-1,4-diyl, perfluorobutane-2,2-diyl, perfluorobutane-1,2-diyl, perfluoropentane-1,5-diyl, perfluoropentane-2,2-diyl, perfluoropentane-3,3-diyl, perfluorohexane-1,6-diyl, perfluorohexane-2,2-diyl, perfluorohexane-3,3-diyl, perfluoroheptane-1,7-diyl, perfluoroheptane-2,2-diyl, perfluoroheptane-3,4-diyl, perfluoroheptane-4,4-diyl, perfluorooctan-1,8-diyl, perfluorooctan-2,2-diyl, perfluorooctan-3,3-diyl and perfluorooctan-4,4-diyl groups.

Examples of the perfluorocycloalkanediyl group for $L^{3a}$ include perfluorocyclohexanediyl, perfluorocyclopentanediyl, perfluorocycloheptanediyl and perfluoroadamantanediyl groups.

$L^{3a}$ is preferably a C1-C6 perfluoroalkanediyl group, more preferably a C1-C3 perfluoroalkanediyl group.

$L^{4a}$ is preferably a single bond, a methylene group or an ethylene group, more preferably a single bond or a methylene group.

Examples of the structural unit represented by formula (a4-0) include the structural units represented by the following formulae and those represented by the following formulae in which a methyl group has been replaced by a hydrogen atom.

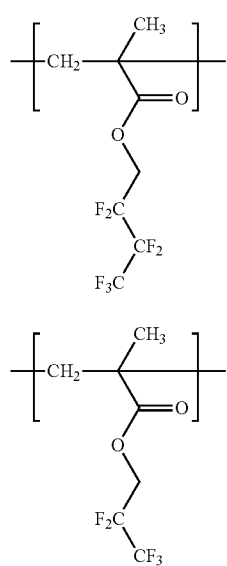
(a4-0-1)

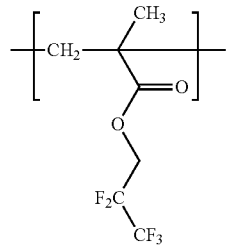
(a4-0-2)

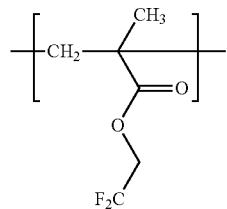
(a4-0-3)

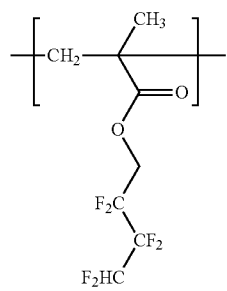
(a4-0-4)

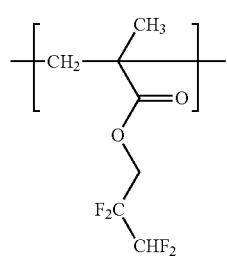
(a4-0-5)

-continued

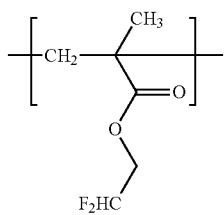
(a4-0-6)

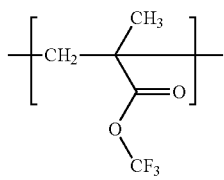
(a4-0-7)

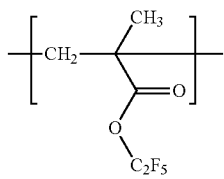
(a4-0-8)

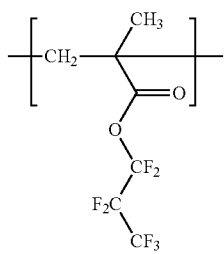
(a4-0-9)

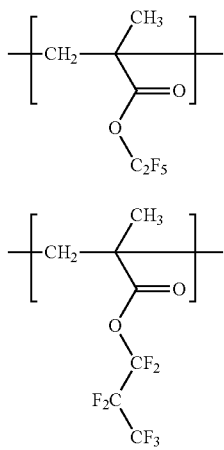
(a4-0-10)

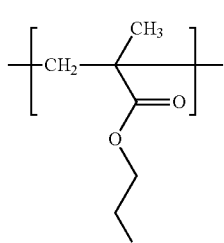
(a4-0-11)

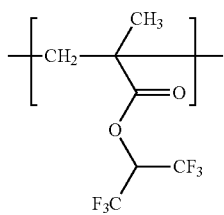
(a4-0-12)

-continued

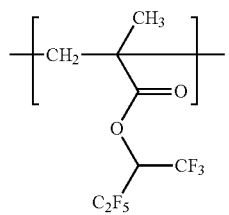
(a4-0-13)

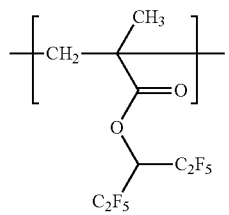
(a4-0-14)

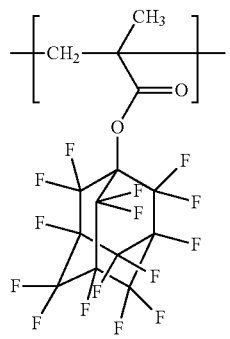
(a4-0-15)

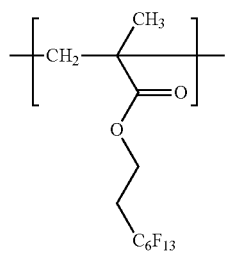
(a4-0-16)

The structural unit represented by formula (a4-1) is as follows.

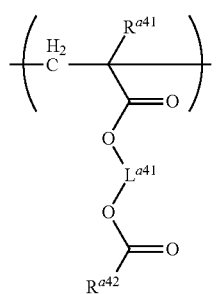
(a4-1)

In the formula, $R^{a41}$ represents a hydrogen atom or a methyl group;

$R^{a42}$ represents a C1-C20 saturated hydrocarbon group which may have a substituent and in which a methylene group can be replaced by an oxygen atom or a carbonyl group, provided that each or both of $A^{a41}$ and $R^{a42}$ have a fluorine atom; and $A^{a41}$ represents a C1-C6 alkanediyl group which may have a substituent or a moiety represented by formula (a-g1):

$$-A^{a42}\!-\!(\!X^{a41}\!-\!A^{a43}\!)_{s}\!-\!X^{a42}\!-\!A^{a44}\!- \tag{a-g1}$$

in which s represents an integer of 0 to 1, $A^{a42}$ and $A^{a44}$ respectively represent a C1-C5 saturated hydrocarbon group which may have a substituent, $A^{a43}$ represents a single bond or a C1-C5 aliphatic hydrocarbon group which may have a substituent, $X^{a41}$ and $X^{a42}$ respectively represent —O—, —CO—, —CO—O—, or —O—CO—, provided that the sum of carbon atoms of $A^{a42}$, $A^{a43}$, $A^{a44}$, $X^{a41}$ and $X^{a42}$ is 7 or less and $A^{44}$ is bonded to —O—CO—$R^{a42}$.

The saturated hydrocarbon group for $R^{a42}$ includes a chain saturated hydrocarbon group, an alicyclic hydrocarbon group including a monocyclic hydrocarbon group and a polycyclic hydrocarbon group, and any combination of these hydrocarbon groups.

Examples of the chain saturated hydrocarbon group include a methyl group, an ethyl group, a propyl group, a butyl group, a pentyl group, a hexyl group, a heptyl group, an octyl group, a decyl group, a dodecyl group, a hexadecyl group, a pentadecyl group, a hexyldecyl group, a heptadecyl group and an octadecyl group.

Examples of alicyclic hydrocarbon groups include cycloalkyl groups such as a cyclopentyl group, a cyclohexyl group, a cycloheptyl group and a cyclooctyl group; and monovalent polycyclic hydrocarbon groups such as a decahyrdonaphthyl group, an adamantyl group, a norbornyl group, and the following groups where * represents a binding position.

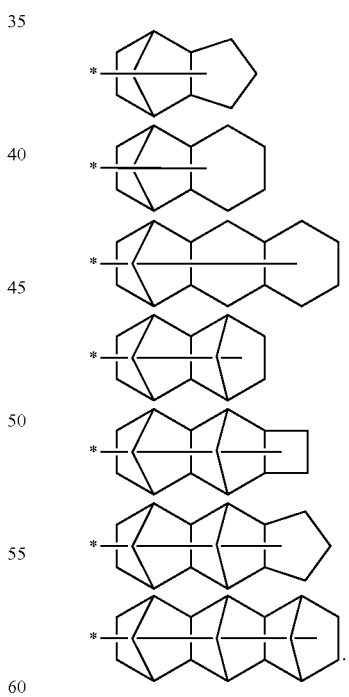

Examples of the combination of these groups include combination of an alkanediyl or alkyl group with an alicyclic hydrocarbon group such as -[alkanediyl group]-[alicyclic hydrocarbon group], -[alicyclic hydrocarbon group]-[alkyl group], and -[alkanediyl group]-[alicyclic hydrocarbon group]-[alkyl group].

The hydrocarbon group represented by $R^{a42}$ preferably has a substituent. Examples of the substituent include a halogen atom and a group represented by formula (a-g3):

$$—X^{a43}\text{-}A^{a45} \quad (a\text{-}g3)$$

in which $X^{a43}$ represents an oxygen atom, a carbonyl group, a carbonyloxy group or an oxycarbonyl group, and $A^{a45}$ represents a C1-C17 chain or alicyclic hydrocarbon group which may have a fluorine atom.

Examples of the chain or alicyclic hydrocarbon group for $A^{a45}$ include alkyl groups such as a methyl group, an ethyl group, a propyl group, a butyl group, a pentyl group, a hexyl group, a heptyl group, an octyl group, a decyl group, a dodecyl group, a hexadecyl group, a pentadecyl group, a hexyldecyl group, a heptadecyl group and an octadecyl group;

monocyclic alicyclic hydrocarbon groups such as a cyclopentyl group, a cyclohexyl group, a cycloheptyl group and a cyclooctyl group; and monovalent polycyclic hydrocarbon groups such as a decahyrdonaphthyl group, an adamantyl group, a norbornyl group, and the following groups where * represents a binding position.

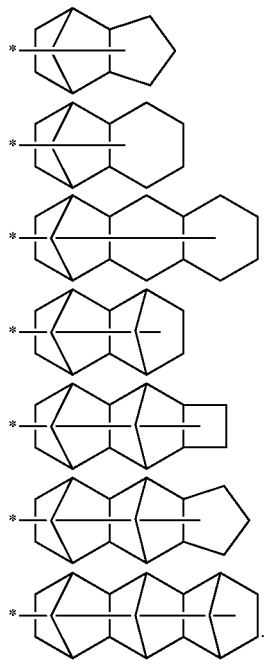

$R^{a42}$ is preferably a chain or alicyclic hydrocarbon group which may have a halogen atom, more preferably an alkyl group which has a halogen atom or a group represented by formula (a-g3).

If $R^{a42}$ is a chain or alicyclic hydrocarbon group which has a halogen atom, it is preferably a chain or alicyclic hydrocarbon group which has a fluorine atom, more preferably a perfluoroalkyl group or a perfluorocycloalkyl group, and still more preferably a C1-C6, especially C1-C3, perfluoroalkyl group.

Specific examples of the perfluoroalkyl group include a perfluoromethyl group, a perfluoroethyl group, a perfluoropropyl group, a perfluorobutyl group, a perfluoropentyl group, a perfluorohexyl group, a perfluoroheptyl group, and a perfluorooctyl group. Specific examples of the perfluorocycloalkyl group include a perfluorocyclohexyl group.

Examples of the substituents for $R^{a42}$ include a hydroxy group, a C1-C6 alkoxy group, and a halogen atom such as fluorine atom.

If $R^{a42}$ is a chain or alicyclic hydrocarbon group which has a group represented by formula (a-g3), $R^{a42}$ has preferably 15 or less carbon atoms, more preferably 12 or less carbon atoms.

If $R^{a42}$ has a group represented by formula (a-g3), $R^{a42}$ has preferably one group represented by formula (a-g3).

The chain or alicyclic hydrocarbon group which has a group represented by formula (a-g3) is preferably a group represented by formula (a-g2):

$$-A^{a46}\text{-}X^{a44}\text{-}A^{a47} \quad (a\text{-}g2)$$

in which $A^{a46}$ represents a C1-C17 chain or alicyclic hydrocarbon group which may have a fluorine atom, $X^{a44}$ represents a carbonyloxy group or an oxycarbonyl group, and $A^{a47}$ represents a C1-C17 chain or alicyclic hydrocarbon group which may have a fluorine atom, provided that $A^{a46}$, $A^{a47}$ and $X^{a44}$ have 18 or less of carbon atoms in total and one or both of $A^{a46}$ and $A^{a47}$ have a fluorine atom.

The chain or alicyclic hydrocarbon group represented by $A^{a46}$ has preferably 1 to 6, more preferably 1 to 3 carbon atoms.

The chain or alicyclic hydrocarbon group represented by $A^{a47}$ has preferably 4 to 15, more preferably 5 to 12 carbon atoms. $A^{a47}$ is more preferably a cyclohexyl group or an adamantyl group.

Examples of the group represented by formula (a-g2) include the following ones.

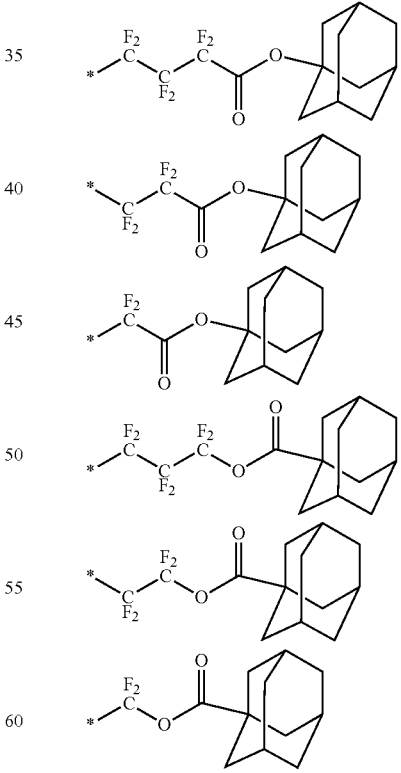

In each formula, * represents a binding position to a carboxy group.

Examples of $A^{a41}$ typically include a C1-C6 alkanediyl group which may be a linear chain or branched chain.

Specific examples of them include linear chain alkanediyl groups such as a methylene group, an ethylene group, a propane-1,3-diyl group, a butane-1,4-diyl group, a pentane-1,5-diyl group, or a hexane-1,6-diyl group; and branched chain alkanediyl groups such as a propane-1,3-diyl group, a butane-1,3-diyl group, a 1-methylbutane-1,2-diyl group, or a 2-methylbutane-1,4-diyl group. Examples of the substituents on the alkanediyl group include a hydroxy group or a C1-C6 alkoxy group.

$A^{a41}$ is preferably a C1-C4 alkanediyl group, more preferably a C2-C4 alkanediyl group, and still more preferably an ethylene group.

Examples of the alkanediyl group represented by $A^{a42}$, $A^{a43}$ and $A^{a44}$ include a methylene group, an ethylene group, a propane-1,3-diyl group, a butane-1,4-diyl group, a 2-methylpropane-1,3-diyl group, or a 2-methylbutane-1,4-diyl group. Examples of the substituents which such alkanediyl group may have include a hydroxy group or a C1-C6 alkoxy group.

$X^{a42}$ represents an oxygen atom, a carbonyl group, a carbonyloxy group or an oxycarbonyl group.

Examples of the moiety represented by formula (a-g1) where $X^{a42}$ is an oxygen atom, a carbonyl group, a carbonyloxy group or an oxycarbonyl group include the following ones:

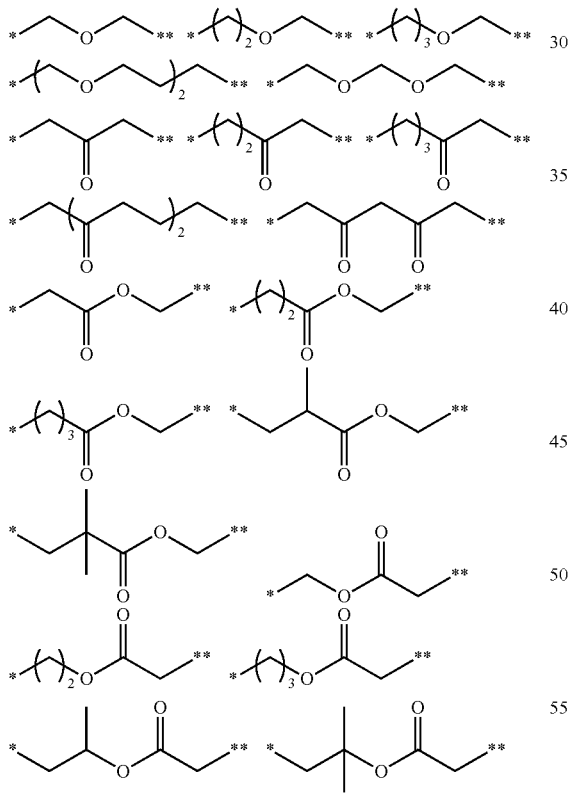

in which * and  represent binding positions, and  represents a binding position to —O—CO—$R^{a42}$.

Typical examples of the structural unit represented by formulae (a4-1) include the structural units represented by the following formulae and those represented by the following formulae in which a methyl group has been replaced by a hydrogen atom.

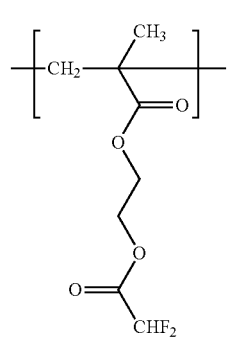
(a4-1-1)

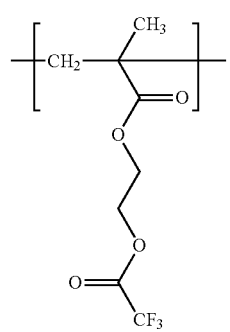
(a4-1-2)

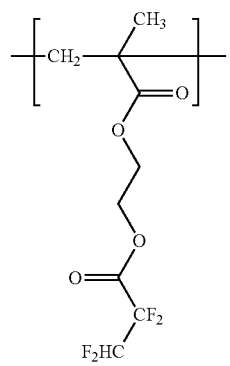
(a4-1-3)

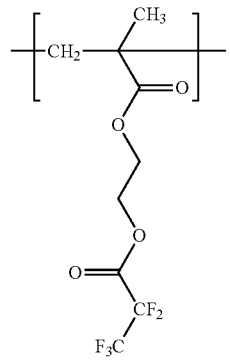
(a4-1-4)

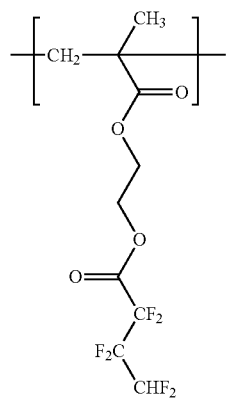 (a4-1-5)
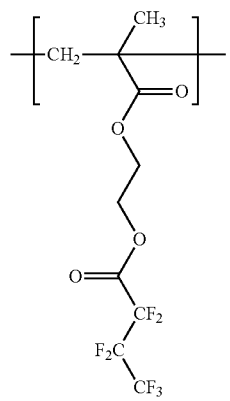 (a4-1-6)
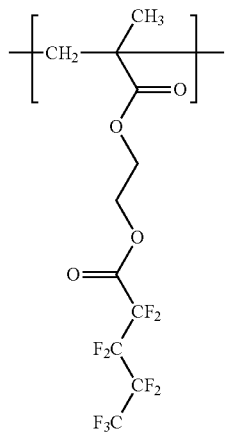 (a4-1-8)
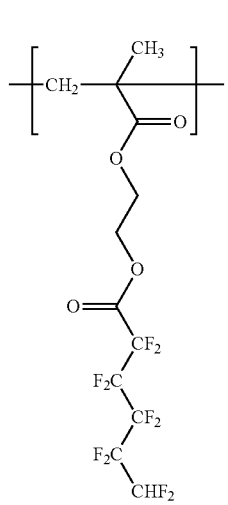 (a4-1-9)
(a4-1-7)
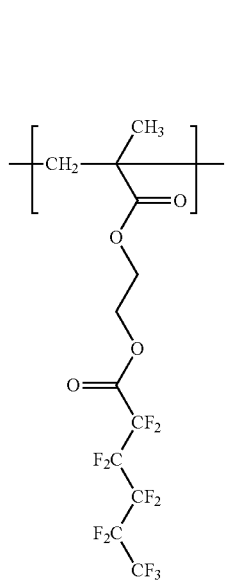 (a4-1-10)

(a4-1-11)
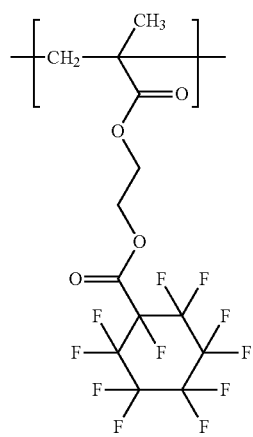
(a4-1'-1)
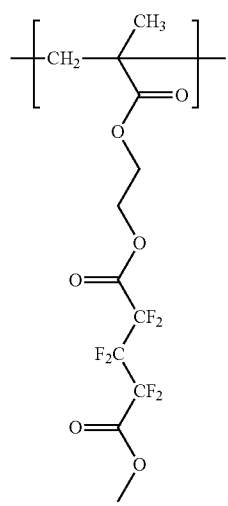
(a4-1'-3)
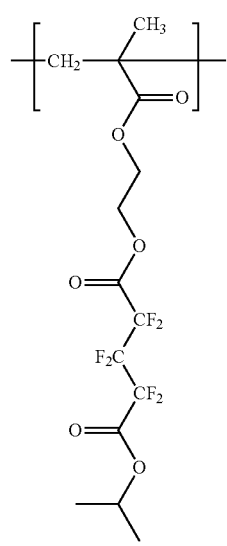
(a4-1'-4)
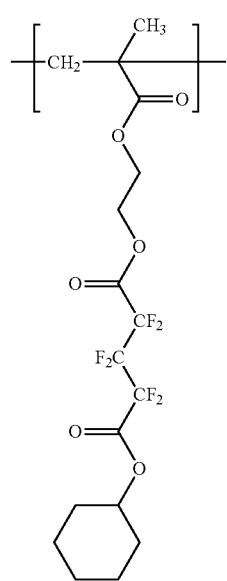

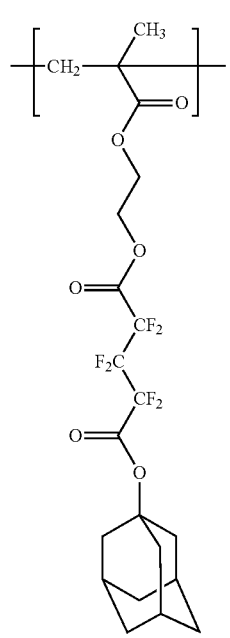 (a4-1'-5)
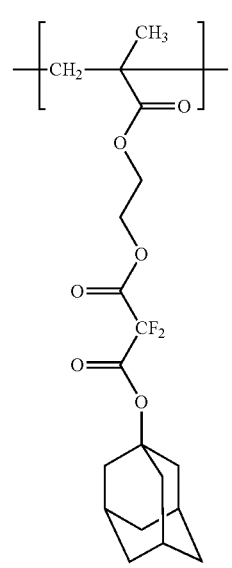 (a4-1'-7)
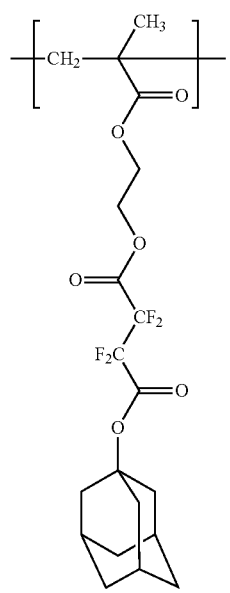 (a4-1'-6)
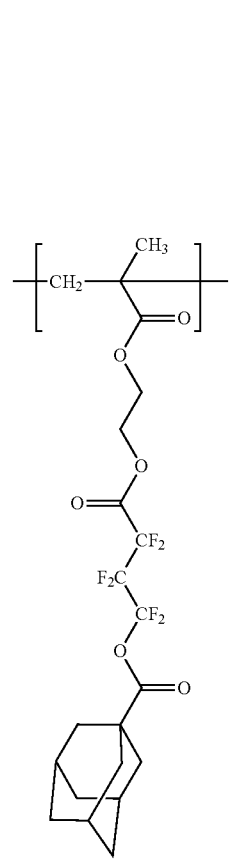 (a4-1'-8)

The structural unit represented by the formula (a4) is typically a structural unit represented by formula (a4-2):

$$\text{(a4-2)}$$

wherein $R^{f5}$ represents a hydrogen atom or a methyl group,
$L^{44}$ represent a C1-C18 alkanediyl group in which a methylene group can be replaced by —O— or —CO—, and
$R^{f6}$ represents a C1-C20 saturated hydrocarbon group that has a fluorine atom, provided that $L^{44}$ and $R^{f6}$ have 2 to 21 carbon atoms in total.

Examples of the alkanediyl group for $L^{44}$ include a linear alkanediyl group such as methylene, ethylene, propane-1,3-diyl, propane-1,2-diyl, butane-1,4-diyl, pentane-1,5-diyl and hexane-1,6-diyl groups; and a branched alkanediyl group such as 1-methylpropane-1,3-diyl, 2-methylpropane-1,3-diyl, 2-methylpropane-1,2-diyl, 1-methylbutane-1,4-diyl and 2-methylbutane-1,4-diyl groups.

Examples of the saturated hydrocarbon group for $R^{f6}$ include an aliphatic hydrocarbon group and an aromatic hydrocarbon group. The aliphatic hydrocarbon group includes chain and cyclic groups, and a combination thereof. The aliphatic hydrocarbon group is preferably an alkyl group and a cyclic aliphatic hydrocarbon group. Examples of the alkyl group include methyl, ethyl, n-propyl, isopropyl, n-butyl, sec-butyl, tert-butyl, n-pentyl, n-hexyl, n-heptyl, n-octyl and 2-ethylhexyl groups.

Examples of the cyclic aliphatic hydrocarbon group include any of a monocyclic group and a polycyclic group. Examples of the monocyclic alicyclic hydrocarbon group include a cycloalkyl group such as cyclopropyl, cyclobutyl, cyclopentyl, cyclohexyl, methylcyclohexyl, dimethylcyclohexyl, cycloheptyl, cyclooctyl, and cyclodecyl groups. Examples of the polycyclic hydrocarbon groups include decahydronaphthyl, adamantyl, 2-alkyladamantane-2-yl, 1-(adamantane-1-yl)alkane-1-yl, norbornyl, methylnorbornyl and isobornyl groups.

Examples of the saturated hydrocarbon group having a fluorine atom for $R^{f6}$ include an alkyl group having a fluorine atom and an alicyclic hydrocarbon group having a fluorine atom.

Specific examples of an alkyl group having a fluorine atom include a fluorinated alkyl group such as difluoromethyl, trifluoromethyl, 1,1-difluoroethyl, 2,2-difluoroethyl, 2,2,2-trifluoroethyl, perfluoroethyl, 1,1,2,2-tetrafluoropropyl, 1,1,2,2,3,3-hexafluoropropyl, perfluoroethylmethyl, 1-(trifluoromethyl)-1,2,2,2-tetrafluoroethyl, perfluoropropyl, 1-(trifluoromethyl)-2,2,2-trifluoroethyl, 1,1,2,2-tetrafluorobutyl, 1,1,2,2,3,3-hexafluorobutyl, 1,1,2,2,3,3,4,4-octafluorobutyl, perfluorobutyl, 1,1-bis(trifluoro)methyl-2,2,2-trifluoroethyl, 2-(perfluoropropyl)ethyl, 1,1,2,2,3,3,4,4-octafluoropentyl, perfluoropentyl, 1,1,2,2,3,3,4,4,5,5-decafluoropentyl, 1,1-bis(trifluoromethyl)-2,2,3,3,3-pentafluoropropyl, 2-(perfluorobutyl)ethyl, 1,1,2,2,3,3,4,4, 5,5-decafluorohexyl, 1,1,2,2,3,3,4,4,5,5,6,6-dodeca fluorohexyl, perfluoropentylmethyl and perfluorohexyl groups.

Examples of the alicyclic hydrocarbon group having a fluorine atom include a fluorinated cycloalkyl group such as perfluorocyclohexyl and perfluoroadamantyl groups.

In the formula (a4-2), $L^{44}$ is preferably a C2-C4 alkanediyl group, and more preferably an ethylene group.

$R'^6$ is preferably a C1-C6 fluorinated alkyl group.

Examples of the structural unit represented by formula (a4-2) include ones represented by formulae (a4-1-1) to (a4-1-11) and those in which a methyl group represented by $R'^5$ has been replaced by a hydrogen atom.

Another typical example of the structural unit represented by the formula (a4) includes one represented by formula (a4-3).

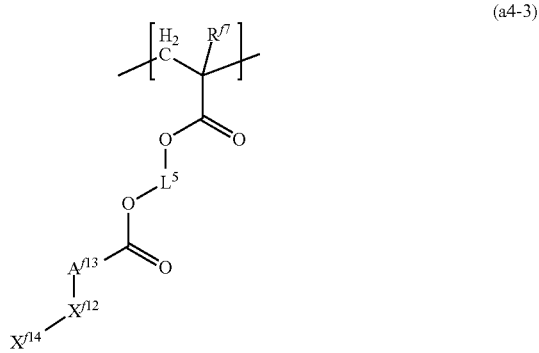

(a4-3)

In formula, $R^{17}$ represents a hydrogen atom or a methyl group.

$L^5$ represents a C1-C6 alkanediyl group.

$A'^{13}$ represents a C1-C18 saturated hydrocarbon group which may have a fluorine atom.

$X'^{12}$ represents a carbonyloxy group or an oxycarbonyl group.

$A'^{14}$ represents a C1-C17 saturated hydrocarbon group which may have a fluorine atom, provided that one or both of $A'^{13}$ and $A'^{14}$ represents a fluorine-containing aliphatic hydrocarbon group.

Examples of the alkanediyl group for $L^5$ include the same ones as those for $L^{4a}$.

$A'^{13}$ further includes combined groups of chain hydrocarbon groups and alicyclic hydrocarbon groups.

As to $A'^{13}$, the chain or alicyclic hydrocarbon group which may have a fluorine atom is preferably a divalent saturated chain hydrocarbon group which may have a fluorine atom, more preferably a perfluoroalkanediyl group.

Examples of the divalent chain saturated hydrocarbon group which may have a fluorine atom include an alkanediyl group such as a methylene group, an ethylene group, a propanediyl group, a butanediyl group and pentanediyl group; and a perfluoroalkanediyl group such as a difluoromethylene group, a perfluoroethylene group, a perfluoropropanediyl group, a perfluorobutanediyl group and perfluoropentanediyl group.

The divalent cyclic saturated hydrocarbon group which may have a fluorine atom may be a divalent monocyclic or polycyclic group.

Examples of the divalent monocyclic hydrocarbon group which may have a fluorine atom include a cyclohexanediyl group and a perfluorocyclohexanediyl group.

Examples of the divalent polycyclic hydrocarbon group which may have a fluorine atom include an adamantanediyl group, norbornanediyl group, and a perfluoroadamantanediyl group.

In the group represented by $A'^{14}$, the aliphatic hydrocarbon group includes chain saturated hydrocarbon groups, cyclic saturated hydrocarbon groups and combined groups of these saturated hydrocarbon groups.

As to $A'^{14}$, the chain or alicyclic hydrocarbon group which may have a fluorine atom is preferably a saturated aliphatic hydrocarbon group which may have a fluorine atom, more preferably a perfluoroalkanediyl group.

Examples of the chain hydrocarbon group which may have a fluorine atom include a trifluoromethyl group, a difluoromethyl group, a methyl group, a perfluoroethyl group, a 2,2,2-trifluoroethyl group, a 2,2,3,4-tetrafluoroethyl group, an ethyl group, a perfluoropropyl group, a 2,2,3,3,3-pentafluoropropyl group, a propyl group, a perfluorobutyl group, 1,1,2,2,3,3,4,4-octafluorobutyl group, a butyl group, a perfluoropentyl group, 2,2,3,3,4,4,5,5,5-nonafluoropentyl group, a pentyl group, a hexyl group, a perfluorohexyl group, a heptyl group, a perfluoroheptyl group, an octyl group and a perfluorooctyl group.

The alicyclic hydrocarbon group which may have a fluorine atom may be monocyclic or polycyclic group.

Examples of the monovalent monocyclic hydrocarbon group which may have a fluorine atom include a cyclopropyl group, a cyclopentyl group, a cyclohexyl group, and a perfluorocyclohexyl group.

Examples of the polycyclic hydrocarbon group which may have a fluorine atom include an adamantyl group, a norbornyl group, and a perfluoroadamantyl group.

Examples of the combined groups of the above-mentioned chain and alicyclic hydrocarbon groups include a cyclopropylmethyl group, a cyclobutylmethyl group, an adamantylmethyl group, a norbornylmethyl group and a perfluoroadamantylmethyl group.

In formula (a4-3), $L^5$ is preferably an ethylene group.

The chain or alicyclic hydrocarbon group represented by $A'^{13}$ has preferably 6 or less, more preferably 2 to 3, of carbon atoms.

The chain or alicyclic hydrocarbon group represented by $A'^{14}$ has preferably 3 to 12, more preferably 3 to 10, of carbon atoms.

$A'^{14}$ has preferably a C3-C12 alicyclic hydrocarbon group, more preferably a cyclopropylmethyl group, a cyclopentyl group, a cyclohexyl group, a norbornyl group or an adamantyl group.

Examples of the structural unit represented by formula (a4-3) include preferably those represented by formulae (a4-1'-1) to (a4-1'-11) and those in which a methyl group represented by $R^{17}$ has been replaced by a hydrogen atom.

Another example of the structural unit (a4) includes those represented by formula (a4-4).

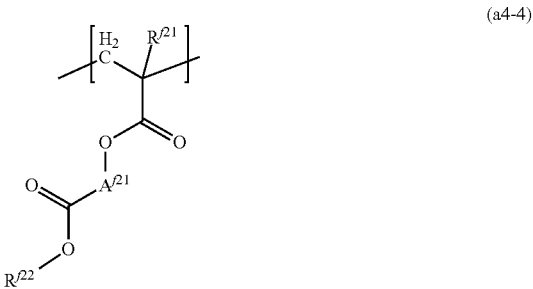

(a4-4)

In formula (a4-4), wherein $R^{f21}$ represents a hydrogen atom or a methyl group;

$A^{f21}$ represents $-(CH_2)_{j1}-$, $-(CH_2)_{j2}-O-(CH_2)_{j3}-$ or $-(CH_2)_{j4}-CO-O-(CH_2)_{j5}-$ where j1, j2, j3, j4 or j5 each independently represent an integer of 1 to 6; and $R^{f22}$ represents a C1-C10 hydrocarbon group having a fluorine atom.

For $R^{f22}$, examples of the hydrocarbon group having a fluorine atom include those as referred to for $R^{f2}$.

$R^{f22}$ is preferably a C1-C10 alkyl group having a fluorine atom or a C3-C10 alicyclic hydrocarbon group having a fluorine atom, more preferably a C1-C10 alkyl group having a fluorine atom, and still more preferably a C1-C6 alkyl group having a fluorine atom.

In formula (a4-4), $A^{f21}$ is preferably $-(CH_2)_{j1}-$, more preferably a methylene or ethylene group, and still more preferably a methylene group.

Examples of the structural unit represented by formula (a4-4) include preferably the following ones and those represented by the following formulae in which the methyl group corresponding to $R^{f21}$ has been replaced by a hydrogen atom.

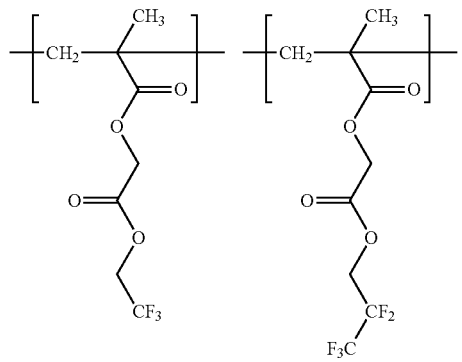

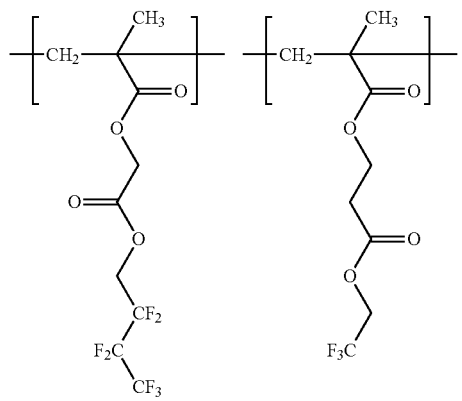

-continued

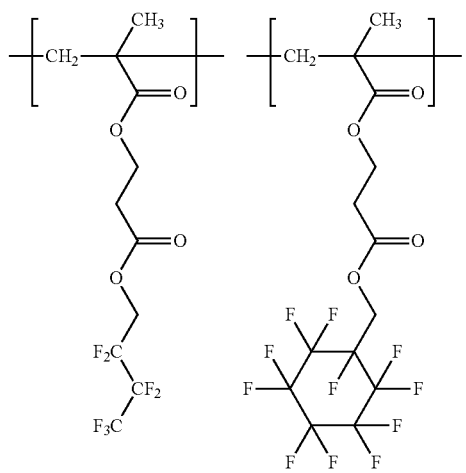

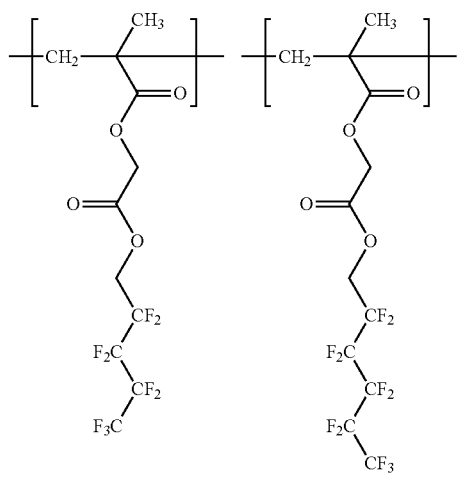

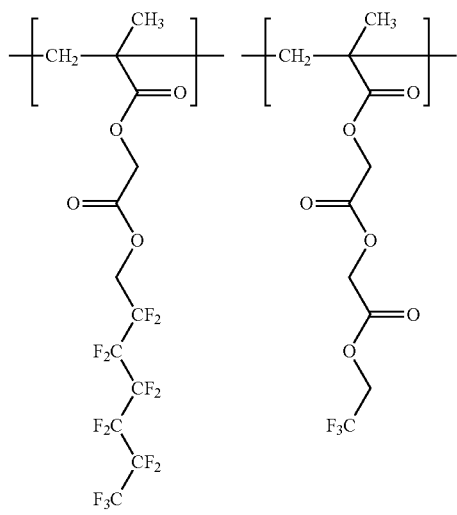

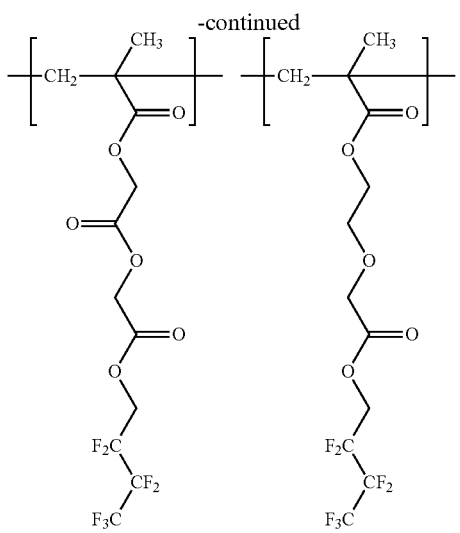

When Resin (A) has the structural unit (a4), its content is preferably 1 to 20% by mole, more preferably 2 to 15% by mole and still more preferably 3 to 10% by mole based on 100% by mole of all the structural units of the resin.

Other examples of the structural unit (s) include one having an acid-stable hydrocarbon group. The structural unit (s) having an acid-stable hydrocarbon group is sometimes referred to as "structural unit (a5)".

Herein, the term "acid-stable hydrocarbon group" means such a hydrocarbon group that is not removed from the structural unit having the group by action of an acid generated from an acid generator as described above.

The acid-stable hydrocarbon group may be a linear, branched or cyclic hydrocarbon group.

The structural unit which has a hydrocarbon not being removed therefrom by action of an acid may have a linear, branched or cyclic hydrocarbon, preferably an alicyclic hydrocarbon group.

Examples of the structural unit having an acid-stable hydrocarbon group include one represented by formula (a5-1):

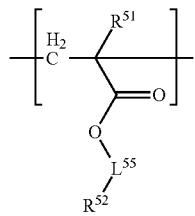
(a5-1)

where $R^{51}$ represents a hydrogen atom or a methyl group;

$R^{52}$ represents a C3-C18 monovalent alicyclic hydrocarbon group which may have a C1-C8 monovalent aliphatic hydrocarbon group as a substituent, provided that the alicyclic hydrocarbon group has no substituent on the carbon atom bonded to $L^{55}$; and $L^{55}$ represents a single bond or a C1-C18 divalent saturated hydrocarbon group where a methylene group can be replaced by an oxygen atom or carbonyl group, provided that $L^{55}$ does not represent lactone ring.

The alicyclic hydrocarbon group represented by $R^{52}$ may be monocyclic or polycyclic one.

Examples of the alicyclic hydrocarbon group include a monocyclic hydrocarbon group such as a C3-C18 cycloalkyl group (e.g. a cyclopropyl group, a cyclobutyl group, a cyclopentyl group, a cyclohexyl group) and a polycyclic alicyclic hydrocarbon group such as an adamantyl group, or a norbornyl group.

Examples of the aliphatic hydrocarbon group include an alkyl groups such as a methyl group, an ethyl group, n-propyl group, isopropyl group, n-butyl group, sec-butyl group, tert-butyl group, a pentyl group, a hexyl group, an octyl group and 2-ethylhexyl group.

Examples of the alicyclic hydrocarbon group having a substituent include a 3-methyladamantyl group.

$R^{52}$ is preferably a C3-C18 unsubstituted alicyclic hydrocarbon group, more preferably an adamantyl group, a norbornyl group or a cyclohexyl group.

Examples of the divalent saturated hydrocarbon group represented by $L^{55}$ include divalent aliphatic hydrocarbon groups and divalent alicyclic hydrocarbon groups, preferably divalent aliphatic hydrocarbon groups.

Examples of divalent aliphatic hydrocarbon groups include alkanediyl groups such as a methylene group, an ethylene group, a propanediyl group, a butanediyl group and a pentanediyl group.

The divalent alicyclic hydrocarbon groups may be monocyclic or polycyclic one.

Examples of divalent monocyclic hydrocarbon groups include cycloalkanediyl groups such as a cyclopentanediyl group and a cyclohexanediyl group. Examples of divalent polycyclic alicyclic hydrocarbon groups include an adamantanediyl group and a norbornanediyl group.

Examples of the divalent hydrocarbon group where a methylene group has been replaced by an oxygen atom or carbonyl group include those represented by formulae (L1-1) to (L1-4).

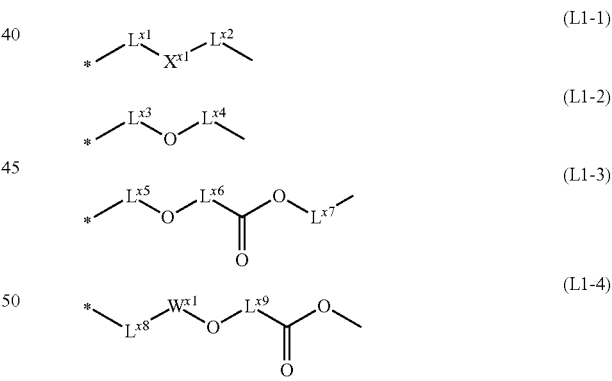

In these formulae, * represents a binding position to an oxygen atom.

$X^{x1}$ is a carbonyloxy group or an oxycarbonyl group; and $L^{x1}$ is a C1-C16 divalent aliphatic saturated hydrocarbon group, and $L^{x2}$ is a single bond or a C1-C15 divalent chain or alicyclic hydrocarbon group, provided that the total number of the carbon atoms in $L^{x1}$ and $L^{x2}$ is 16 or less.

$L^{x3}$ is a C1-C17 divalent aliphatic saturated hydrocarbon group, and $L^{x4}$ is a single bond or a C1-C16 divalent chain or alicyclic hydrocarbon group, provided that the total number of the carbon atoms in $L^{x3}$ and $L^{x4}$ is 17 or less.

$L^{x5}$ is a C1-C15 divalent aliphatic saturated hydrocarbon group, and $L^{x6}$ and $L^{x7}$ are a single bond or a C1-C14 divalent chain or alicyclic hydrocarbon group, provided that the total number of the carbon atoms in $L^{x5}$, $L^{x6}$ and $L^{x7}$ is 15 or less.

$L^{x8}$ and $L^{x9}$ are each independently a single bond or a C1-C12 divalent chain or alicyclic hydrocarbon group, and $W^{x1}$ is a C3-C15 divalent cyclic saturated hydrocarbon group, provided that the total number of the carbon atoms in $L^{x8}$, $L^{x9}$ and $W^{x1}$ is 15 or less.

$L^{x1}$ is preferably a C1-C8 divalent aliphatic saturated hydrocarbon group, more preferably a methylene group or an ethylene group.

$L^{x2}$ is preferably a single bond, or a C1-C8 divalent aliphatic saturated hydrocarbon group, more preferably a single bond.

$L^{x3}$ is preferably a C1-C8 divalent aliphatic saturated hydrocarbon group, more preferably a methylene group or an ethylene group.

$L^{x4}$ is preferably a single bond or a C1-C8 divalent aliphatic saturated hydrocarbon group, more preferably a single bond, a methylene group or an ethylene group.

$L^{x5}$ is preferably a C1-C8 divalent aliphatic saturated hydrocarbon group, more preferably a methylene group or an ethylene group.

$L^{x6}$ is preferably a single bond or a C1-C8 divalent aliphatic saturated hydrocarbon group, more preferably a methylene group or an ethylene group.

$L^{x7}$ is preferably a single bond or a C1-C8 divalent aliphatic saturated hydrocarbon group, more preferably a methylene group or an ethylene group.

$L^{x8}$ is preferably a single bond or a C1-C8 divalent aliphatic saturated hydrocarbon group, more preferably a single bond or a methylene group.

$L^{x9}$ is preferably a single bond or a C1-C8 divalent aliphatic saturated hydrocarbon group, more preferably a single bond or a methylene group.

$W^{x1}$ is a preferably C3-C10 divalent cyclic saturated hydrocarbon group, more preferably a cyclohexanediyl group or an adamantanediyl group.

Examples of the group represented by formula (L1-1) include the following ones.

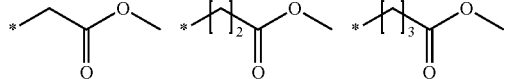
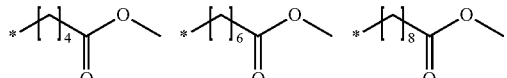
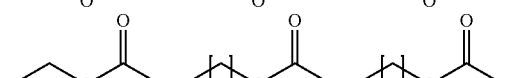
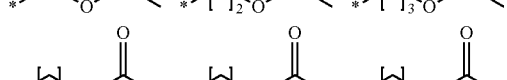
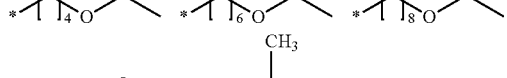
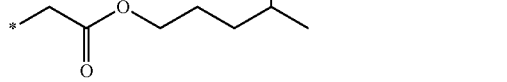
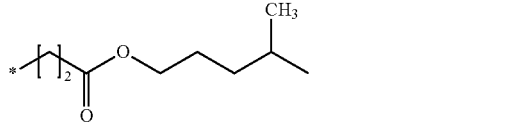
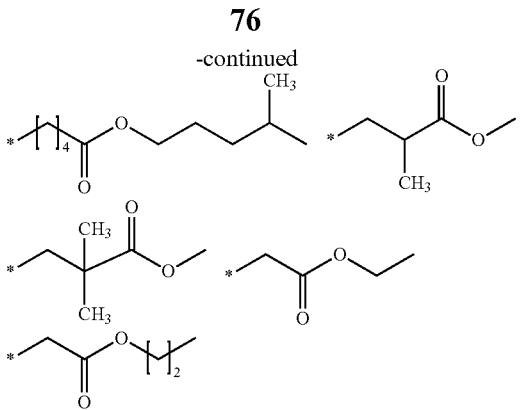

In these formulae, * represents a binding position to an oxygen atom.

Examples of the group represented by formula (L1-2) include the following ones.

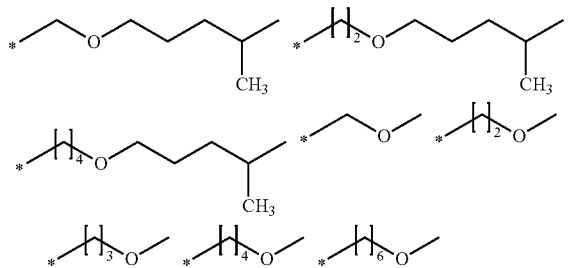

In these formulae, * represents a binding position to an oxygen atom.

Examples of the group represented by formula (L1-3) include the following ones.

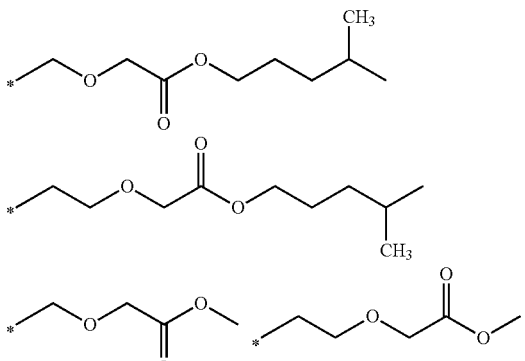

In these formulae, * represents a binding position to an oxygen atom.

Examples of the group represented by formula (L1-4) include the following ones.

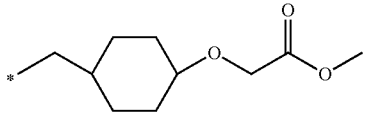

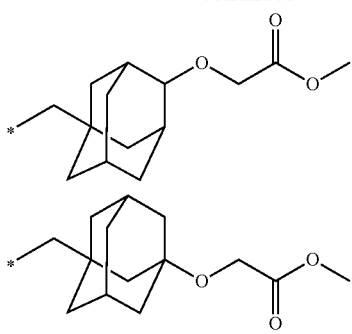
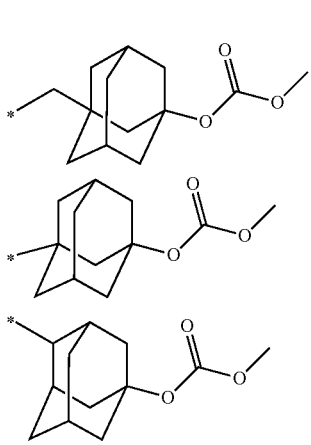
In these formulae, * represents a binding position to an oxygen atom.
$L^{55}$ is preferably a single bond or a group represented by formula (L1-1).
Examples of the structural unit represented by formula (a5-1) include the following ones and those where a methyl group has been replaced by a hydrogen atom in each formula.
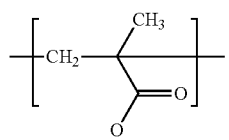 (a5-1-1)
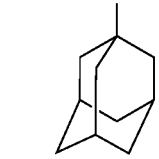
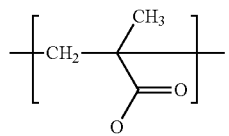 (a5-1-2)
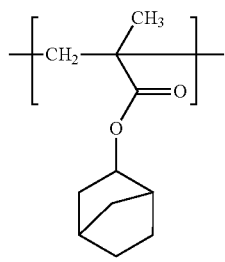 (a5-1-3)
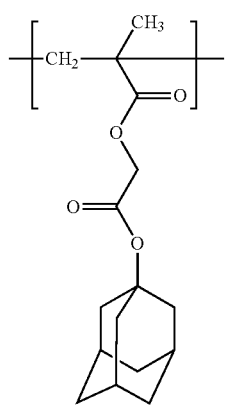 (a5-1-4)
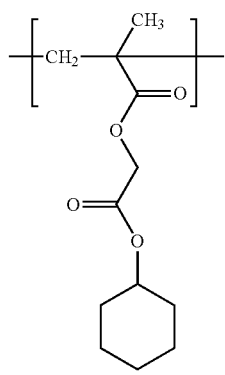 (a5-1-5)
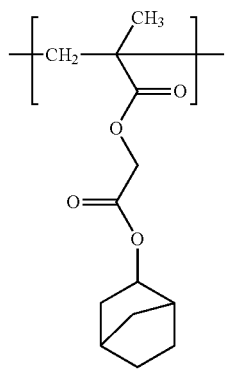 (a5-1-6)

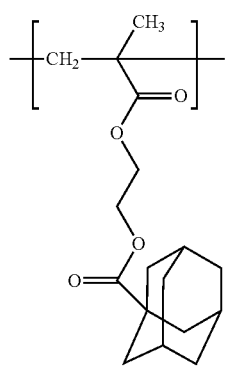 (a5-1-7)
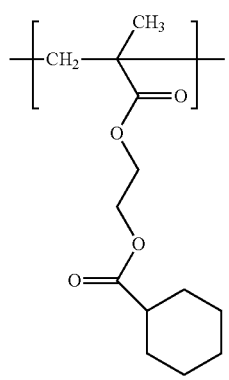 (a5-1-8)
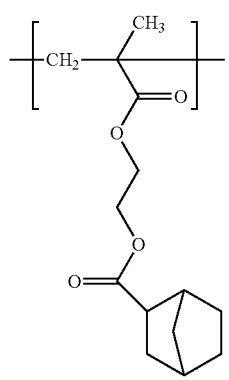 (a5-1-9)
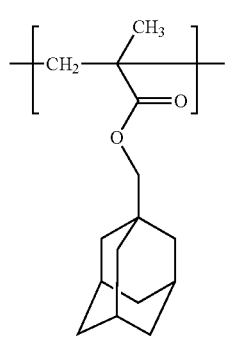 (a5-1-10)
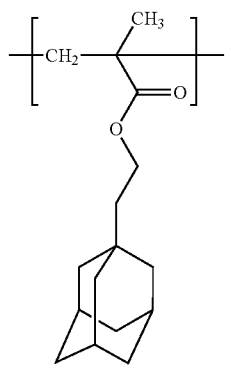 (a5-1-11)
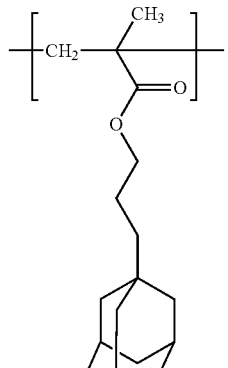 (a5-1-12)
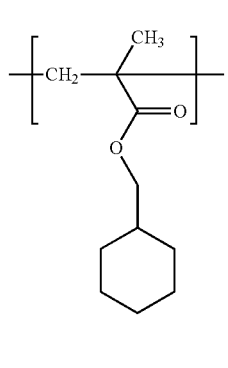 (a5-1-13)
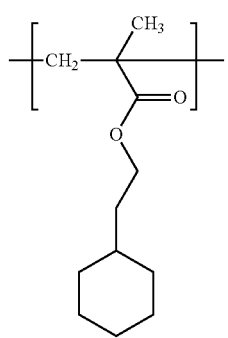 (a5-1-14)

-continued (a5-1-15)
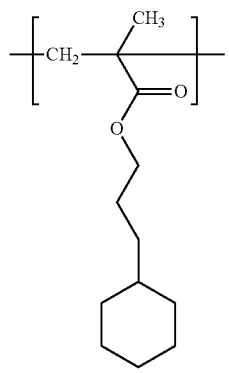

(a5-1-16)
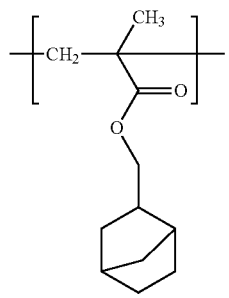

(a5-1-17)
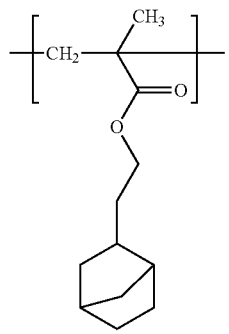

(a5-1-18)
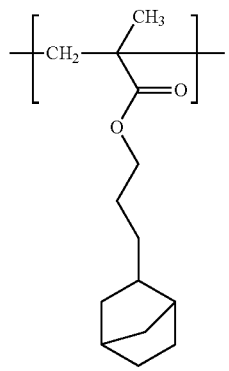

When Resin (A) has the structural unit (a5), its content is preferably 1 to 30% by mole, more preferably 2 to 20% by mole and still more preferably 3 to 15% by mole based on 100% by mole of all the structural units of the resin.

<Structural unit (II)>

Resin (A) may comprise a structural unit decomposed by irradiation to generate an acid. Said structural unit is referred to as "the structural unit (II)". Examples of the structural unit (II) include one as described in JP2016-79235A1.

The structural unit (II) preferably comprises a sulfonate or carboxylate group and an organic cation, or a $S^+$ group and an organic anion at its side chain.

The structural unit (II) which comprises a sulfonate or carboxylate group and an organic cation at its side chain is preferably represented by formula (II-2-A'):

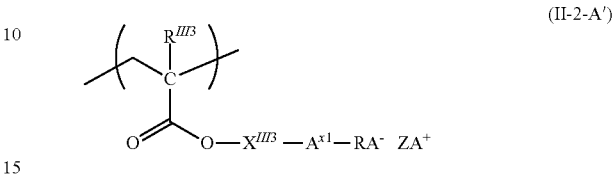

(II-2-A')

wherein $X^{III3}$ represents a C1-C18 divalent saturated hydrocarbon group in which a methylene group can be replaced by —O—, —S— or —CO— and in which a hydrogen atom can be replaced by a fluorine atom, a hydroxyl group or a C1-C6 alkyl group which may have a fluorine atom, $A^{x1}$ represents a C1-C8 alkanediyl group in which a hydrogen atom can be replaced by a fluorine atom or a C1-C6 perfluoroalkyl group, $RA^-$ represents a sulfonate or carboxylate group, $R^{III3}$ represents a hydrogen atom, a halogen atom or a C1-C6 alkyl group in which a hydrogen atom can be replaced by a halogen atom, and $ZA^+$ represents an organic cation.

For $R^{III3}$, examples of the halogen atom include a fluorine atom, a chlorine atom, a bromine atom and an iodine atom.

For $R^{III3}$, examples of a halogen-containing alkyl group include a trifluoromethyl group and a perfluoroethyl group.

For $A^{x1}$, examples of the alkanediyl group include a methylene group, an ethylene group, a propane-1,3-diyl group, a butane-1,4-diyl group, a pentane-1,5-diyl group, a hexane-1,6-diyl group, an ethane-1,1-diyl group, a propane-1,1-diyl group, a propane-1,2-diyl group, a propane-2,2-diyl group, a pentane-2,4-diyl group, a 2-methylpropane-1,3-diyl group, 2-methylpropane-1,2-diyl group, pentane-1,4-diyl group, and 2-methylbutane-1,4-diyl group.

For $X^{III3}$, examples of divalent aliphatic hydrocarbon groups include a linear alkanediyl group, a branched alkanediyl group, a monocyclic alicyclic hydrocarbon, a polycyclic alicyclic hydrocarbon, and any combinations of these groups, specific examples of which include a linear alkanediyl group such as a methylene group, an ethylene group, a propane-1,3-diyl group, a propane-1,2-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, an undecane-1,11-diyl group, a dodecane-1,12-diyl group; a branched alkanediyl group such as a butane-1,3-diyl group, a 2-methylpropane-1,3-diyl group, a 2-methylpropane-1,2-diyl group, a pentane-1,4-diyl group, and a 2-methylbutane-1,4-diyl group; cycloalkanediyl groups such as a cyclobutane-1,3-diyl group, a cyclopentane-1,3-diyl group, a cyclohexane-1,4-diyl group and a cyclooctane-1,5-diyl group; and divalent polycyclic alicyclic hydrocarbon groups such as norbornane-1,4-diyl group, norbornane-2,5-diyl group, adamantane-1,5-diyl group, and adamantane-2,6-diyl group.

Examples of the saturated hydrocarbon group in which a methylene group has been replaced by —O—, —S— or —CO— include divalent groups represented by the formulae ($X^1$) to ($X^{53}$).

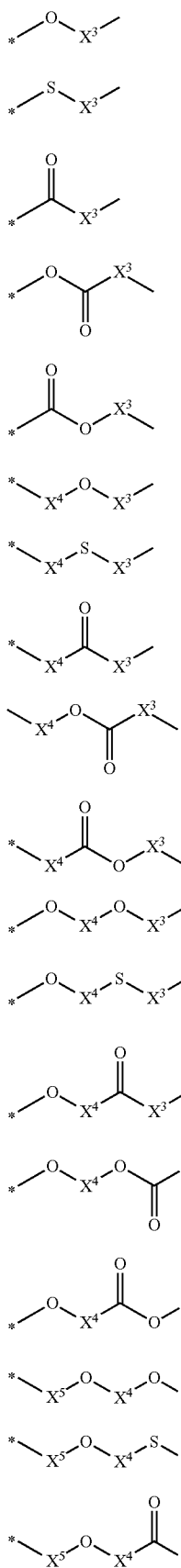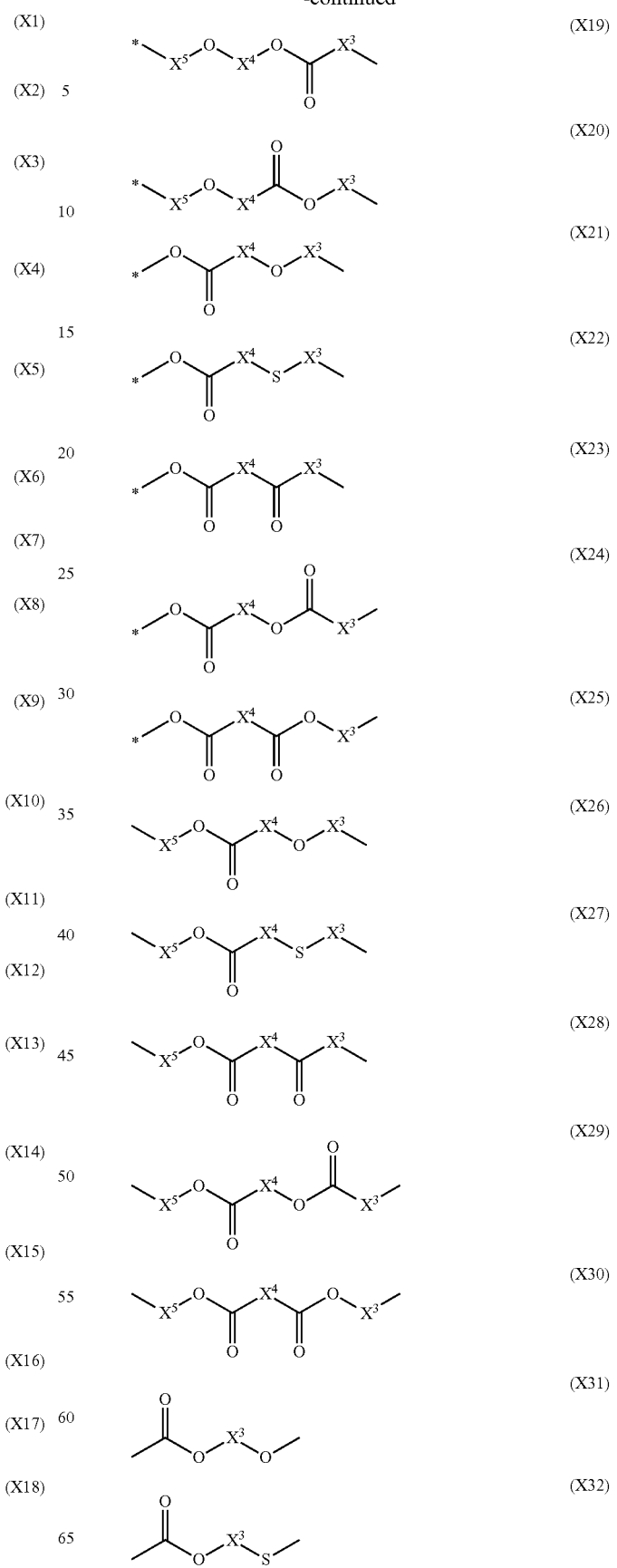

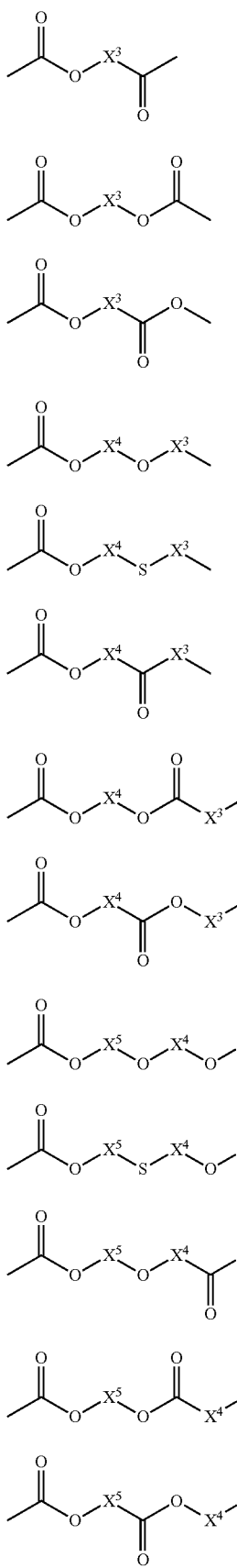
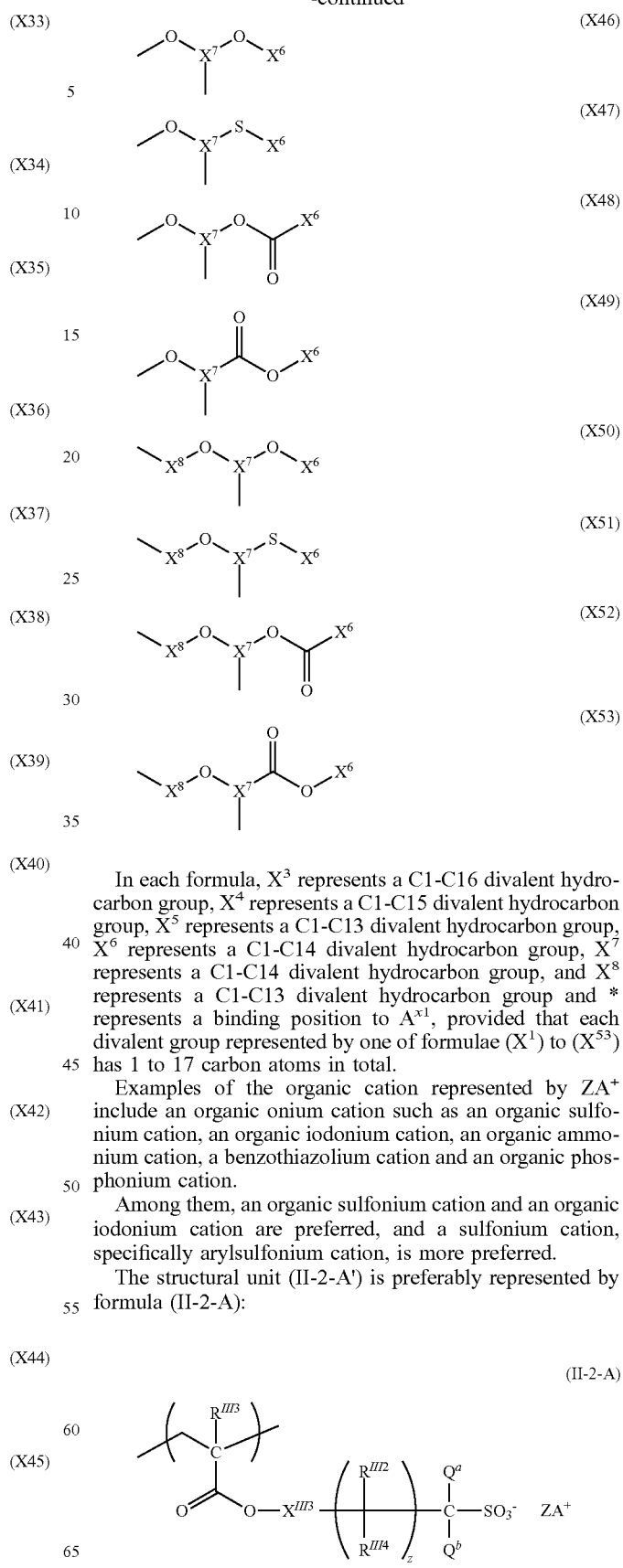

In each formula, $X^3$ represents a C1-C16 divalent hydrocarbon group, $X^4$ represents a C1-C15 divalent hydrocarbon group, $X^5$ represents a C1-C13 divalent hydrocarbon group, $X^6$ represents a C1-C14 divalent hydrocarbon group, $X^7$ represents a C1-C14 divalent hydrocarbon group, and $X^8$ represents a C1-C13 divalent hydrocarbon group and * represents a binding position to $A^{x1}$, provided that each divalent group represented by one of formulae $(X^1)$ to $(X^{53})$ has 1 to 17 carbon atoms in total.

Examples of the organic cation represented by $ZA^+$ include an organic onium cation such as an organic sulfonium cation, an organic iodonium cation, an organic ammonium cation, a benzothiazolium cation and an organic phosphonium cation.

Among them, an organic sulfonium cation and an organic iodonium cation are preferred, and a sulfonium cation, specifically arylsulfonium cation, is more preferred.

The structural unit (II-2-A') is preferably represented by formula (II-2-A):

wherein $X^{III3}$, $R^{III3}$ and $ZA^+$ are as defined above;

$R^{III2}$ and $R^{III4}$ each independently represent a hydrogen atom, a fluorine atom or a C1-C6 perfluoroalkyl group;

z represents an integer of 0 to 6; and $Q^a$ and $Q^b$ each independently represent a fluorine atom or a C1-C6 perfluoroalkyl group.

For $Q^a$, $Q^b$, $R^{III2}$ and $R^{III4}$, examples of a perfluoroalkyl group include a trifluoromethyl group, a pentafluoroethyl group, a heptafluoropropyl group, a nonafluorobutyl group, an undecafluoropentyl group and a tridecafluorohexyl group, and a trifluoromethyl group is preferred.

The structural unit (II-2-A) is preferably represented by formula (II-2-A-1):

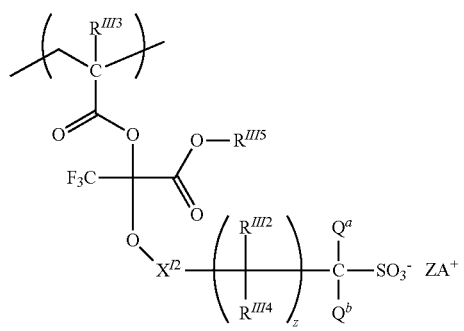

(II-2-A-1)

wherein $R^{III2}$, $R^{III3}$, $R^{III4}$, $Q^a$, $Q^b$, z and $ZA^+$ are as defined above;

$R^{III5}$ represents a C1-C12 saturated hydrocarbon group, and $X^{I2}$ represents a C1-C18 divalent saturated hydrocarbon group in which a methylene group can be replaced by —O—, —S— or —CO— and in which a hydrogen atom can be replaced by a halogen atom or a hydroxyl group.

For $R^{III5}$, examples of the saturated hydrocarbon group include chain alkyl groups such as methyl group, an ethyl group, a propyl group, an isopropyl group, a butyl group, a sec-butyl group, a tert-butyl group, a pentyl group, a hexyl group, a heptyl group, a 2-ethylhexyl group and a dodecyl group.

For $X^{I2}$, examples of the divalent saturated hydrocarbon group include the same examples as the divalent saturated hydrocarbon group for $X^{III3}$.

The structural unit (II-2-A-1) is preferably represented by formula (II-2-A-2):

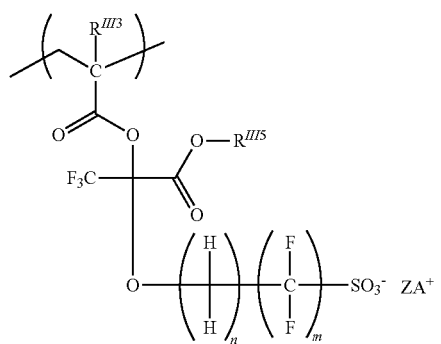

(II-2-A-2)

wherein $R^{III3}$, $R^{III5}$, and $ZA^+$ are as defined above; and n and m each independently represent 1 or 2.

Examples of the structural unit represented by formula (II-2-A') include the following ones and those recited in WO2012/050015A1.

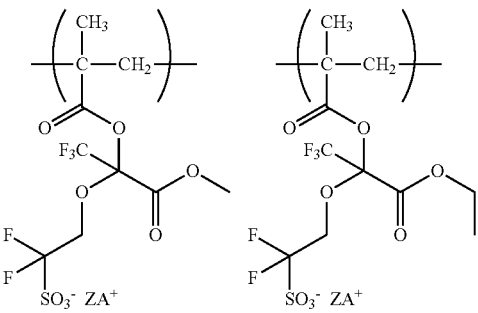

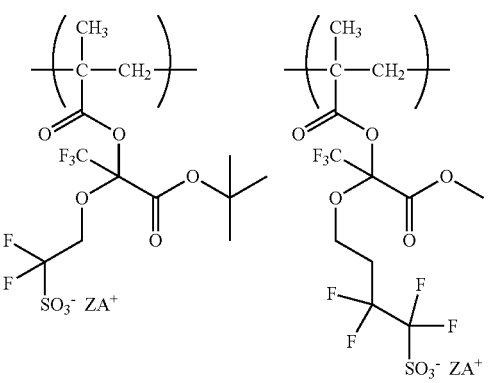

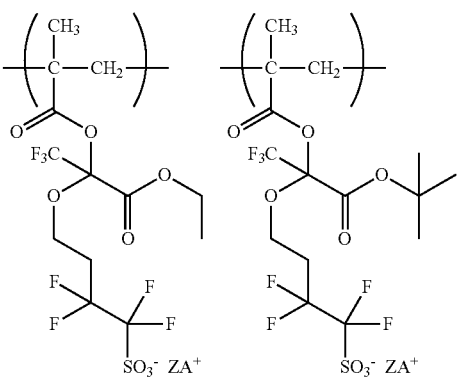

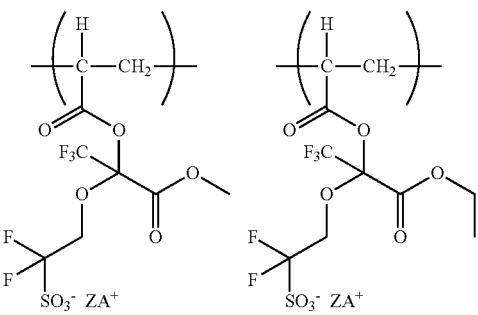

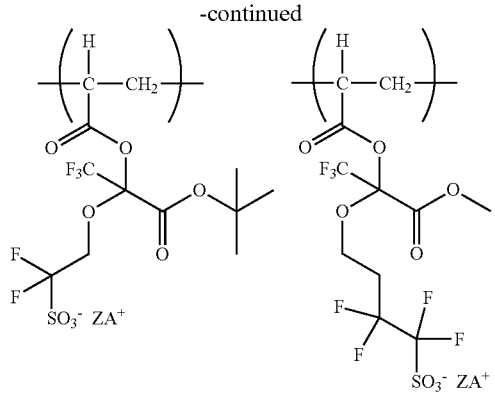
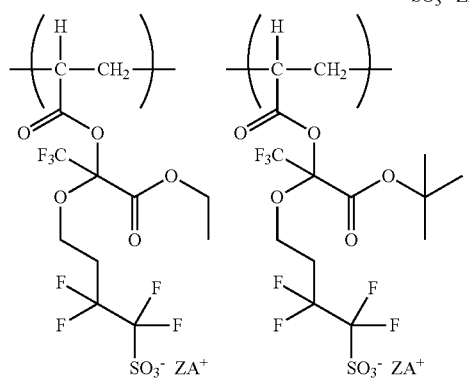
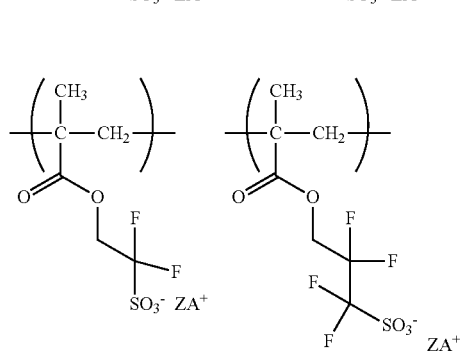
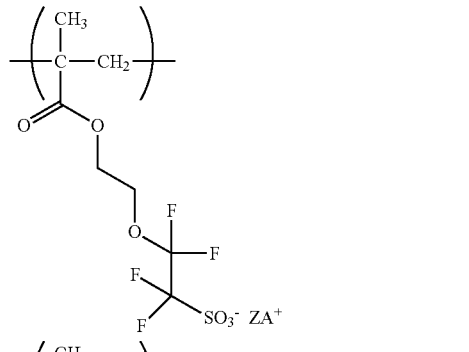
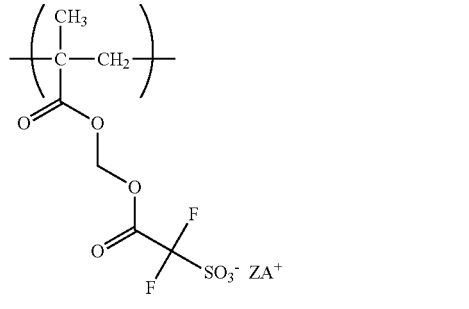
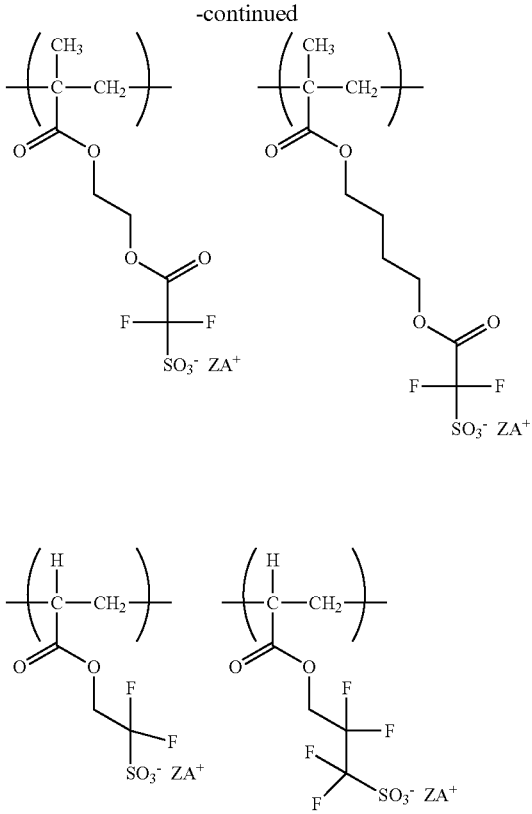
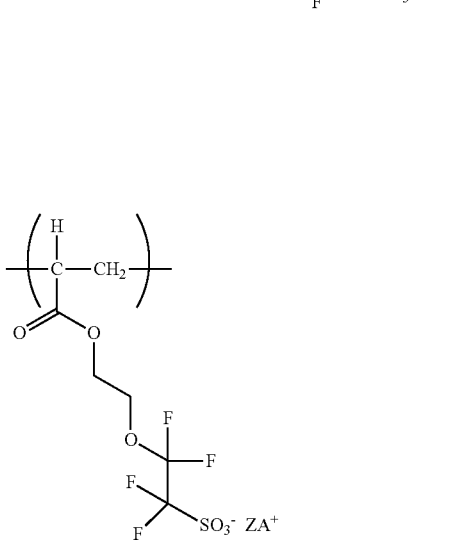
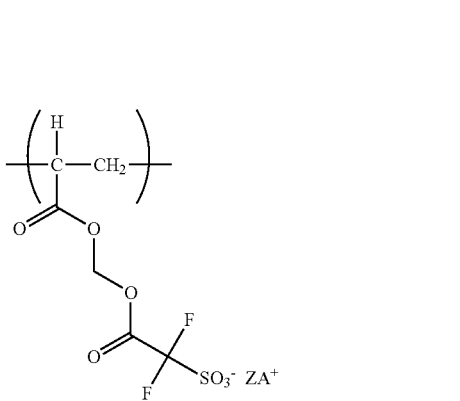

-continued

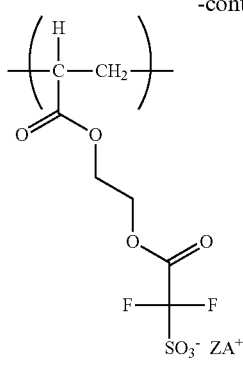 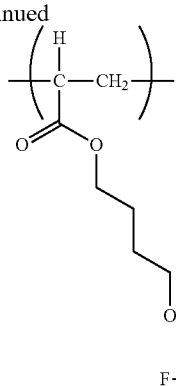

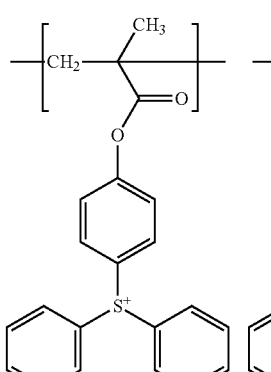 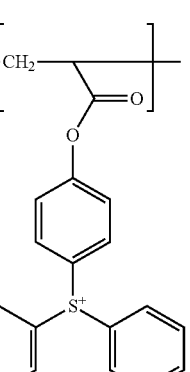

The structural unit (II) which comprises a S⁺ group and an organic anion at its side chain is preferably represented by formula (II-1-1):

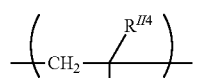
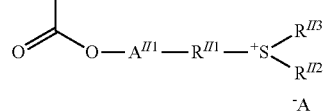
(II-1-1)

wherein $A^{II1}$ represents a single bond or a divalent connecting group, $R^{II1}$ represents a C6-C18 divalent aromatic hydrocarbon group, $R^{II2}$ and $R^{II3}$ each independently represent a C1-C18 hydrocarbon group or jointly represents a ring structure together S⁺ bonded thereto, $R^{II4}$ represents a hydrogen atom, a halogen atom or a C1-C6 alkyl group in which a hydrogen atom can be replaced by a halogen atom, and A⁻ represents an organic anion.

For $R^{II1}$, examples of the aromatic hydrocarbon group include a phenylene group and naphthylene group.

For $R^{II2}$ and $R^{II3}$, examples of the hydrocarbon group include the alkyl groups, alicyclic hydrocarbon groups, aromatic hydrocarbon groups and any combination of these groups.

For $R^{II4}$, examples of the halogen atom include a fluorine atom, a chlorine atom, a bromine atom and an iodine atom.

For $R^{II4}$, examples of a halogen-containing alkyl group include a trifluoromethyl group and a perfluoroethyl group.

For $A^{II1}$, examples of the divalent connecting group include a C1-C18 divalent saturated hydrocarbon group in which a methylene group can be replaced by —O—, —S— or —CO—. Specific examples of the divalent connecting group include the same saturated hydrocarbon group represented by $X^{III3}$.

Examples of cation of the structural unit represented by formula (II-1-1) include the following ones.

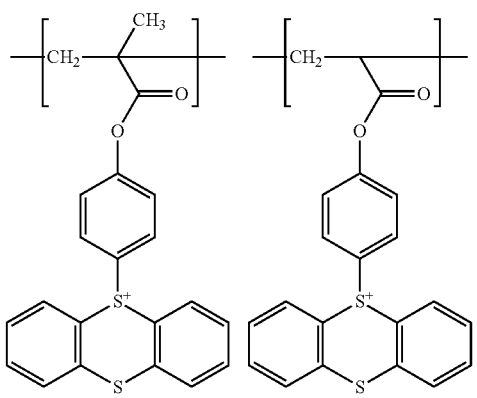

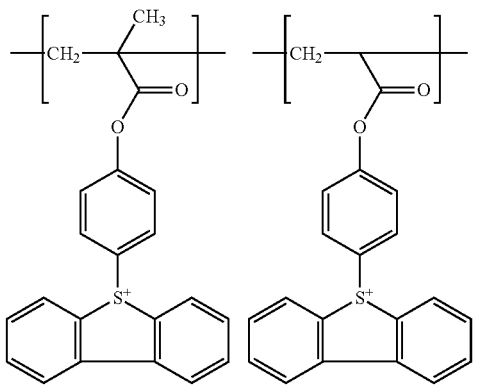

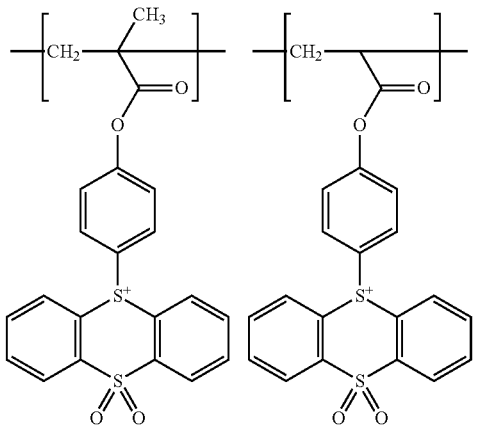

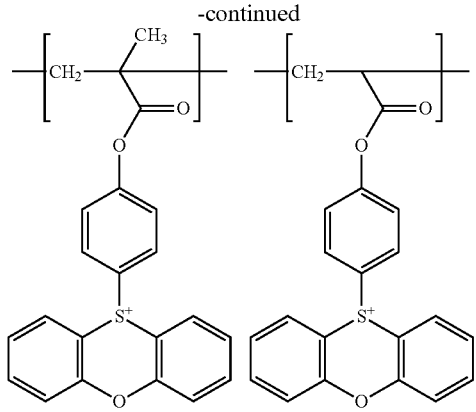
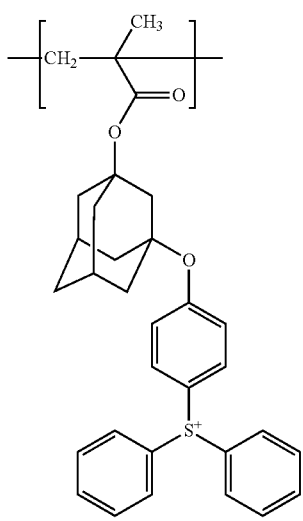
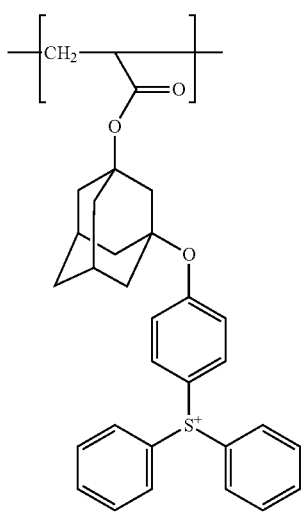
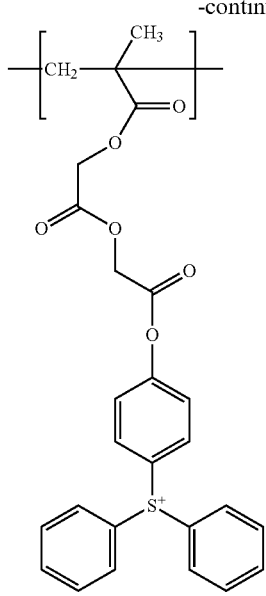
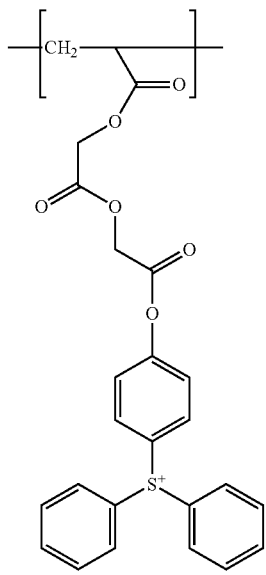
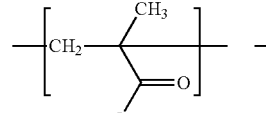
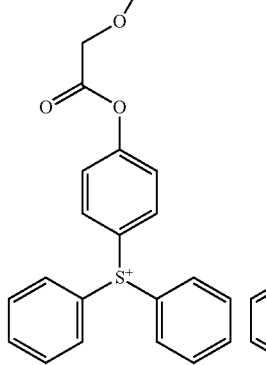

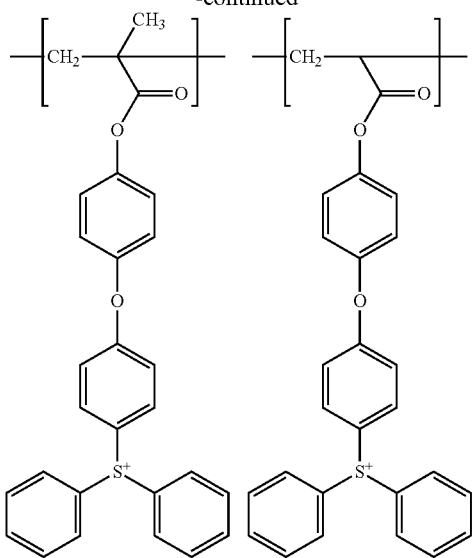
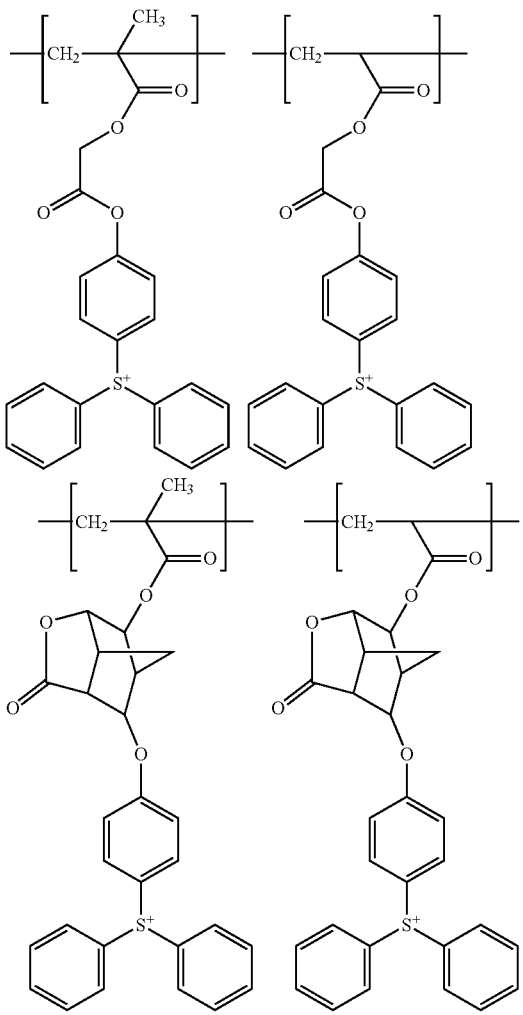

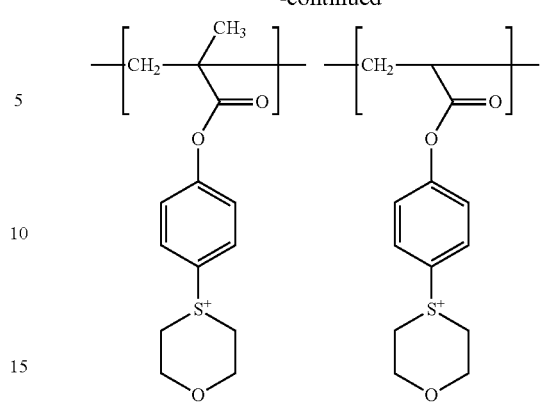

Examples of the organic anion represented by A⁻ include a sulfonate anion, a sulfonylimide anion, a sulfonylmethide anion and a carboxylate anion.

Among them, a sulfonate anion is preferred. For A⁻, a sulfonate anion is preferably the same one as used for the salt represented by formula (B).

For A⁻, examples of a sulfonylimide anion include the following ones.

 (I-b-1)

 (I-b-2)

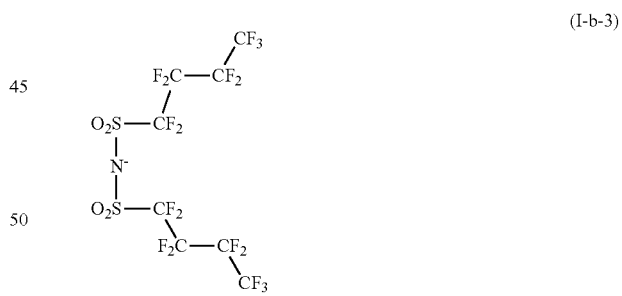 (I-b-3)

(I-b-4)

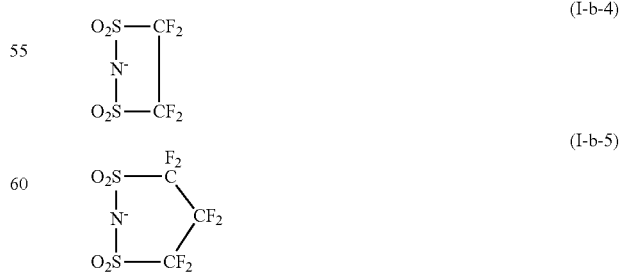 (I-b-5)

For A⁻, examples of a sulfonylmethide anion include the following ones.

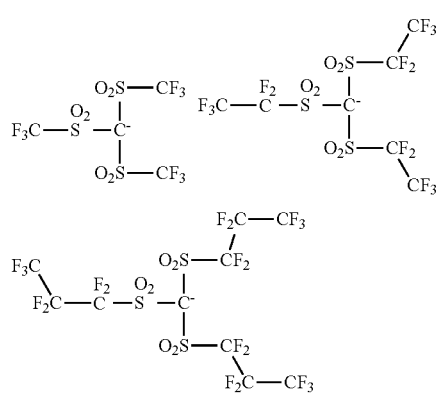
For A⁻, examples of a carbonyloxy anion include the following ones.
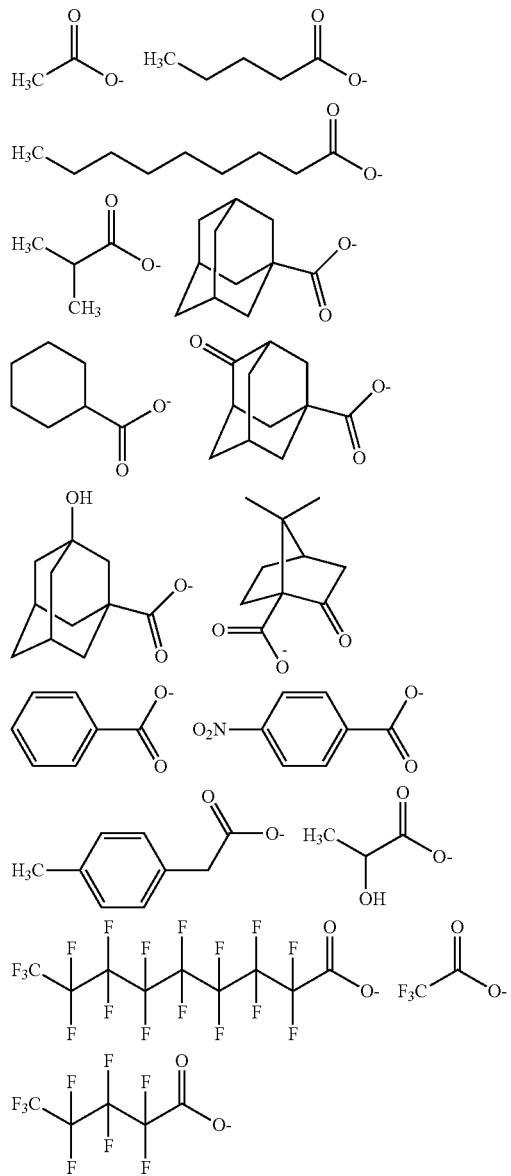
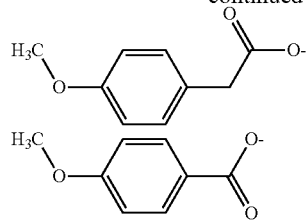
Examples of the structural unit represented by formula (II-1-1) include the following ones.
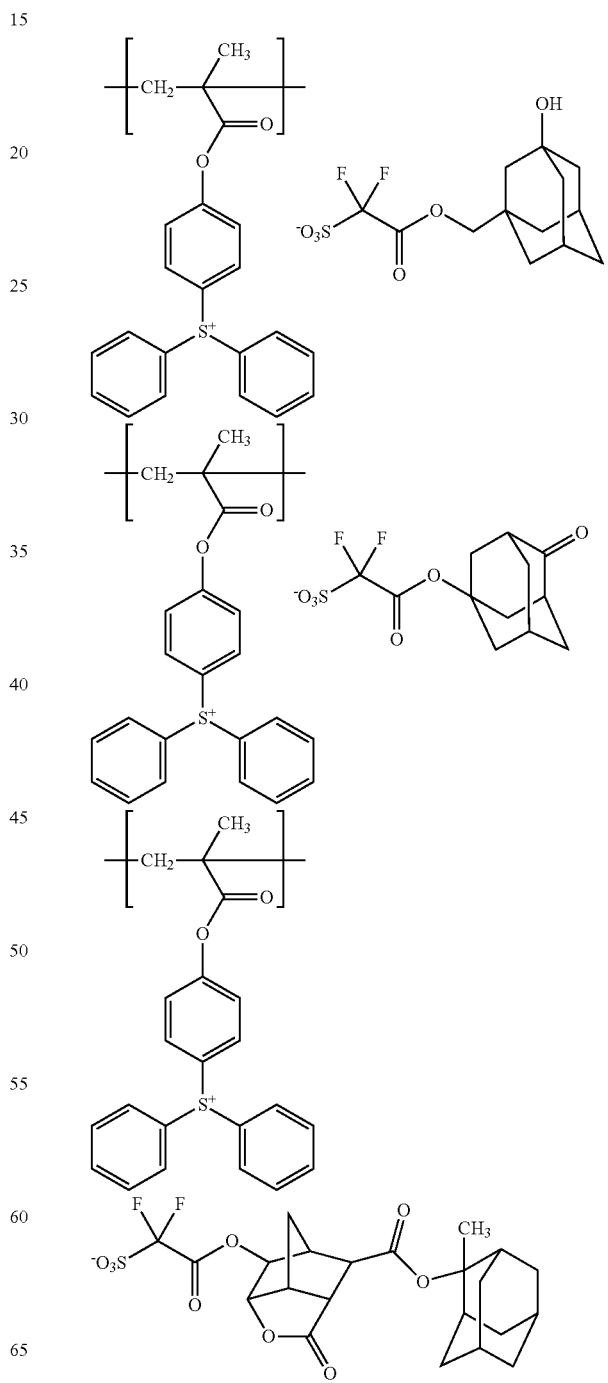

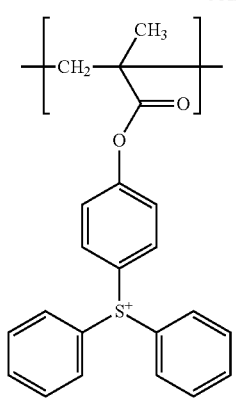
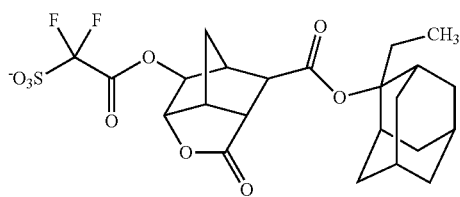
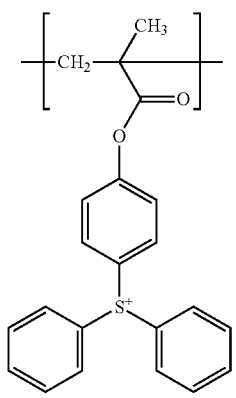
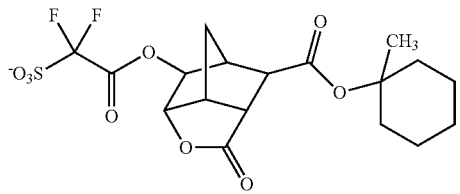
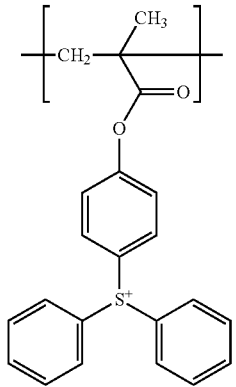
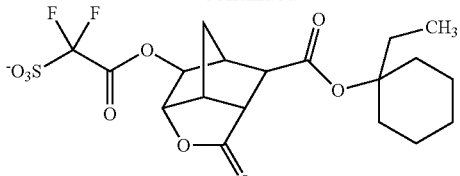
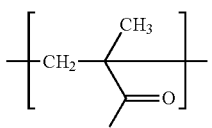
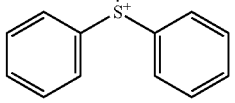
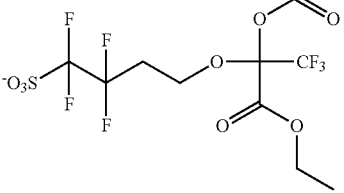
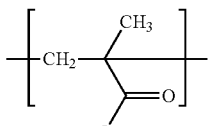
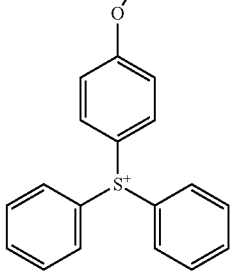
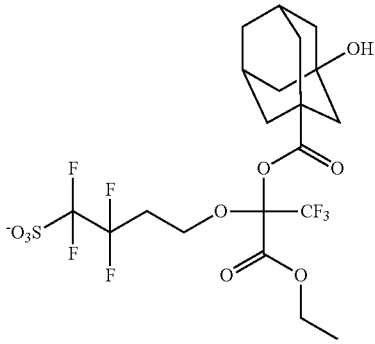
When Resin (A) has the structural unit (II), its content is preferably 1 to 20% by mole, more preferably 2 to 15% by mole, still more preferably 3 to 10% by mole, based on 100% by mole of all the structural units of the resin.

Resin (A) is generally one which consists of the structural unit (I), one which consists of the structural unit (I) and a structural unit (a1), one which consists of the structural unit (I) and a structural unit (s), or one which consists of the structural unit (I), a structural unit (a1) and a structural unit (s).

Examples of Resin (A) which consists of the structural unit (I), a structural unit (a1) and a structural unit (s) include one which has the structural unit (I), a structural unit (a1), a structural unit (a2) or (a3), one which has the structural unit (I), a structural unit (a1), a structural unit (a2) or (a3) and the structural unit (a4), and one which has the structural unit (I), a structural unit (a1), a structural unit (a4) and/or (a5).

The structural unit (a1) is preferably one selected from the group consisting of the structural unit (a1-0), the structural unit (a1-0X), the structural unit (a1-1), the structural unit (a1-2), particularly that is one having a cyclohexyl group or a cyclopentyl group. More preferably, Resin (A) has two structural units selected from the group consisting of the structural unit (a1-0), the structural unit (a1-0X), the structural unit (a1-1), the structural unit (a1-2), particularly that is one having a cyclohexyl group or a cyclopentyl group.

The structural unit (s) is preferably one selected from the group consisting of the structural unit (a2) and the structural unit (a3). The structural unit (a2) is preferably the structural unit (a2-A). The structural unit (a3) is preferably the structural unit (a3-1), the structural unit (a3-2) and the structural unit (a3-4).

When Resin (A) further comprises a structural unit (a4) and/or (a5), the structural unit represented by the formula (I) is present in an amount of usually 5% to 75% by mole, preferably 10% to 70% by mole, more preferably 10% to 65% by mole, and still more preferably 10% to 60% by mole.

Resin (A) can be produced according to known polymerization methods such as radical polymerization.

The resin has usually 2,000 or more of the weight-average molecular weight, preferably 2,500 or more of the weight-average molecular weight, more preferably 3,000 or more of the weight-average molecular weight. The resin has usually 50,000 or less of the weight-average molecular weight, more preferably 30,000 or less of the weight-average molecular weight, and more preferably 15,000 or less of the weight-average molecular weight.

The weight-average molecular weight can be measured with gel permeation chromatography.

<Photoresist Composition>

The photoresist composition of the disclosure comprises Resin (A) and an acid generator.

Preferably, the composition of the present disclosure may have another resin than Resin (A). Preferably, the composition further comprises a quencher and/or a solvent.

Another resin than Resin (A) comprises no structural unit (I).

Examples of another resin than Resin (A) include one which comprises no structural unit (I) but the structural unit (a1) [this resin is sometimes referred to as "Resin (A2)"], and one which consists of the structural unit (a4) or which consists of the structural unit (a4) and the structural unit (a5) [this resin is sometimes referred to as "Resin (X)"].

In Resin (X), the content of the structural unit (a4) is preferably 30% by mole or more, more preferably 40% by mole or more, still more preferably 45% by mole or more based on the sum of the structural units in the resin.

Resin (X) usually has 6000 or more of the weight-average molecular weight, preferably 7000 or more of the weight-average molecular weight. The resin usually has 80,000 or less of the weight-average molecular weight, preferably has 60,000 or less of the weight-average molecular weight.

The weight-average molecular weight can be measured with known methods such as liquid chromatography or gas chromatography.

When the photoresist composition contains Resin (X), the content of the resin is preferably 1 to 60 weight parts, more preferably 2 to 50 weight parts, and still more preferably 2 to 40 weight parts, further more preferably 1 to 30 weight parts, further still more preferably 1 to 8 weight parts, relative to 100 parts of Resin (A).

The total content of the resins in the photoresist composition of the present invention is usually 80% by mass or more, preferably 90% by mass or more, based on the sum of solid component, and usually 99% by mass or less based on the sum of solid component.

In this specification, "solid component" means components other than solvent in the photoresist composition.

The resin can be obtained by conducting polymerization reaction of the corresponding monomer or monomers. The polymerization reaction is usually carried out in the presence of a radical initiator.

This polymerization reaction can be conducted according to known methods.

<Acid Generator>

In the composition of the present disclosure can contain an acid generator known in the art.

The known acid generators may be an ionic acid generator or a nonionic acid generator.

Examples of the nonionic compounds for the acid generator include organic halogenated compounds; sulfonate esters such as 2-nitrobenzoate, aromatic sulfonates, oxime-sulfonate, N-sulfonyloxyimide, sulfonyloxyketone, and diazonaphtoquione 4-sulfonate; sulfones such as disulfone, ketosulfone, and sulfonium diazomethane. The ionic compounds for the acid generator include onium salts having an onium cation such as diazonium salts, phosphonium salts, sulfonium salts and iodonium salts. Examples of the anions of onium salt include a sulfonic acid anion, a sulfonylimide anion, sulfonylmethide anion.

As the acid generator, the compounds giving an acid by radiation can be used, which are mentioned in JPS63-26653A1, JPS55-164824A1, JPS62-69263A1, JPS63-146038A1, JPS63-163452A1, JPS62-153853A1, JPS63-146029A1, U.S. Pat. No. 3,779,778B1, U.S. Pat. No. 3,849,137B1, DE3914407 and EP126,712A1.

In the photoresist composition of the disclosure, the acid generator (B) may be used as a single salt or as a combination of two or more of salts.

The acid generator (B) is preferably a fluorine-containing compound, more preferably a salt represented by formula (B1):

(B1)

in which $Q^{b1}$ and $Q^{b2}$ independently each represent a fluorine atom or a C1-C6 perfluoroalkyl group, $L^{b1}$ represents a C1-C24 divalent saturated hydrocarbon group in which a methylene group can be replaced by —O— or —CO— and in which a hydrogen atom can be replaced by a fluorine atom or a hydroxyl group, Y represents a methyl group in which a hydrogen atom can be replaced by a substituent or a C3-C18 alicyclic hydrocarbon group in which a hydrogen atom can be replaced by a substituent and in which a methylene group has been replaced by —O—, —S(O)$_2$— or —CO—, and $Z^+$ represents an organic cation.

Hereinafter, the salt will be simply referred to as "salt (B1)".

For $Q^{b1}$ and $Q^{b2}$, examples of a perfluoroalkyl group include a trifluoromethyl group, a pentafluoroethyl group, a heptafluoropropyl group, a nonafluorobutyl group, an undecafluoropentyl group and a tridecafluorohexyl group, and a trifluoromethyl group is preferred.

$Q^{b1}$ and $Q^{b2}$ each independently preferably represent a fluorine atom or a trifluoromethyl group, and $Q^1$ and $Q^2$ are more preferably fluorine atoms.

For $L^{b1}$, examples of the divalent saturated hydrocarbon group include linear alkylene groups such as a methylene group, an ethylene group, a propane-1,3-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, an undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group and heptadecane-1,17-diyl group; branched alkylene groups such as an ethane-1,1-diyl group, a propane-1,1-diyl group, a propane-1,2-diyl group, a propane-2,2-diyl group, a pentane-2,4-diyl group, a2-methylpropane-1,3-diyl group, 2-methylpropane-1,2-diyl group, pentane-1,4-diyl group, and 2-methylbutane-1,4-diyl group;

divalent monocyclic alicyclic hydrocarbon groups such as cyclobutane-1,3-diyl group, cyclopentane-1,3-diyl group, cyclohexane-1,4-diyl group and cyclooctane-1,5-diyl group; and divalent polycyclic alicyclic hydrocarbon groups such as norbornane-1,4-diyl group, norbornane-2,5-diyl group, adamantane-1,5-diyl group and adamantane-2,6-diyl group.

For $L^{b1}$, examples of the saturated hydrocarbon group in which a methylene group has been replaced by an oxygen atom or a carbonyl group include those represented by formulae (b1-1), (b1-2) and (b1-3).

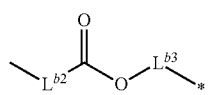

(b1-1)

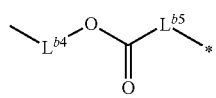

(b1-2)

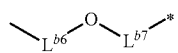

(b1-3)

In formula (b1-1), $L^{b2}$ represents a single bond or a C1-C22 divalent saturated hydrocarbon group where a hydrogen atom may be replaced by a fluorine atom, and $L^{b3}$ represents a single bond or a C1-C22 divalent saturated hydrocarbon group where a hydrogen atom may be replaced by a hydroxyl group or a fluorine atom and where a methylene group may be replaced by an oxygen atom or carbonyl group, provided that total number of the carbon atoms of $L^{b2}$ and $L^{b3}$ is up to 22.

In formula (b1-2), $L^{b4}$ represents a C1-C22 divalent saturated hydrocarbon group where a hydrogen atom may be replaced by a fluorine atom, and $L^{b5}$ represents a single bond or a C1-C22 divalent saturated hydrocarbon group where a hydrogen atom may be replaced by a hydroxyl group or a fluorine atom and where a methylene group may be replaced by an oxygen atom or carbonyl group, provided that the total carbon atoms of $L^{b4}$ and $L^{b5}$ is up to 22.

In formula (b1-3), $L^{b6}$ represents a single bond or a C1-C23 divalent saturated hydrocarbon group where a hydrogen atom may be replaced by a fluorine atom, and $L^{b7}$ represents a single bond or a C1-C22 divalent saturated hydrocarbon group where a hydrogen atom may be replaced by a hydroxyl group or a fluorine atom and where a methylene group may be replaced by an oxygen atom or carbonyl group, with the proviso that total carbon number of $L^{b6}$ and $L^{b7}$ is up to 23 and with the proviso that formula (b1-3) excludes a group having a structure represented by -$L^{b6}$-O—CO—.

In these formulae, * represents a binding position to Y.

In formulae (b1-1), (b1-2) and (b1-3), the divalent saturated hydrocarbon group includes linear chain alkanediyl groups, branched chain alkanediyl groups, monocyclic or polycyclic divalent saturated hydrocarbon groups, and a group combining two or more of the above-mentioned groups.

$L^{b2}$ is preferably a single bond.

$L^{b3}$ is preferably a C1-C4 divalent saturated hydrocarbon group.

$L^{b4}$ is preferably a C1-C8 divalent saturated hydrocarbon group where a hydrogen atom may be replaced by a fluorine atom.

$L^{b5}$ is preferably a single bond or a C1-C8 divalent saturated hydrocarbon group.

$L^{b6}$ is preferably a single bond or a C1-C4 divalent saturated hydrocarbon group where a hydrogen atom may be replaced by a fluorine atom.

$L^{b7}$ is preferably a single bond or a C1-C7 divalent saturated hydrocarbon group where a hydrogen atom may be replaced by a hydroxyl group or a fluorine atom and where a methylene group may be replaced by an oxygen atom or carbonyl group.

Examples of the group represented by formula (b1-1) include those represented by formulae (b1-4), (b1-5), (b1-6), (b1-7) and (b1-8)

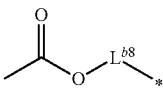

(b1-4)

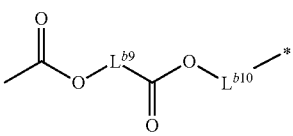

(b1-5)

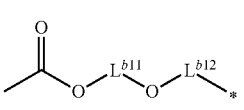

(b1-6)

(b1-7)
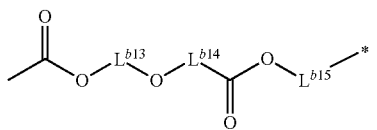

(b1-8)
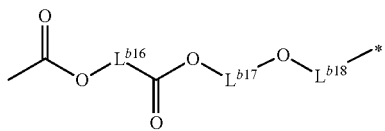

In formula (b1-4), $L^{b8}$ represents a single bond or a C1-C22 divalent saturated hydrocarbon group where a hydrogen atom may be replaced by a fluorine atom or a hydroxyl group.

In formula (b1-5), $L^{b9}$ represents a C1-C20 divalent saturated hydrocarbon group, and $L^{b10}$ represents a single bond or a C1-C19 divalent saturated hydrocarbon group where a hydrogen atom may be replaced by a hydroxyl group or a fluorine atom, provided that the total carbon atoms of $L^{b10}$ and $L^{b9}$ is up to 20.

In formula (b1-6), $L^{b11}$ represents a C1-C21 divalent saturated hydrocarbon group, and $L^{b12}$ represents a single bond or a C1-C20 divalent saturated hydrocarbon group where a hydrogen atom may be replaced by a hydroxyl group or a fluorine atom, with the proviso that total carbon number of $L^{b11}$ and $L^{b12}$ is up to 21.

In formula (b1-7), $L^{b13}$ represents a C1-C19 divalent saturated hydrocarbon group, $L^{b14}$ represents a single bond or a C1-C18 divalent saturated hydrocarbon group, and $L^{b15}$ represents a single bond or a C1-C18 divalent saturated hydrocarbon group where a hydrogen atom may be replaced by a hydroxyl group or a fluorine atom, with the proviso that total carbon number of $L^{b13}$, $L^{b14}$ and $L^{b15}$ is up to 19.

In formula (b1-8), $L^{b16}$ represents a C1-C18 divalent saturated hydrocarbon group, $L^{b17}$ represents a C1-C18 divalent saturated hydrocarbon group, and $L^{b18}$ represents a single bond or a C1-C17 divalent saturated hydrocarbon group where a hydrogen atom may be replaced by a hydroxyl group or a fluorine atom, with the proviso that total carbon number of $L^{b16}$, $L^{b17}$ and $L^{b18}$ is up to 19.

In these formulae, * represents a binding position, * represents a binding position to Y.

In these formulae, the divalent saturated hydrocarbon group includes linear chain alkanediyl groups, branched chain alkanediyl groups, monocyclic or polycyclic divalent saturated hydrocarbon groups, and a group combining two or more of the above-mentioned groups.

Specific examples of the divalent saturated hydrocarbon group include those as referred to for $L^{b1}$.

$L^{b8}$ is preferably a C1-C4 alkanediyl group.

$L^{b9}$ is preferably a C1-C8 divalent saturated hydrocarbon group.

$L^{b10}$ is preferably a single bond or a C1-C19 divalent saturated hydrocarbon group, and more preferably a single bond or a C1-C8 divalent saturated hydrocarbon group.

$L^{b11}$ is preferably a C1-C8 divalent saturated hydrocarbon group.

$L^{b12}$ is preferably a single bond or a C1-C8 divalent saturated hydrocarbon group.

$L^{b13}$ is preferably a C1-C12 divalent saturated hydrocarbon group.

$L^{b14}$ is preferably a single bond or a C1-C6 divalent saturated hydrocarbon group.

$L^{b15}$ is preferably a single bond or a C1-C18 divalent saturated hydrocarbon group, and more preferably a single bond or a C1-C8 divalent saturated hydrocarbon group.

$L^{b16}$ is preferably a C1-C12 divalent saturated hydrocarbon group.

$L^{b17}$ is preferably a C1-C6 divalent saturated hydrocarbon group.

$L^{b18}$ is preferably a single bond or a C1-C17 divalent saturated hydrocarbon group, and more preferably a single bond or a C1-C4 divalent saturated hydrocarbon group.

Examples of the group represented by formula (b1-3) include those represented by formulae (b1-9), (b1-10) and (b1-11).

(b1-9)
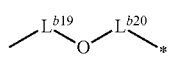

(b1-10)
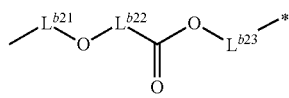

(b1-11)
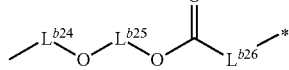

In formula (b1-9), $L^{b19}$ represents a single bond or a C1-C23 divalent saturated hydrocarbon group where a hydrogen atom may be replaced by a fluorine atom, and $L^{b20}$ represents a single bond or a C1-C23 divalent saturated hydrocarbon group where a hydrogen atom may be replaced by a hydroxyl group or a fluorine atom and where a methylene group may be replaced by an oxygen atom or carbonyl group, provided that the total carbon atoms of $L^{b19}$ and $L^{b20}$ is up to 23. In formula (b1-10), $L^{b21}$ represents a single bond or a C1-C21 divalent saturated hydrocarbon group where a hydrogen atom may be replaced by a fluorine atom, $L^{b22}$ represents a single bond or a C1-C21 divalent saturated hydrocarbon group and $L^{b23}$ represents a single bond or a C1-C21 divalent saturated hydrocarbon group where a hydrogen atom may be replaced by a hydroxyl group or a fluorine atom and where a methylene group may be replaced by an oxygen atom or a carbonyl group, provided that the total carbon atoms of $L^{b21}$, $L^{b22}$ and $L^{b23}$ is up to 21.

In formula (b1-11), $L^{b24}$ represents a C1-C21 divalent saturated hydrocarbon group where a hydrogen atom may be replaced by a fluorine atom, $L^{b25}$ represents a C1-C21 divalent saturated hydrocarbon group, and $L^{b26}$ represents a single bond or a C1-C20 divalent saturated hydrocarbon group where a hydrogen atom may be replaced by a hydroxyl group or a fluorine atom and where a methylene group may be replaced by an oxygen atom or a carbonyl group, provided that the total carbon atoms of $L^{b24}$, $L^{b25}$ and $L^{b26}$ is up to 21.

In these formulae,* represents a binding position to Y.

In these formulae, the divalent saturated hydrocarbon group includes linear chain alkanediyl groups, branched chain alkanediyl groups, monocyclic or polycyclic divalent saturated hydrocarbon groups, and a group combining two or more of the above-mentioned groups.

Specific examples of the divalent saturated hydrocarbon group include those as referred to for $L^{b1}$.

Examples of the divalent saturated hydrocarbon group where a methylene group has been replaced by an oxygen atom or a carbonyl group include what has an acyloxy group. In what has an acyloxy group, a hydrogen atom may be replaced by a hydroxyl group and a methylene group may be replaced by an oxygen atom or a carbonyl group.

Examples of what has an acyloxy group include an acetyloxy group, a propionyloxy group, a butyryloxy group, a cyclohexylcarbonyloxy group and an adamantylcarbonyloxy group.

When a hydrogen atom has been replaced by a hydroxyl group or a methylene group has been replaced by an oxygen atom or a carbonyl group in what has an acyloxy group, examples of such a group include an oxoadamantylcarbonyloxy group, a hydroxyadamantylcarbonyloxy group, an oxocyclohexylcarbonyloxy group, and a hydroxycyclohexylcarbonyloxy group.

Examples of the group represented by formula (b1-4) include the following ones.

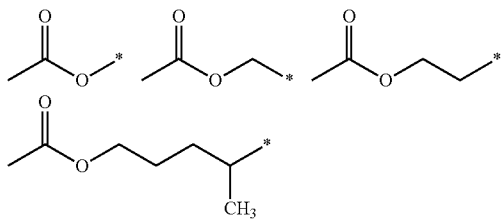

Examples of the group represented by formula (b1-5) include the following ones.

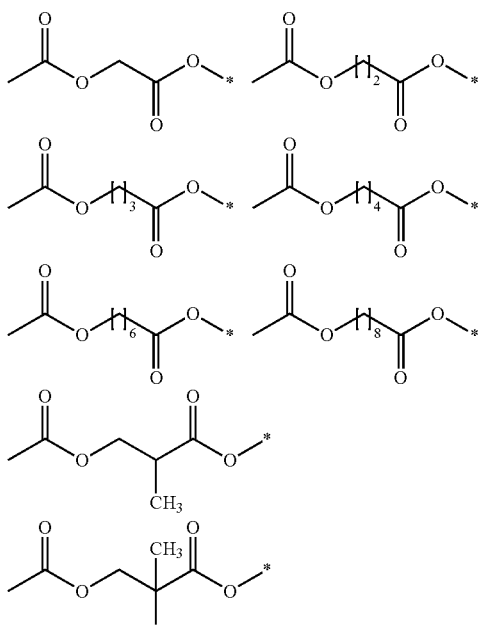

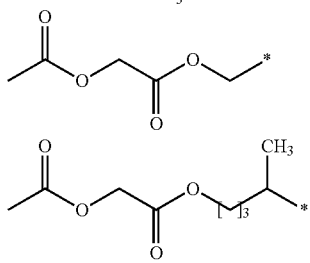

-continued

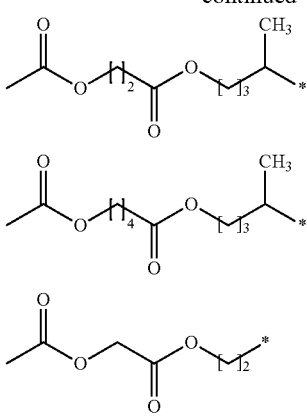

Examples of the group represented by formula (b1-6) include the following ones.

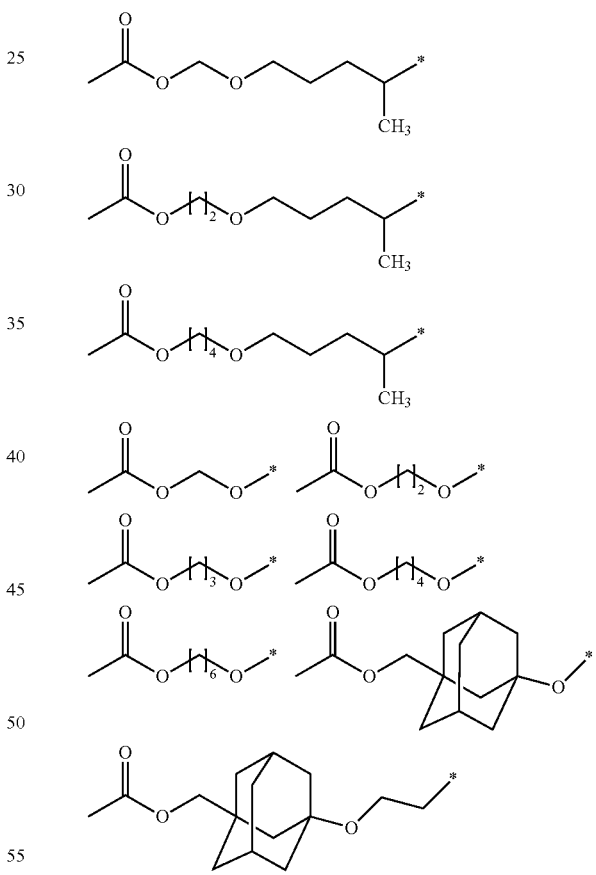

Examples of the group represented by formula (b1-7) include the following ones.

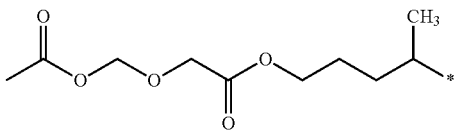

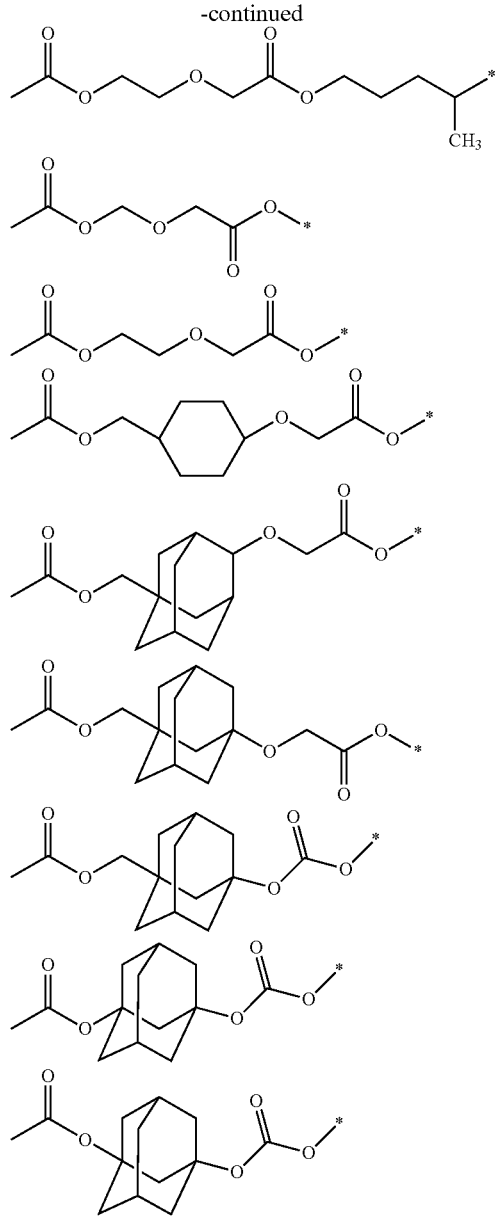
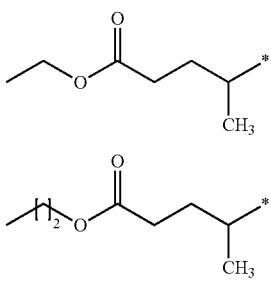
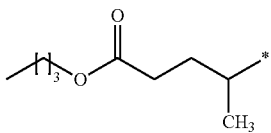
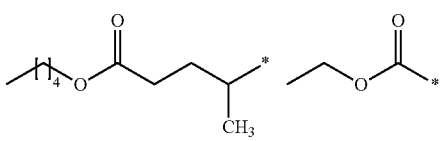
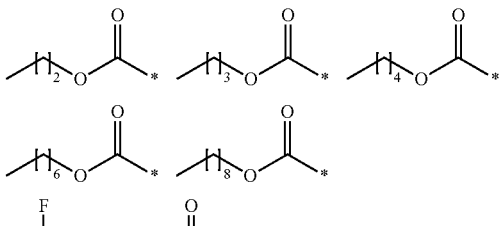
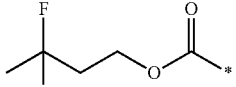
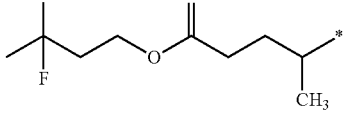
Examples of the group represented by formula (b1-8) include the following ones.
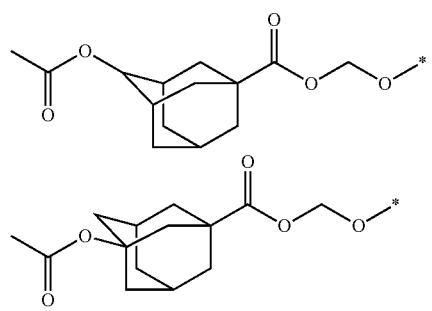
Examples of the group represented by formula (b1-2) include the following ones.
Examples of the group represented by formula (b1-9) include the following ones.
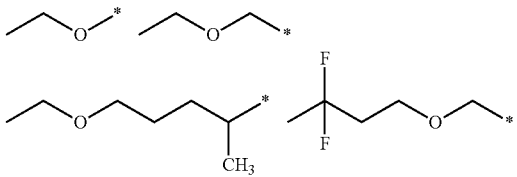
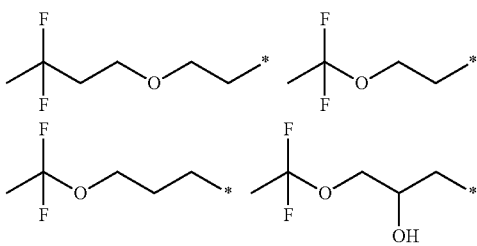

-continued
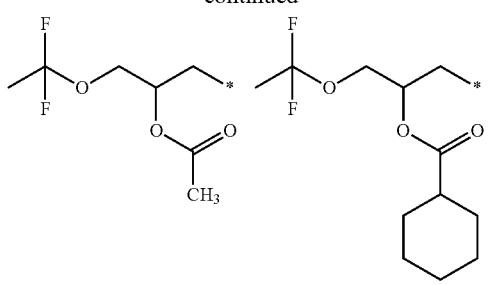
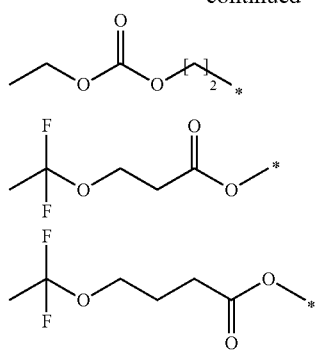
Examples of the group represented by formula (b1-10) include the following ones.
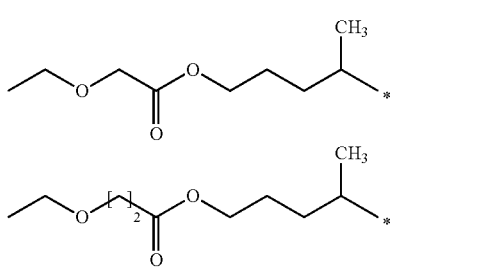
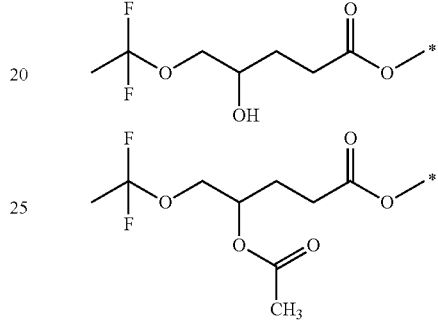
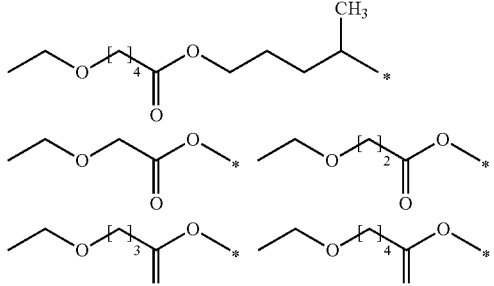
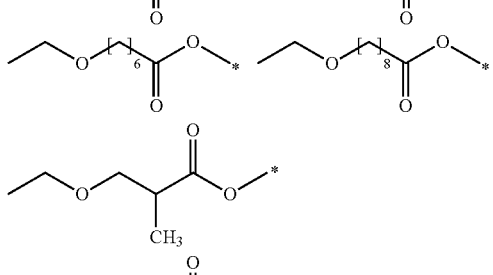
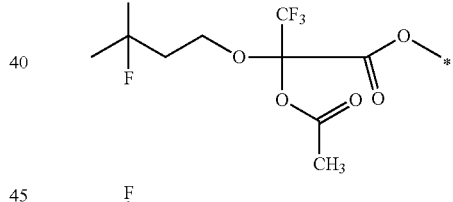
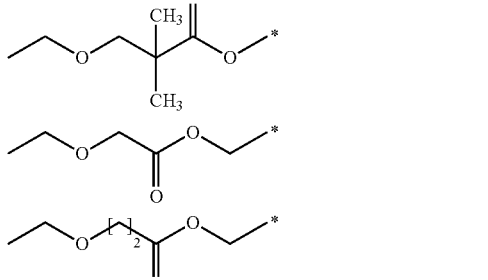
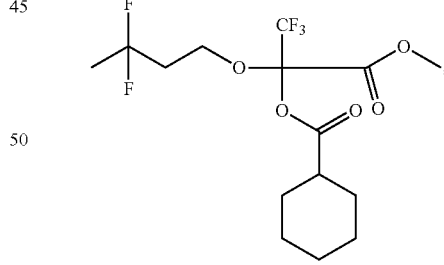
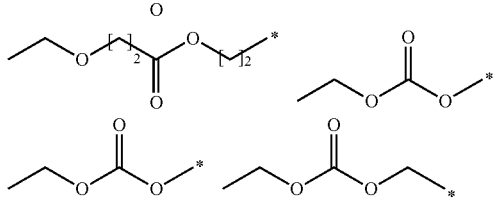
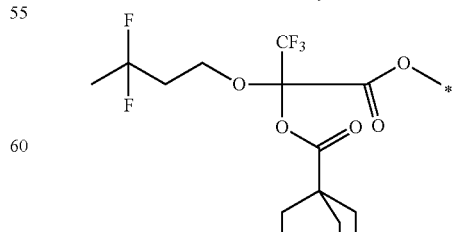

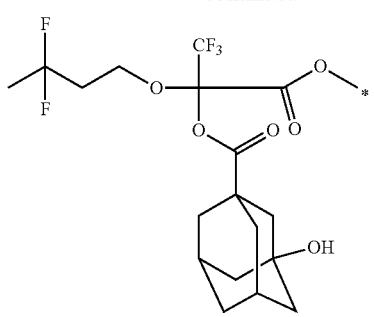
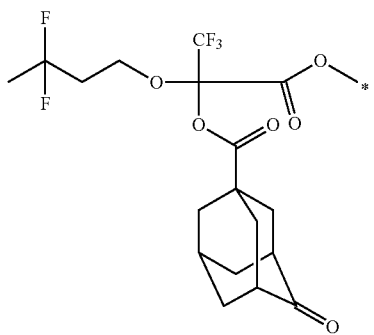
Examples of the group represented by formula (b1-11) include the following ones.
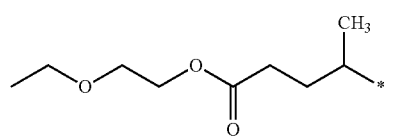
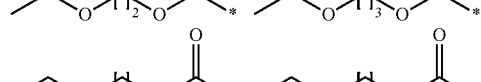
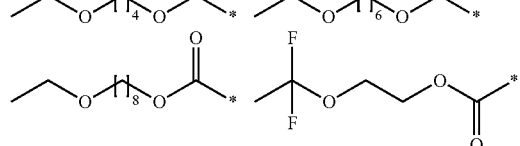
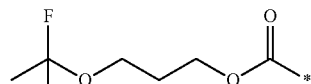
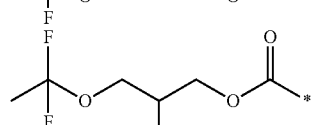
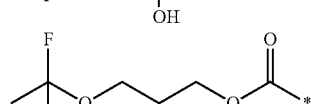
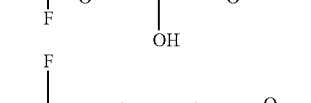
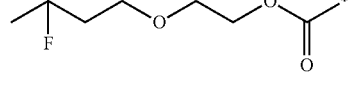
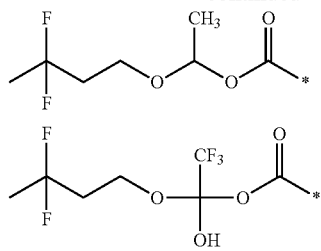
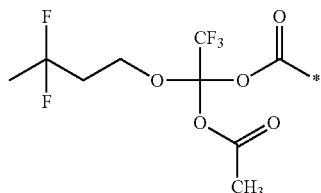
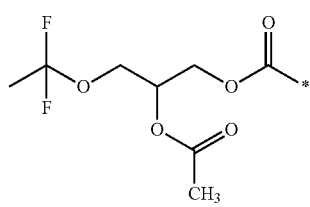

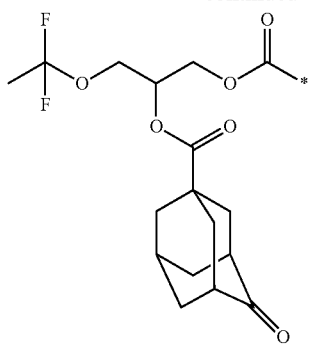

$L^{b1}$ is preferably one represented by formula (b1-1) or (b1-2), more preferably one represented by formula (b1-1) or (b1-2) in which $L^{b2}$ is a single bond or $L^{b4}$ is a C1-C4 divalent alkanediyl group in which a hydrogen atom can be replaced by a fluorine atom, more preferably one represented by formula (b1-4).

The monovalent alicyclic hydrocarbon group for Y may be a monocyclic one or polycyclic one such as a spiro ring.

Preferred examples of the alicyclic hydrocarbon group represented by Y include those represented by the formulae (Y1) to (Y11) and (Y36) to (Y38). Preferred examples of the alicyclic hydrocarbon group which is represented by Y and in which a methylene group has been replaced by —O—, —SO₂— or —CO— include those represented by the formulae (Y12) to (Y35) and Y(39) and Y(40).

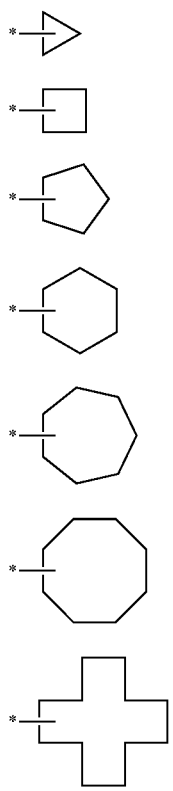

(Y1)
(Y2)
(Y3)
(Y4)
(Y5)
(Y6)
(Y7)

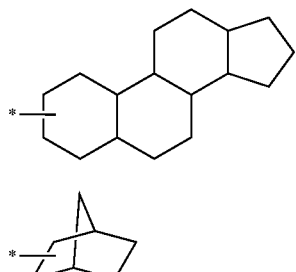 (Y8)

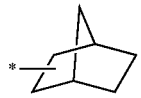 (Y9)

 (Y10)

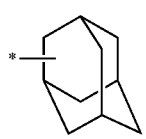 (Y11)

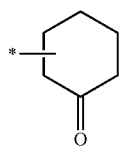 (Y12)

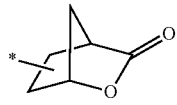 (Y13)

 (Y14)

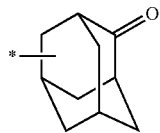 (Y15)

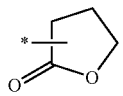 (Y16)

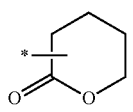 (Y17)

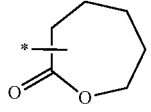 (Y18)

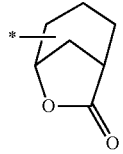 (Y19)

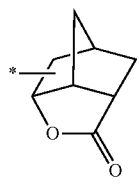 (Y20)
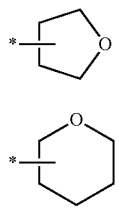 (Y21)
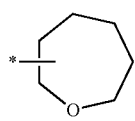 (Y22)
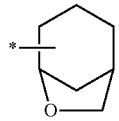 (Y23)
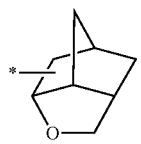 (Y24)
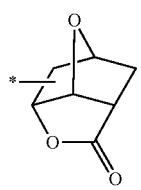 (Y25)
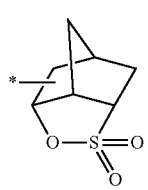 (Y26)
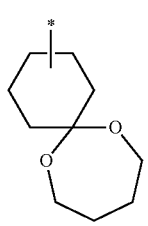 (Y27)
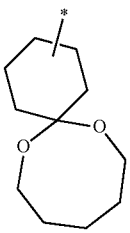 (Y28)
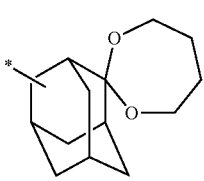 (Y29)
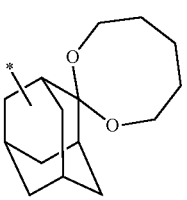 (Y30)
 (Y31)
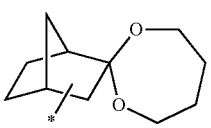 (Y32)
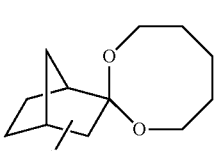 (Y33)
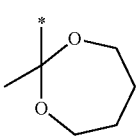 (Y34)
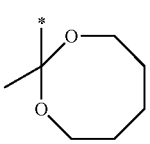 (Y35)
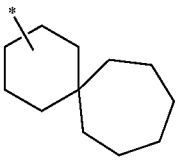 (Y36)
(Y37)

-continued

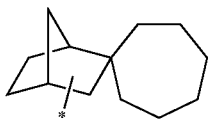
(Y38)

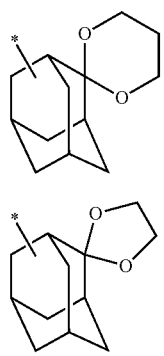
(Y39)

(Y40)

Among the groups represented by the formulae, preferred are those represented by formulae (Y1) to (Y20), (Y30), (Y31), (Y39) and (Y40); more preferred are those represented by the formulae (Y11), (Y15), (Y16), (Y19), (Y20), (Y30), (Y31), (Y39) and (Y40); and still more preferred are those represented by the formulae (Y11), (Y15), (Y30), (Y39) and (Y40).

Substituents on the methyl group for Y include a halogen atom, a hydroxyl group, a C3-C16 alicyclic hydrocarbon group, a C6-C18 aromatic hydrocarbon group, a glycidyloxy group, and —$(CH_2)_{j2}$—O—CO—$R^{b1'}$— in which $R^{b1'}$ is a C1-C16 alkyl group and j2 is an integer of 0 to 4.

Substituents on the alicyclic hydrocarbon groups for Y include a halogen atom, a hydroxyl group, a C1-C12 alkyl group, a C1-C12 hydroxy-containing alkyl group, a C1-C12 alkoxy group, a C3-C16 alicyclic hydrocarbon group, a C6-C18 aromatic hydrocarbon group, a C7-C21 aralkyl group, a C2-C4 acyl group, a glycidyloxy group, and —$(CH_2)_{j2}$—O—CO—$R^{b1'}$— in which $R^{b1'}$ is a C1-C16 alkyl group and j2 is an integer of 0 to 4.

Examples of the halogen atom include a fluorine atom, a chlorine atom, a bromine atom and an iodine atom.

Examples of the alicyclic hydrocarbon group include a cyclopentyl group, a cyclohexyl group, a cycloheptyl group and a cyclooctyl group, a norbornyl group and an adamantyl group.

Examples of the aromatic hydrocarbon group include an aryl group such as a phenyl group, a naphthyl group, an anthryl group, a p-methylphenyl group, a p-tert-butylphenyl group, a p-adamantylphenyl group, a tolyl group, a xylyl group, a cumyl group, a mesityl group, a biphenyl group, a phenanthryl group, a 2,6-diethylphenyl group and a 2-methyl-6-ethylphenyl group.

Examples of the alkyl group include a methyl group, an ethyl group, a propyl group, an isopropyl group, a butyl group, a sec-butyl group, a tert-butyl group, a pentyl group, a hexyl group, a heptyl group, a 2-ethylhexyl group and a dodecyl group.

Examples of hydroxyl-containing alkyl group include a hydroxymethyl group and a hydroxyethyl group.

Examples of the C1-C12 alkoxy group include a methoxy group, an ethoxy group, a propoxy group, a butoxy group, a pentyloxy group, a hexyloxy group, a heptyloxy group, an octyloxy group, a decyloxy group and a dodecyloxy group.

Examples of the aralkyl group include a benzyl group, phenylpropyl group, a phenethyl group, a naphthylmethyl group, or a naphthylethyl group.

Examples of the acyl group include an acetyl group, a propionyl group and a butyryl group.

Examples of Y include the groups as follow.

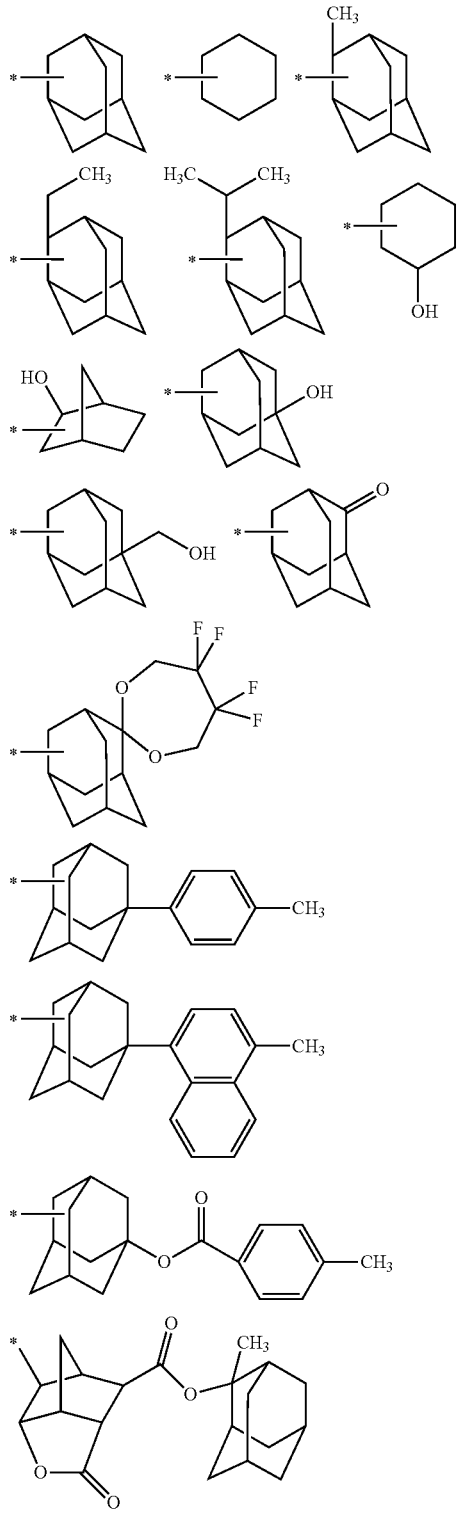

-continued
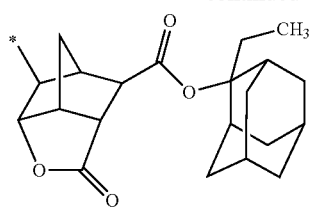
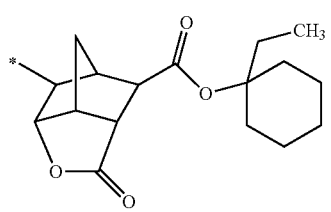
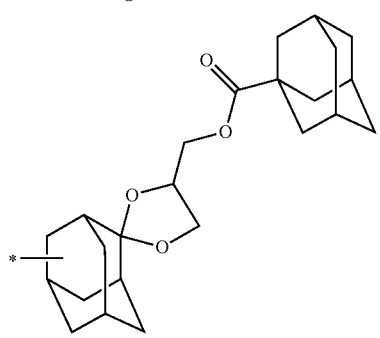
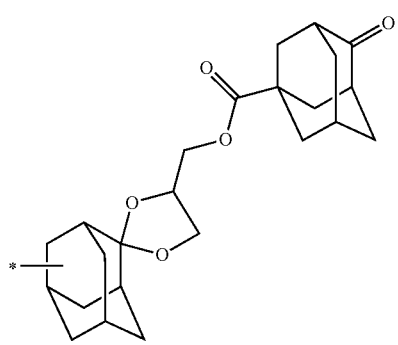
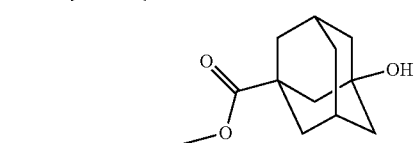
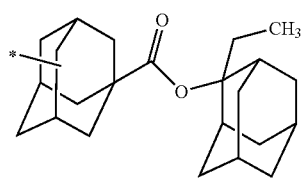
-continued
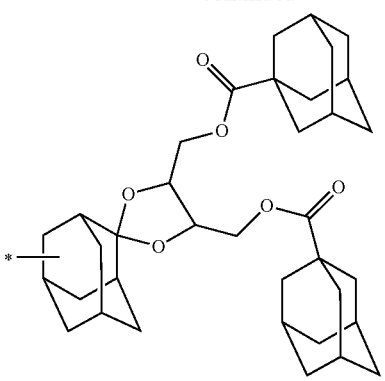
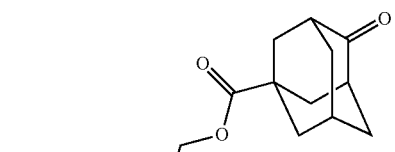
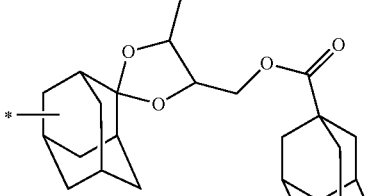
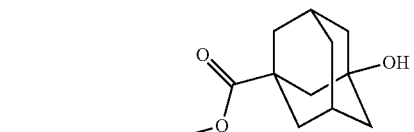
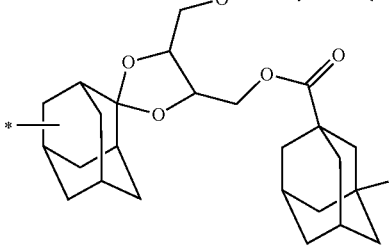
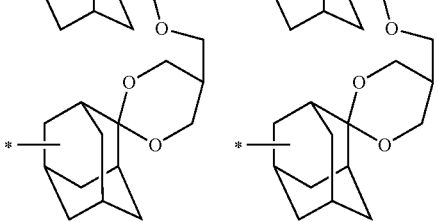

123
-continued

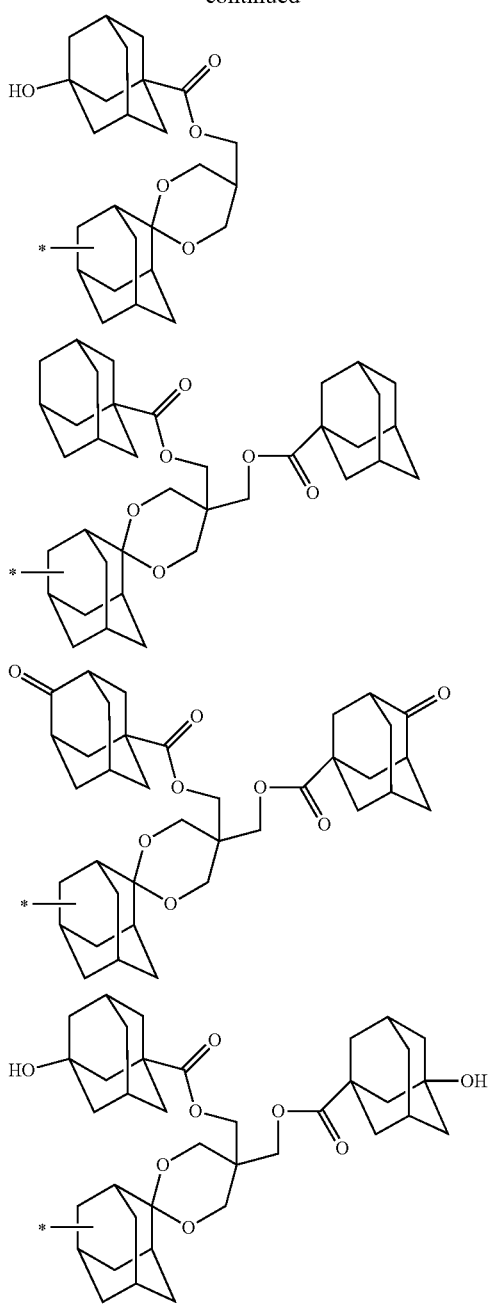

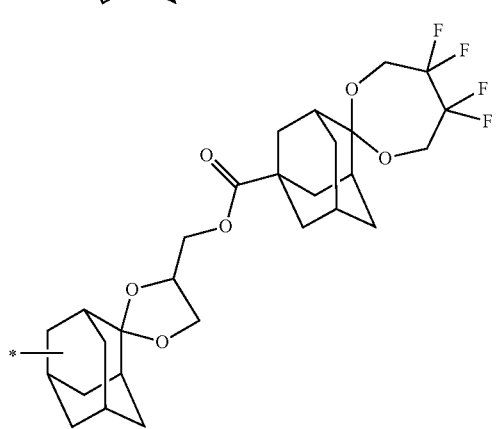

124
-continued

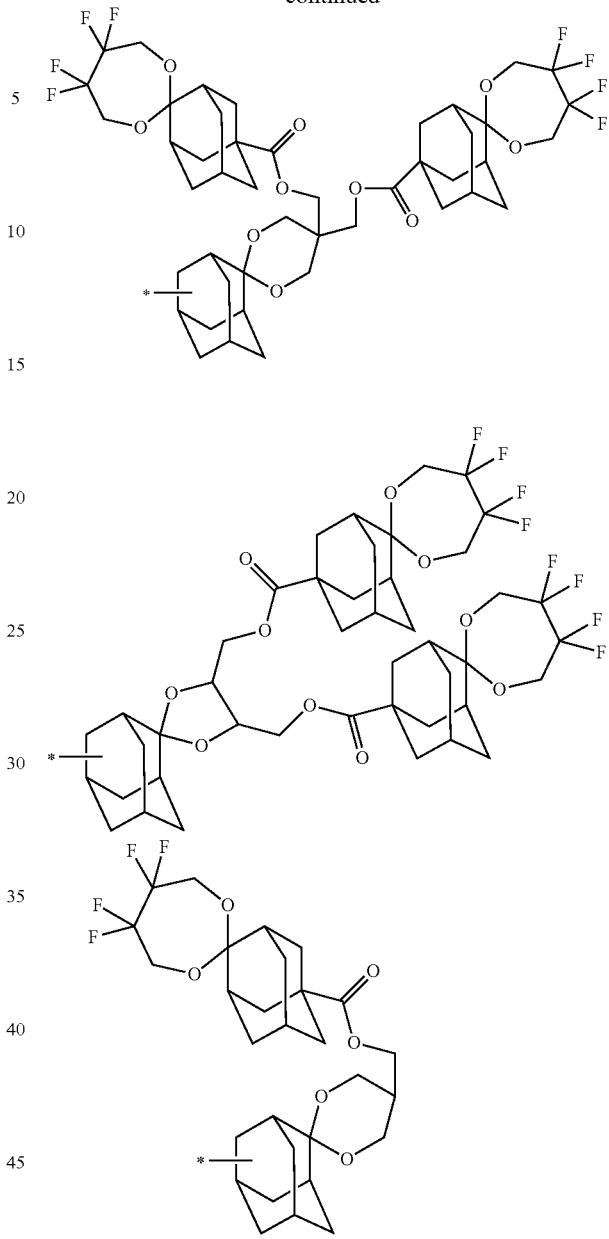

Y represents preferably a C3-C18 alicyclic hydrocarbon group which may have a substituent and in which a methylene group has been replaced by —O—, —SO$_2$— or —CO—, more preferably an adamantyl group which may have a substituent and in which a methylene group has been replaced by —O—, —SO$_2$— or —CO—, and still more preferably an adamantyl group, a hydroxyadamantyl group, an oxoadamantyl group, or the following groups.

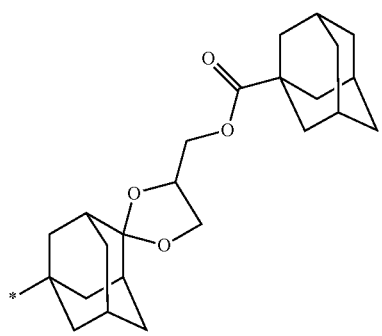
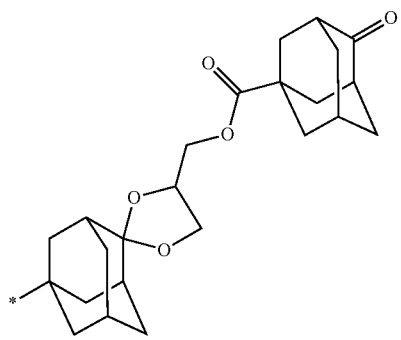
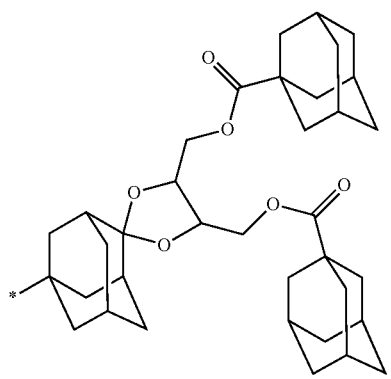
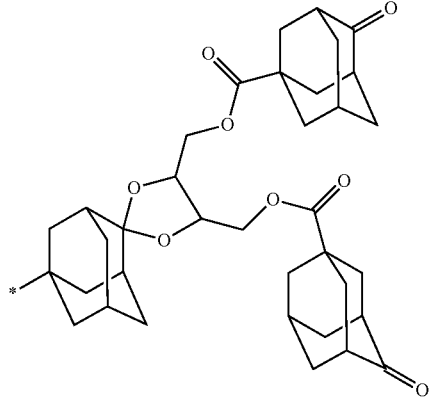
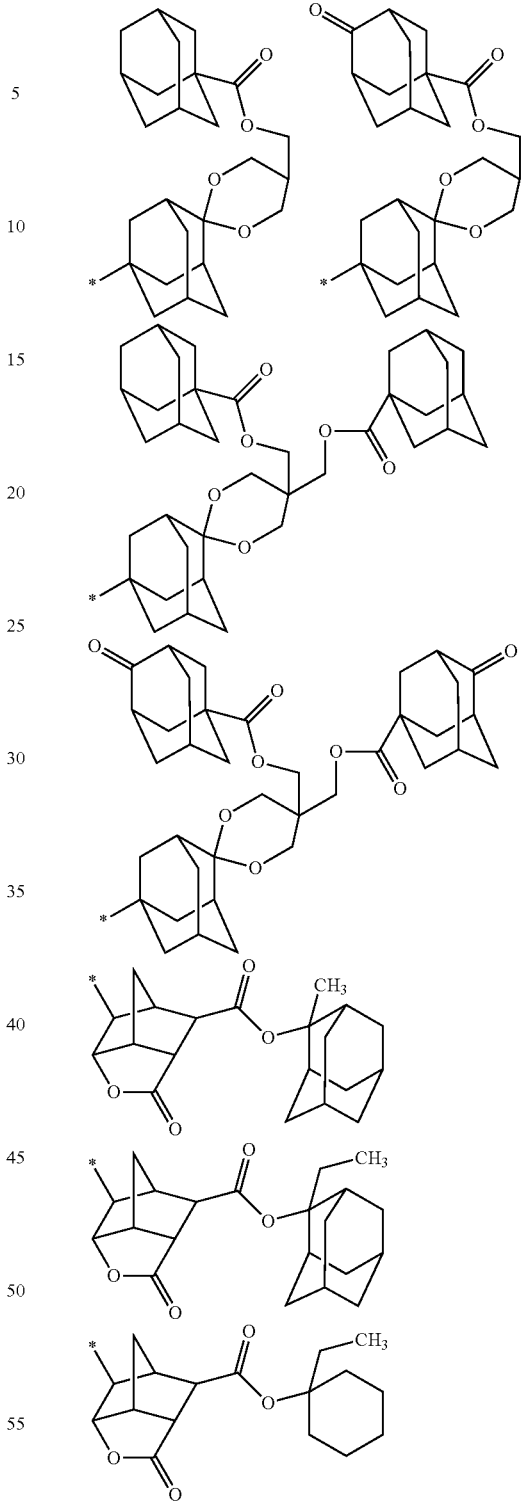
where * represents a binding position.
Preferred examples of the sulfonic acid anion of the salt represented by formula (B1) include salts represented by the formulae (B1-A-1) to (B1-A-55), preferably the formulae (B1-A-1) to (B1-A-4), (B1-A-9), (B1-A-1a), (B1-A-24) to (B1-A-33), (B1-A-36) to (B1-A-40) and (B1-A-47) to (B1-A-55).

(B1-A-1) 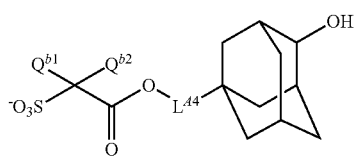
(B1-A-2) 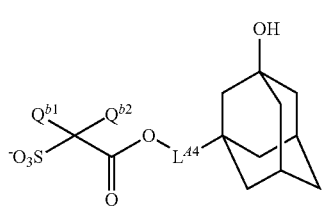
(B1-A-3) 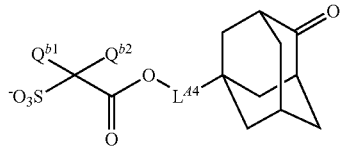
(B1-A-4) 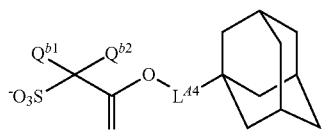
(B1-A-5) 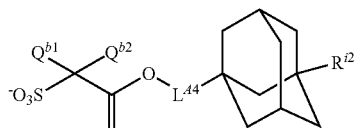
(B1-A-6) 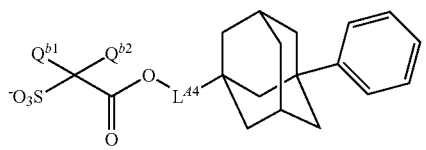
(B1-A-7) 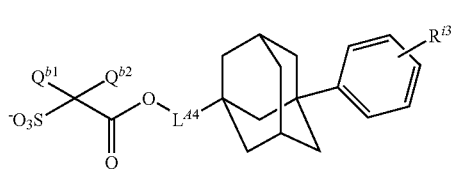
(B1-A-8) 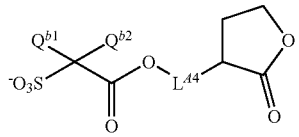
(B1-A-9) 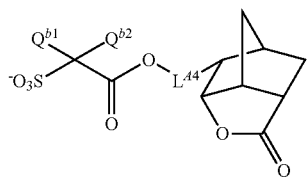
-continued
(B1-A-10) 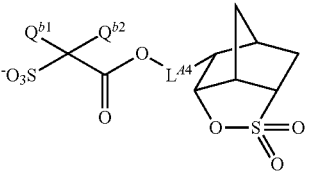
(B1-A-11) 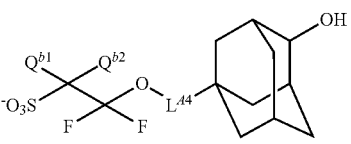
(B1-A-12) 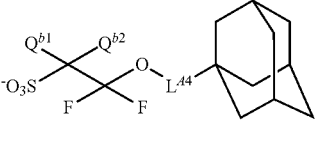
(B1-A-13) 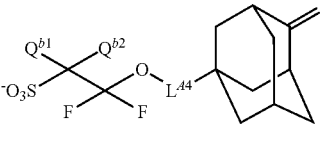
(B1-A-14) 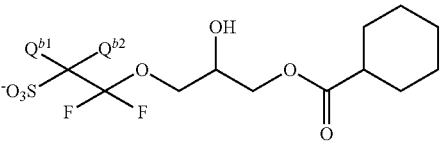
(B1-A-15) 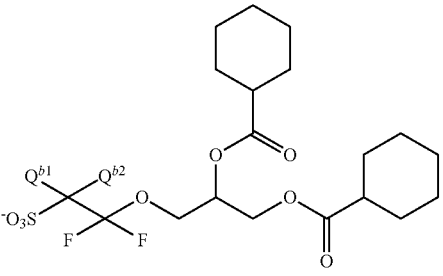
(B1-A-16) 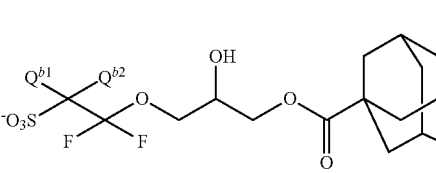
(B1-A-17) 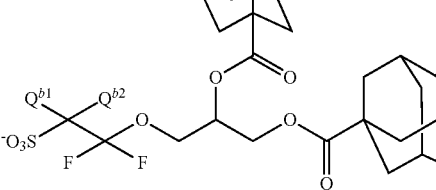

(B1-A-18)
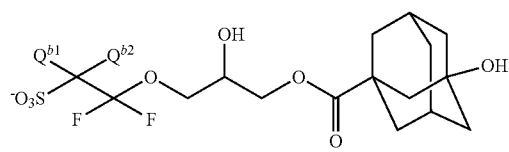
(B1-A-19)
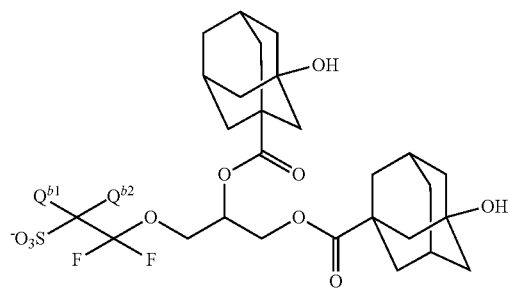
(B1-A-20)
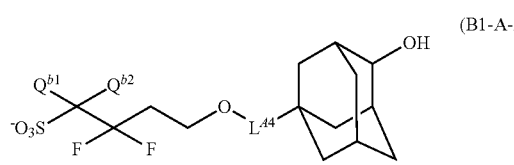
(B1-A-21)
(B1-A-22)
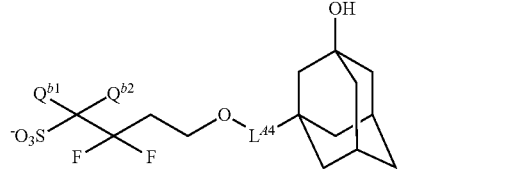
(B1-A-23)
(B1-A-24)
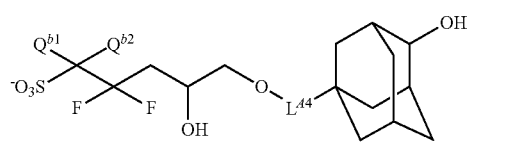
(B1-A-25)
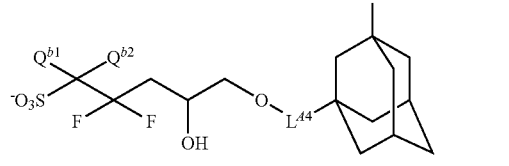
(B1-A-26)
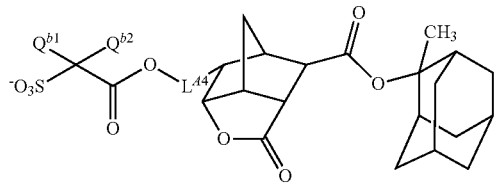
(B1-A-27)
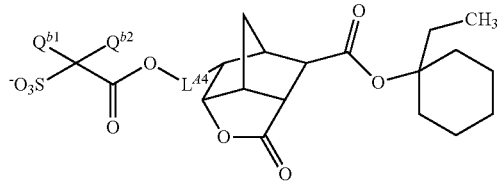
(B1-A-28)
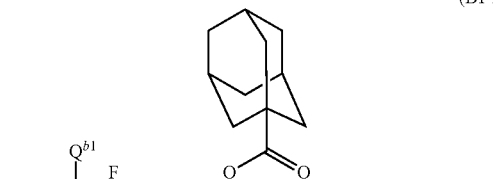
(B1-A-29)
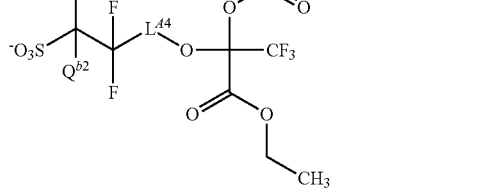
(B1-A-30)
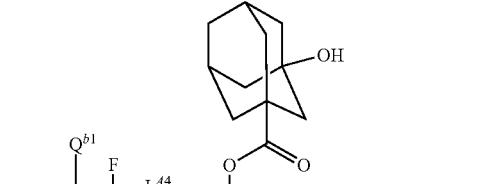
(B1-A-31)
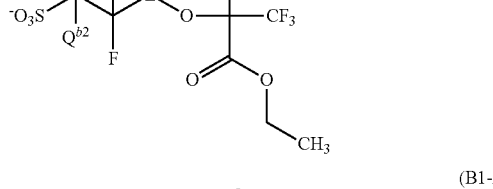

-continued (B1-A-32)
(B1-A-33)
(B1-A-34)
(B1-A-35)
(B1-A-36)
(B1-A-37)
(B1-A-38)

(B1-A-39)
(B1-A-40)
(B1-A-41)
(B1-A-42)
(B1-A-43)
(B1-A-44)
(B1-A-45)
(B1-A-46)

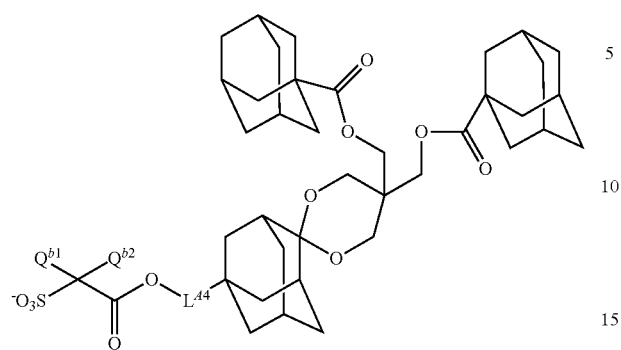
(B1-A-47)
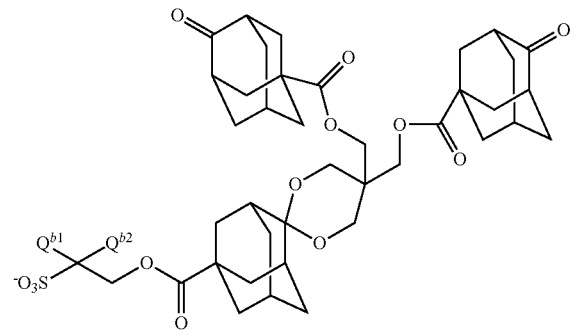
(B1-A-51)
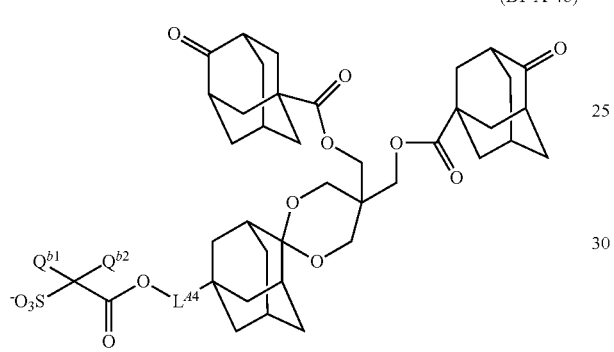
(B1-A-48)
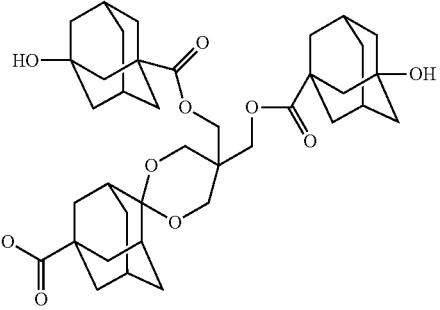
(B1-A-52)
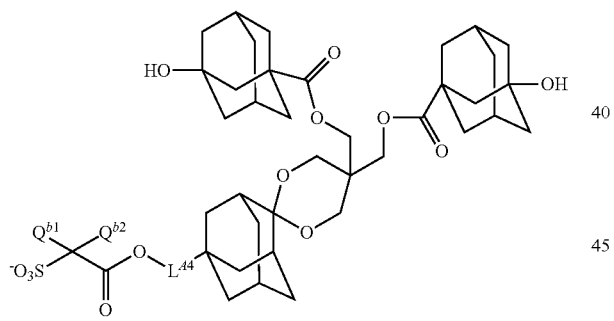
(B1-A-49)
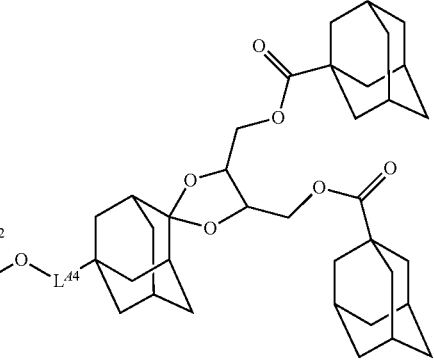
(B1-A-53)
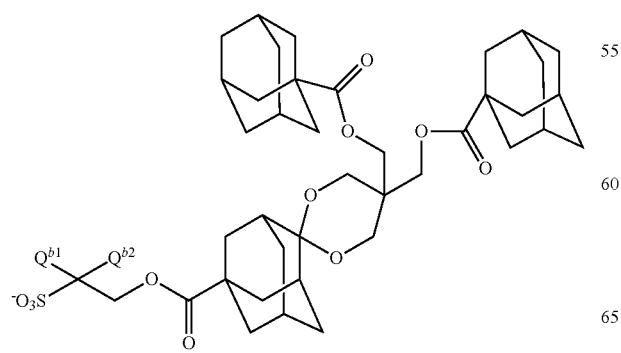
(B1-A-50)
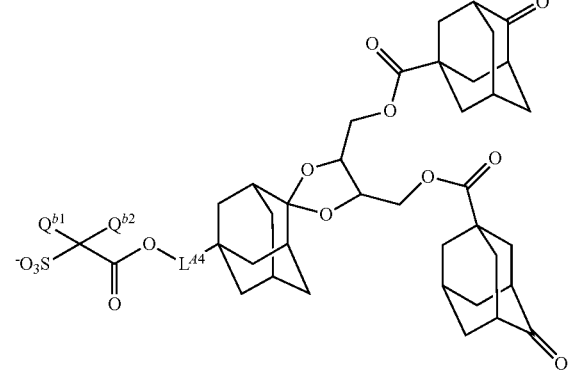
(B1-A-54)

-continued (B1-A-55)
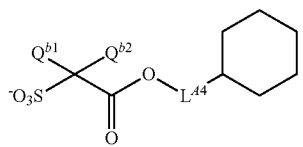

In these formulae, the symbols $Q^{b1}$ and $Q^{b2}$ are defined as above, $R^{i2}$, $R^{i3}$, $R^{i4}$, $R^{i5}$, $R^{i6}$ and $R^{i7}$ each independently represent a C1-C4 alkyl group, preferably a methyl group or an ethyl group, $R^{i8}$ represents a C1-C12 aliphatic hydrocarbon group [preferably a C1-C4 alkyl group], a C5-C12 monovalent alicyclic hydrocarbon group, or a combined group of them, preferably a methyl group, an ethyl group, a cyclohexyl group or an adamantyl group, and $L^{A4}$ represents a single bond or a C1-C4 alkanediyl group.

Examples of the sulfonic acid anion of the salt represented by formula (B1) include those described in JP2010-2046465A1.

Specific examples of the sulfonic acid anion of the salt represented by formula (B1) include the following anions.

(B1a-1)
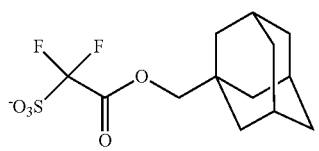

(B1a-2)
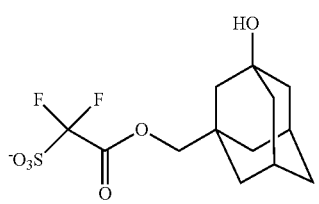

(B1a-3)
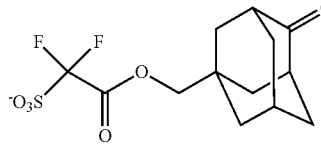

(B1a-4)
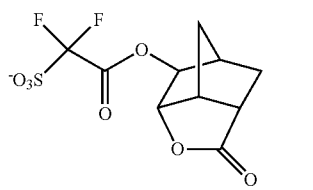

(B1a-5)
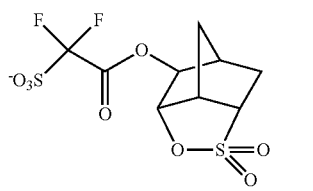

(B1a-6)
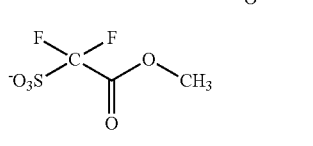

(B1a-7)
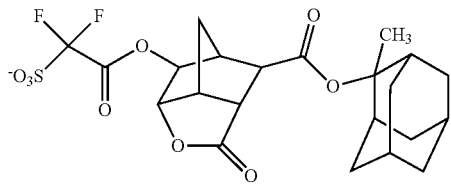

(B1a-8)
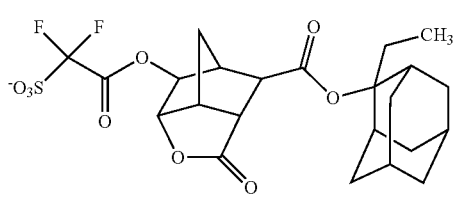

(B1a-9)
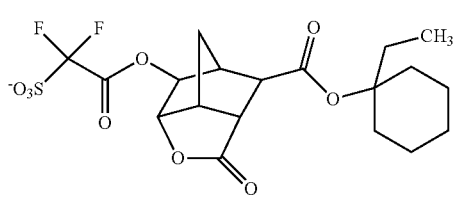

(B1a-10)

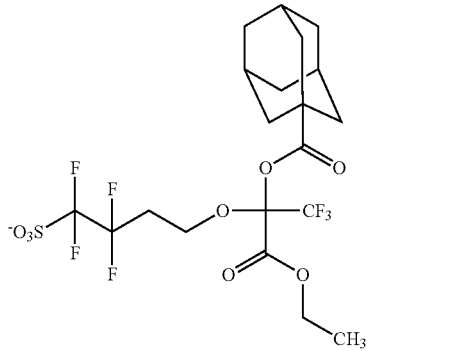

(B1a-11)
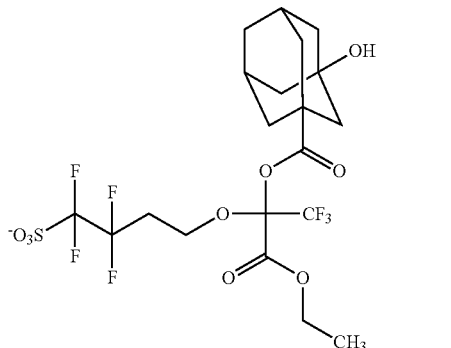

(B1a-12)
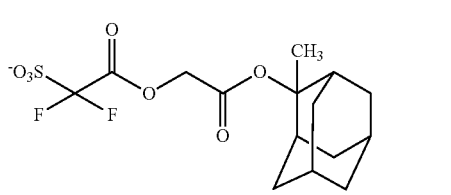

(B1a-13)
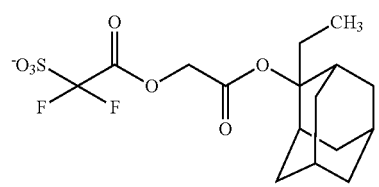
(B1a-14)
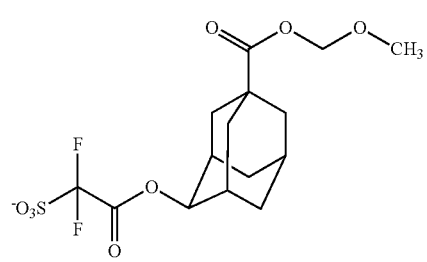
(B1a-15)
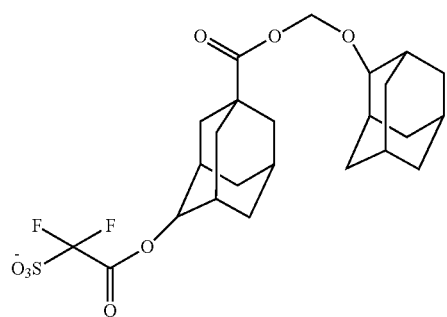
(B1a-16)
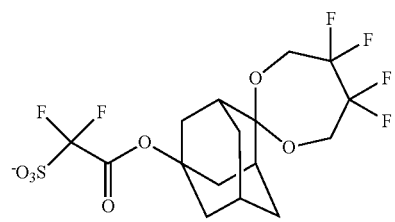
(B1a-17)
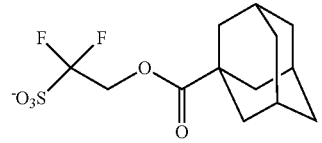
(B1a-18)
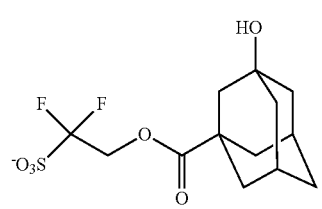
(B1a-19)
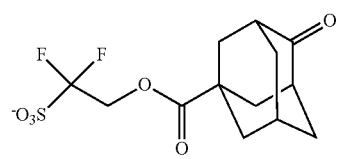
(B1a-20)
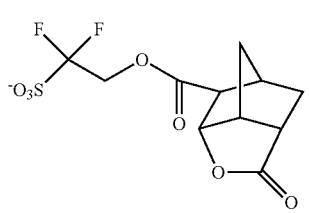
(B1a-21)
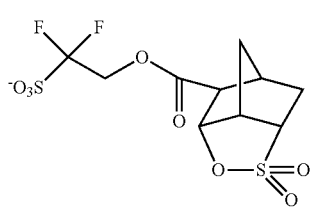
(B1a-22)
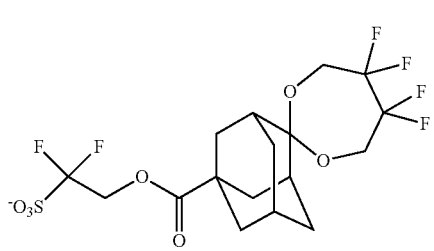
(B1a-23)
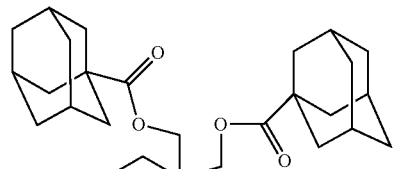
(B1a-24)
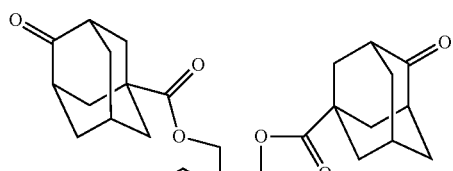

(B1a-25)
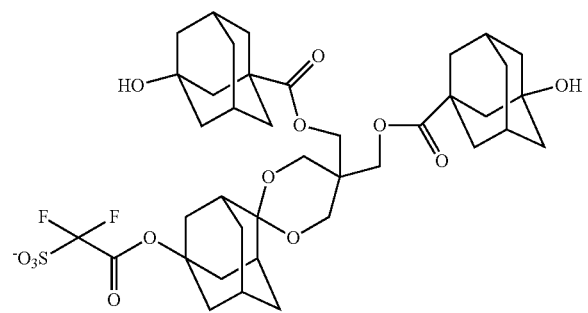
(B1a-29)
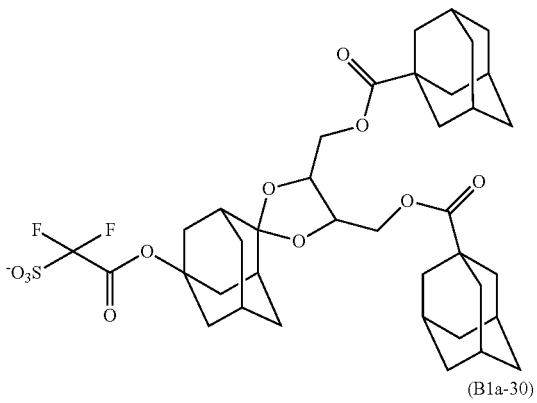
(B1a-26)
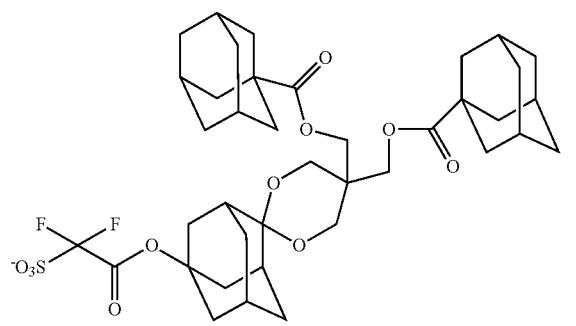
(B1a-30)
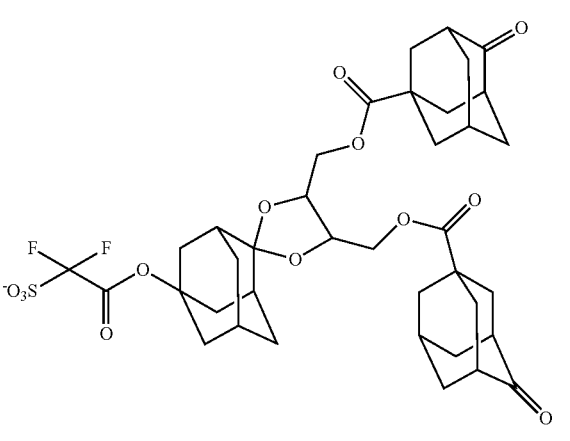
(B1a-27)
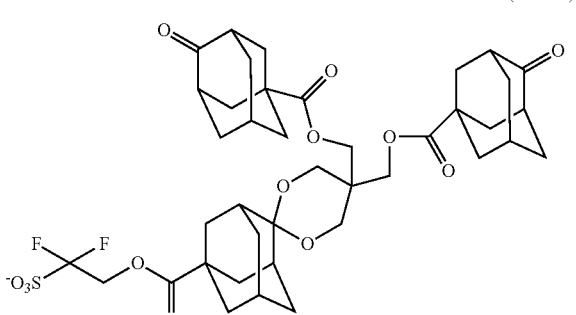
(B1a-31)
(B1a-32)
(B1a-33)
(B1a-34)
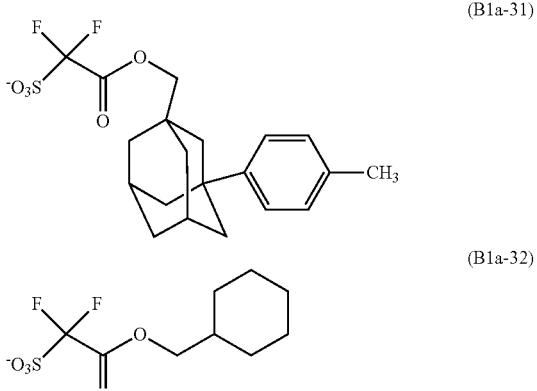
(B1a-28)
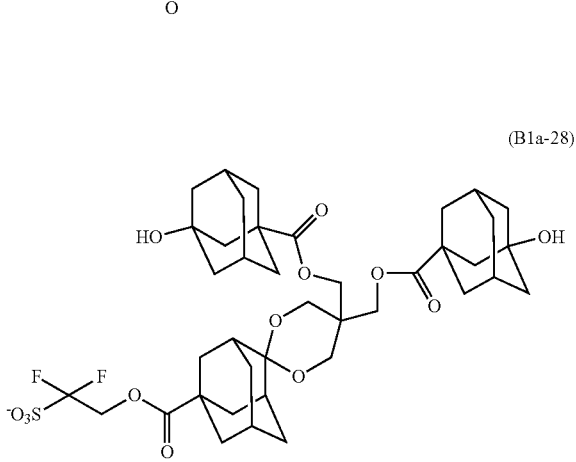
Among them, preferred are those represented by formulae (B1a-1) to (B1a-3), (B1a-7) to (B1a-16), (B1a-18), (B1a-19) and (B1a-22) to (B1a-34).

Examples of the organic cation represented by $Z^+$ include an organic onium cation such as an organic sulfonium cation, an organic iodonium cation, an organic ammonium cation, a benzothiazolium cation and an organic phosphonium cation.

Among them, an organic sulfonium cation and an organic iodonium cation are preferred, and a sulfonium cation, specifically arylsulfonium cation, is more preferred.

Preferred examples of the cation include those represented by the formulae (b2-1), (b2-2), (b2-3) and (b2-4):

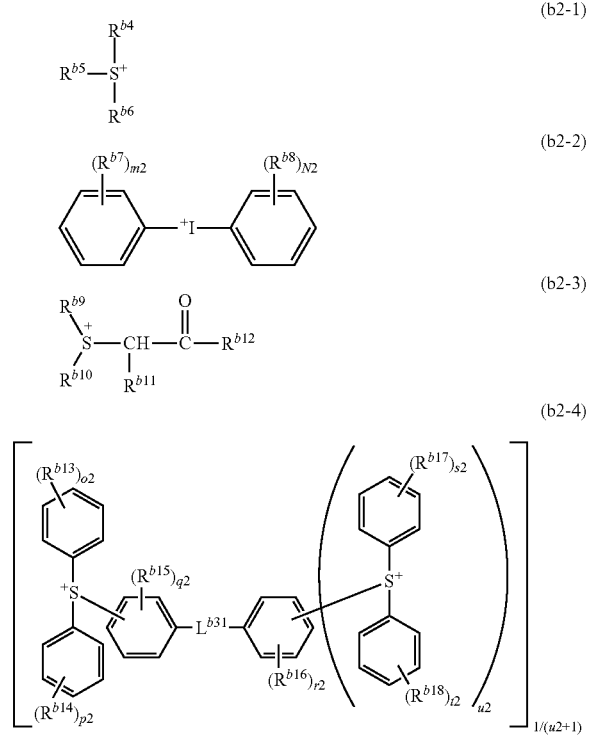

In the formulae (b2-1) to (b2-4), $R^{b4}$, $R^{b5}$ and $R^{b6}$ independently represent a C1-C30 aliphatic hydrocarbon group, a C3-C36 alicyclic hydrocarbon group and a C6-C36 aromatic hydrocarbon group. The aliphatic hydrocarbon group can have a substituent selected from the group consisting of a hydroxy group, a C1-C12 alkoxy group, a C3-C12 alicyclic hydrocarbon group and a C6-C18 aromatic hydrocarbon group. The alicyclic hydrocarbon group can have a substituent selected from the group consisting of a halogen atom, a C1-C18 aliphatic hydrocarbon group, a C2-C4 acyl group and a glycidyloxy group. The aromatic hydrocarbon group can have a substituent selected from the group consisting of a halogen atom, a hydroxy group, a C1-C18 aliphatic hydrocarbon group and a C1-C12 alkoxy group.

$R^{b4}$ and $R^{b5}$ can be bonded to form a ring together with the adjacent S+, and a methylene group in the ring may be replaced by —CO—, —O— or —SO—.

$R^{b7}$ and $R^{b8}$ are independently in each occurrence a hydroxy group, a C1-C12 aliphatic hydrocarbon group or a C1-C12 alkoxy group, m2 and n2 independently represents an integer of 0 to 5.

$R^{b9}$ and $R^{b10}$ independently represent a C1-C36 aliphatic hydrocarbon group or a C3-C36 alicyclic hydrocarbon group.

$R^{b9}$ and $R^{b10}$ can be bonded to form a ring together with the adjacent S+, and a methylene group in the divalent alicyclic hydrocarbon group may be replaced by —CO—, —O— or —SO—.

$R^{b11}$ represents a hydrogen atom, a C1-C36 aliphatic hydrocarbon group, a C3-C36 alicyclic hydrocarbon group or a C6-C18 aromatic hydrocarbon group.

$R^{b12}$ represents a C1-C12 aliphatic hydrocarbon group in which a hydrogen atom can be replaced by a C6-C18 aromatic hydrocarbon group, a C3-C18 saturated cyclic hydrocarbon group and a C6-C18 aromatic hydrocarbon group in which a hydrogen atom can be replaced by a C1-C12 alkoxy group or a (C1-C12 alkyl)carbonyloxy group.

$R^{b11}$ and $R^{b12}$ can be bonded each other to form a C1-C10 divalent alicyclic hydrocarbon group which forms a 2-oxocycloalkyl group together with the adjacent —CHCO—, and a methylene group in the divalent alicyclic hydrocarbon group may be replaced by —CO—, —O— or —SO—.

$R^{b13}$, $R^{b14}$, $R^{b15}$, $R^{b16}$, $R^{b17}$ and $R^{b18}$ independently represent a hydroxy group, a C1-C12 aliphatic hydrocarbon group or a C1-C12 alkoxy group.

$L^{b31}$ represents —S— or —O— and o2, p2, s2 and t2 each independently represents an integer of 0 to 5, q2 and r2 each independently represents an integer of 0 to 4, and u2 represents 0 or 1.

Preferred examples of the aliphatic hydrocarbon group represented by $R^{b4}$ to $R^{b12}$ include an alkyl group such as a methyl group, an ethyl group, a n-propyl group, an isopropyl group, a n-butyl group, sec-butyl group, a tert-butyl group, a pentyl group, a hexyl group, an octyl group and 2-ethylhexyl group. The aliphatic hydrocarbon group represented by $R^{b9}$, $R^{b10}$, $R^{b11}$ and $R^{b12}$ has preferably 1 to 12 carbon atoms.

The alicyclic hydrocarbon group may be a monocyclic or a polycyclic one. Preferred examples of the monocyclic hydrocarbon group include a cycloalkyl group such as a cyclopentyl group, a cyclohexyl group, a methylcyclohexyl group, a dimethylcyclohexyl group, a cycloheptyl group and a cyclooctyl group. Preferred examples of the polycyclic hydrocarbon group include an adamantyl group, a norbornyl group and a decahydronaphtyl group, and the following groups.

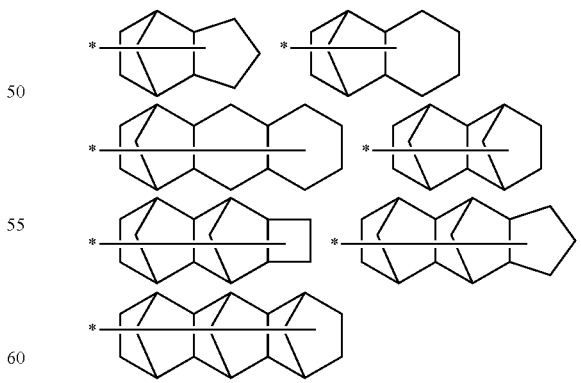

The alicyclic hydrocarbon group represented by $R^{b9}$, $R^{b10}$, $R^{b11}$ and $R^{b12}$ has preferably 3 to 18 carbon atoms, more preferably 4 to 12 carbon atoms.

Examples of the alicyclic hydrocarbon group in which a hydrogen atom has been replaced by an aliphatic hydrocarbon group include a methylcyclohexyl group, a dimethylcyclohexyl group, a methylnorbornyl group, and an isonorbornyl group.

The alicyclic hydrocarbon group in which a hydrogen atom has been replaced by an aliphatic hydrocarbon group has preferably 20 or less carbon atoms in total.

Examples of the aromatic hydrocarbon group include an aryl group such as a phenyl group, tolyl group, xylyl group, cumenyl group, mesityl group, p-ethylphenyl group, p-tert-butylphenyl group, p-adamantylphenyl group, a biphenylyl group, a naphthyl group, a phenanthryl group, a 2,6-diethylphenyl group, a 2-methyl-6-ethylphenyl group.

When the aromatic hydrocarbon group has an alicyclic hydrocarbon group or an aliphatic hydrocarbon group, it is preferred that the alicyclic hydrocarbon group and the aliphatic hydrocarbon group have respectively 1 to 18 carbon atoms and 3 to 18 carbon atoms. Examples of the aromatic hydrocarbon group in which a hydrogen atom has been replaced by an alkoxy group include the p-methoxyphenyl group.

Examples of the aliphatic hydrocarbon group in which a hydrogen atom has been replaced by an aromatic hydrocarbon group include a benzyl group, a phenethyl group, a phenylpropyl group, trityl group, naphthylmethyl group, and a naphthylethyl group.

Examples of the alkoxy group include a methoxy group, an ethoxy group, a propoxy group, a butoxy group, a pentyloxy group, a hexyloxy group, a heptyloxy group, an octyloxy group, a decyloxy group and a dodecyloxy group.

Examples of the acyl group include an acetyl group, a propionyl group and a butyryl group.

Examples of the halogen atom include a fluorine atom, a chlorine atom, a bromine atom and an iodine atom.

Examples of alkylcarbonyloxy group include a methylcarbonyloxy group, an ethylcarbonyloxy group, a n-propylcarbonyloxy group, an isopropylcarbonyloxy group, a n-butylcarbonyloxy group, a sec-butylcarbonyloxy group, a tert-butylcarbonyloxy group, a pentylcarbonyloxy group, a hexylcarbonyloxy group, an octylcarbonyloxy group and a 2-ethyl hexylcarbonyloxy group.

The ring group formed by bonding $R^{b4}$ and $R^{b5}$ together with the adjacent $S^+$ may be a monocyclic or polycyclic, a saturated or unsaturated, an aromatic or nonaromatic group. The ring is generally 3 to 12-membered one, preferably 3 to 7-membered one. Examples of the ring include the following ones.

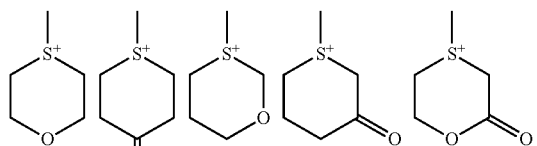
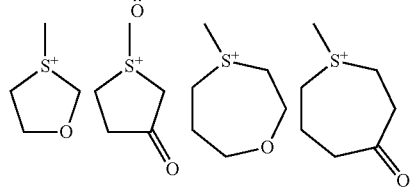

The ring group formed by bonding $R^{b9}$ and $R^{b10}$ together with the adjacent $S^+$ may be monocyclic or polycyclic, saturated or unsaturated, aromatic or nonaromatic group. The ring has generally C3-C12, preferably C3-C7 carbon atoms. Examples of the ring include a thiolan-1-ium ring (tetrahydrothiphenium ring), a thian-1-ium ring and a 1,4-oxathian-4-ium ring.

The ring group formed by bonding $R^{b11}$ and $R^{b12}$ together with —CH—CO— may be monocyclic or polycyclic, saturated or unsaturated, aromatic or nonaromatic group. The ring has generally C3-C12, preferably C3-C7 carbon atoms. Examples of the ring include an oxocycloheptane ring, an oxocyclohexane ring, an oxonorbornane ring, and an oxoadamantane ring.

Preferred examples of the cation for the acid generator include an arylsulfonium cation, specifically cation of formula (b2-1), and more specifically a phenylsulfonium cation.

Preferably, the cation of formula (b2-1) has one or three phenyl groups. When the cation of formula (b2-1) has one phenyl group, it has further a thiolan-1-ium ring or a 1,4-oxathian-4-ium ring.

Examples of the cation represented by the formula (b2-1) include the following.

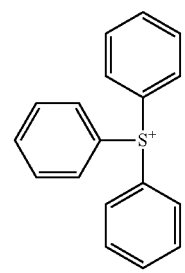
(b2-c-1)

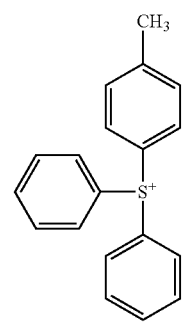
(b2-c-2)

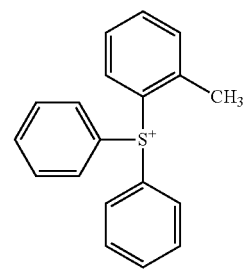
(b2-c-3)

-continued
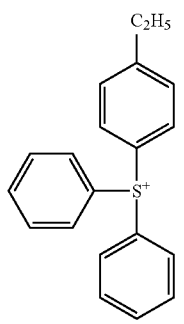 (b2-c-4)
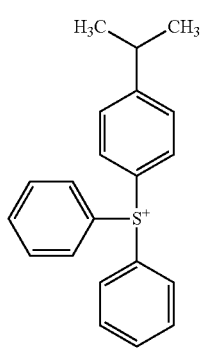 (b2-c-5)
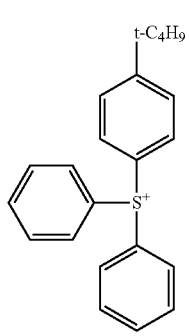 (b2-c-6)
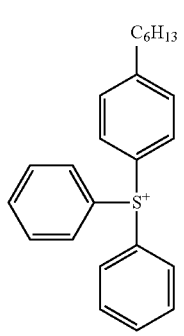 (b2-c-7)
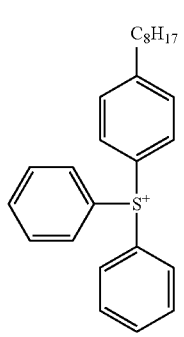 (b2-c-8)
-continued
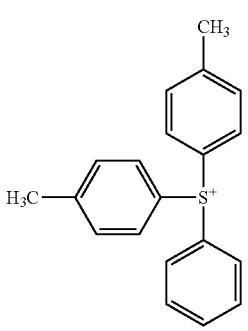 (b2-c-9)
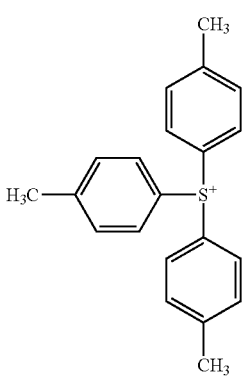 (b2-c-10)
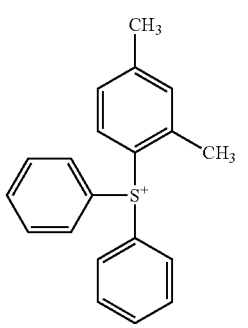 (b2-c-11)
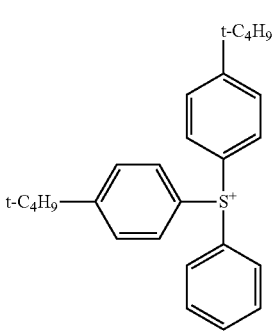 (b2-c-12)

(b2-c-13)
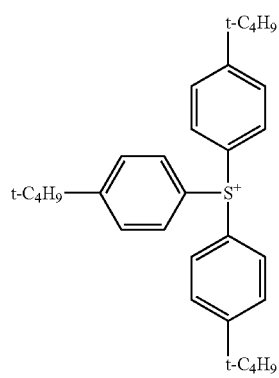
(b2-c-14)
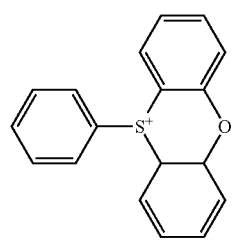
(b2-c-15)
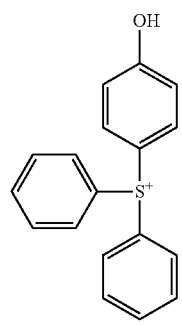
(b2-c-16)
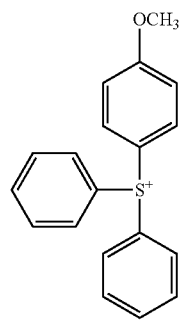
(b2-c-17)
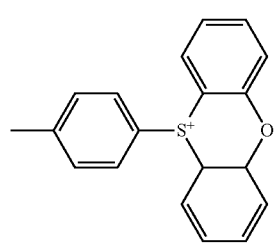
(b2-c-18)
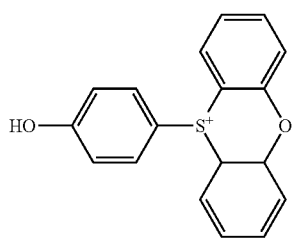
(b2-c-19)
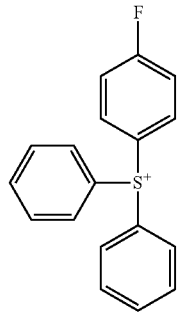
(b2-c-20)
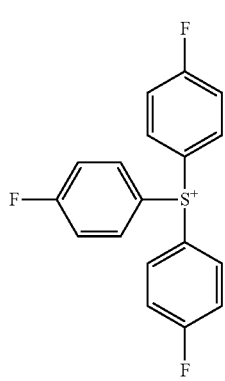
(b2-c-21)
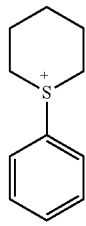
(b2-c-22)
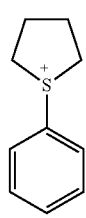
(b2-c-23)
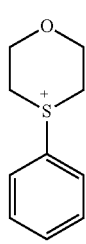

(b2-c-24) 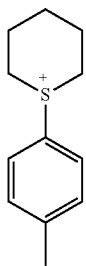
(b2-c-25) 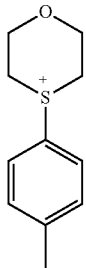
(b2-c-26) 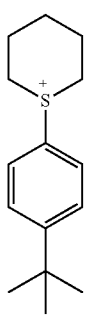
(b2-c-27) 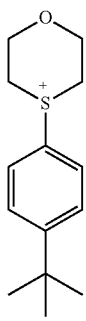
Examples of the cation represented by the formula (b2-2) include the followings.
(b2-c-28) 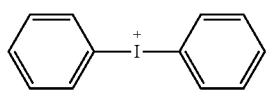
(b2-c-29) 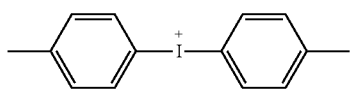
(b2-c-30) 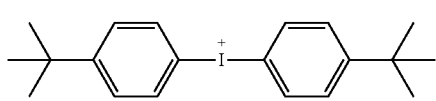
Examples of the cation represented by the formula (b2-3) include the followings.
(b2-c-31) 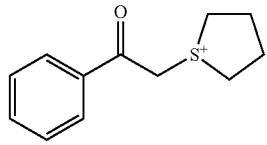
(b2-c-32) 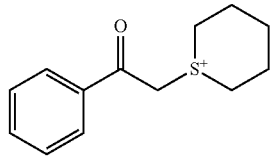
(b2-c-33) 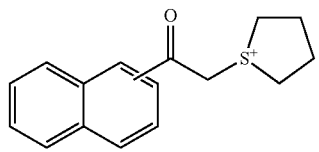
(b2-c-34) 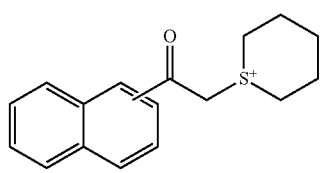
Examples of the cation represented by the formula (b2-4) include the followings.
(b2-c-35) 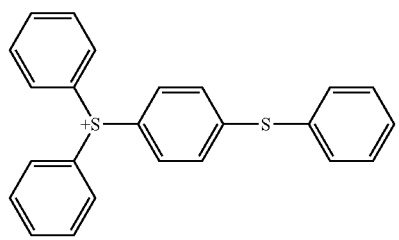
(b2-c-36) 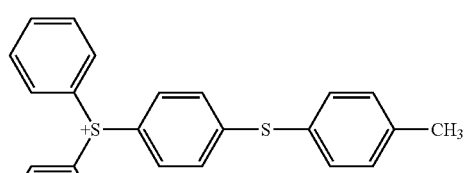
(b2-c-37) 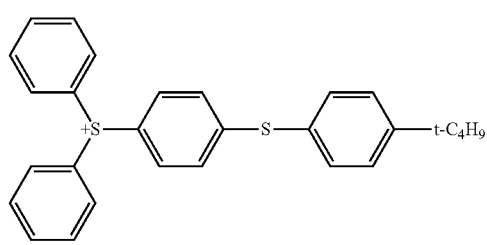

(b2-c-38)
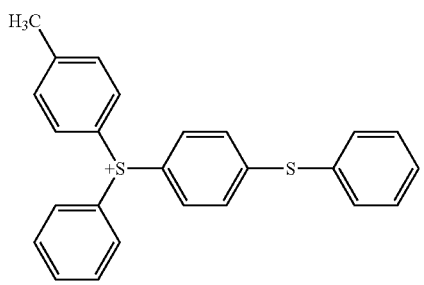

(b2-c-39)
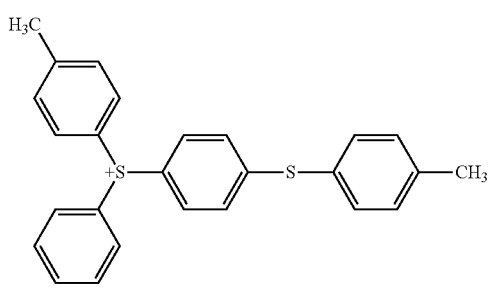

(b2-c-40)
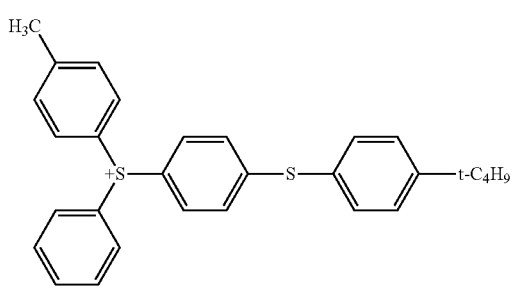

(b2-c-41)
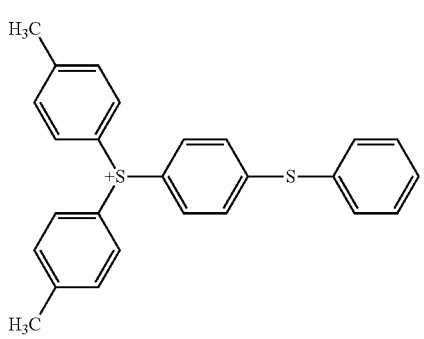

(b2-c-42)
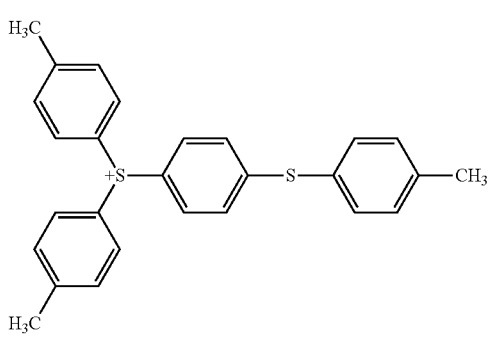

(b2-c-43)
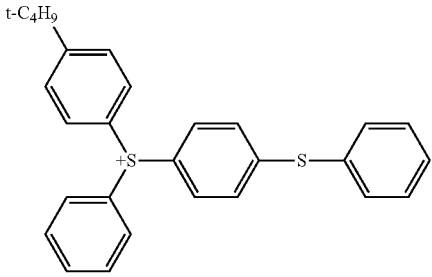

(b2-c-44)
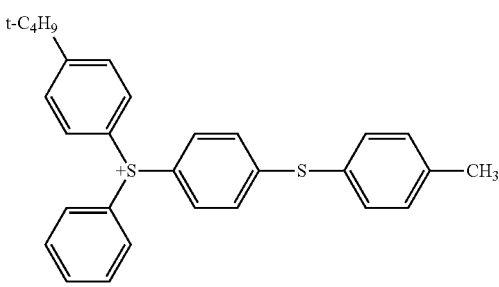

(b2-c-45)
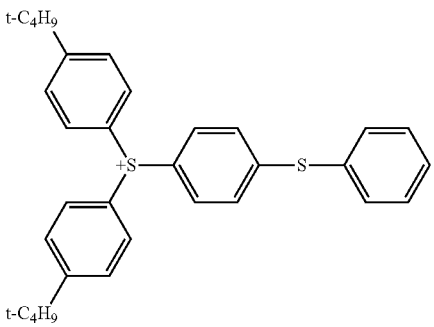

(b2-c-46)
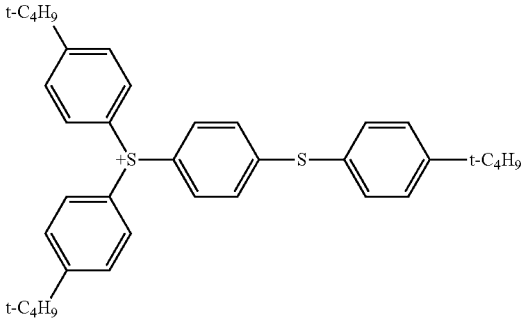

Examples of the organic counter ion represented by $Z^+$ include an onium cation such as a sulfonium cation, an iodonium cation, an ammonium cation, a benzothiazolium cation and a phosphonium cation, and a sulfonium cation and an iodonium cation are preferred, and a sulfonium cation, specifically an arylsulfonium cation, is more preferred.

Specific examples of the salt represented by formula (B1) include the following salts represented by formulae (B1-1) to (B1-48). Among them, those which comprise an arylsulfonium cation are preferred, the salts represented by formulae (B1-1) to (B1-3), (B1-5) to (B1-7), (B1-11) to (B1-14), (B1-17), (B1-20) to (B1-26), (B1-29), (B1-31) to (B1-48) are more preferred.

(B1-1)
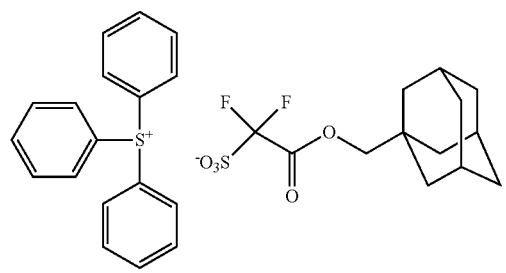
(B1-2)
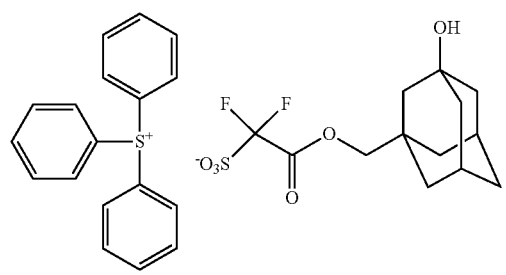
(B1-3)
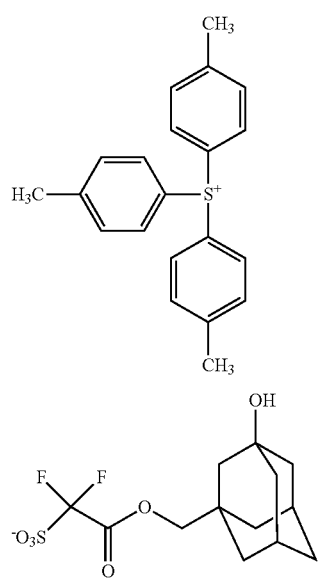
(B1-4)
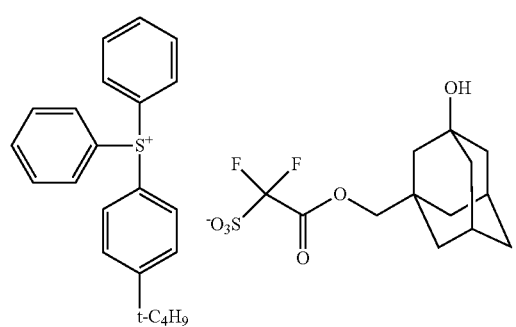
-continued
(B1-5)
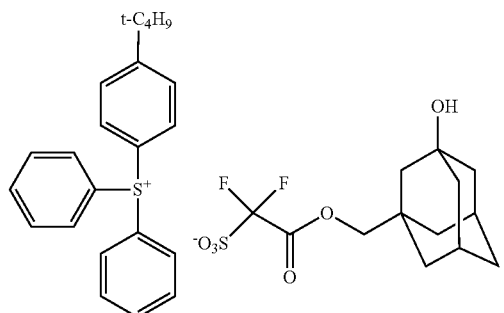
(B1-6)
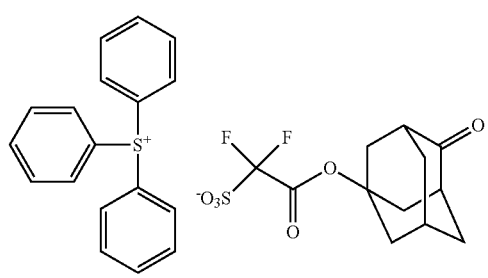
(B1-7)
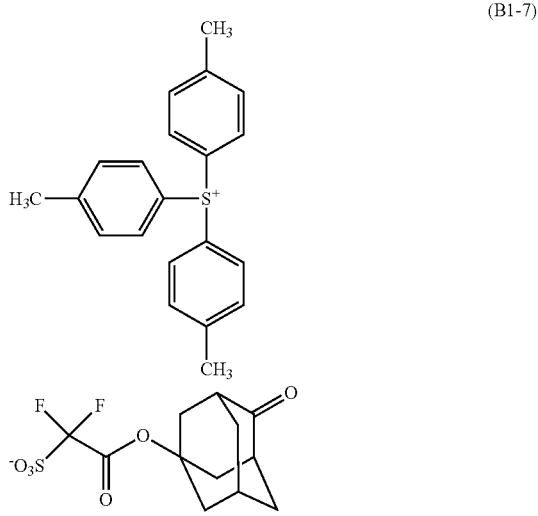
(B1-8)
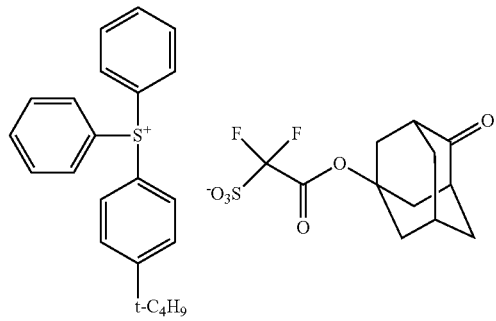

(B1-9)
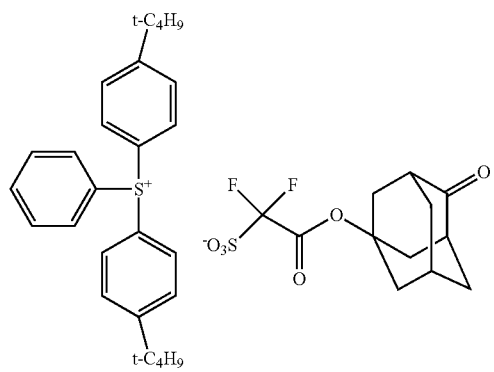
(B1-10)
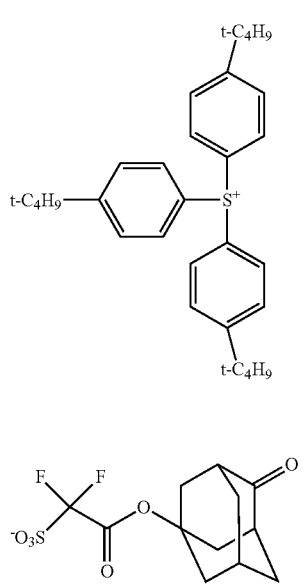
(B1-11)
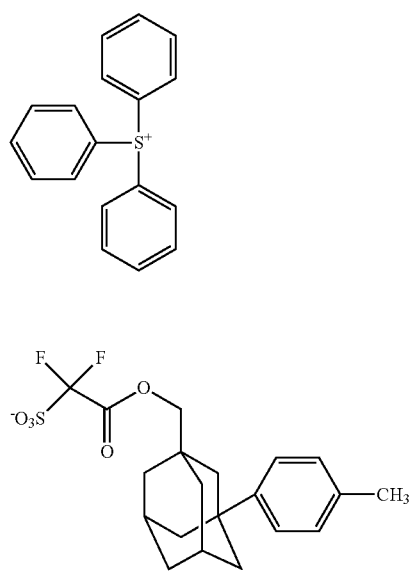
(B1-12)
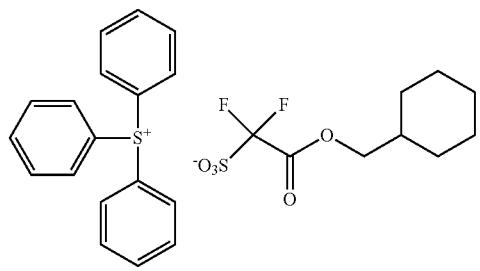
(B1-13)
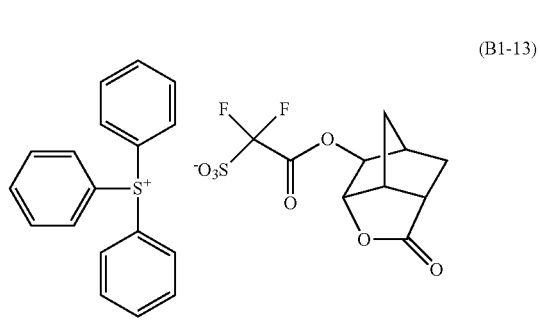
(B1-14)
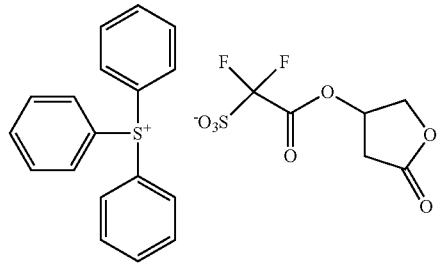
(B1-15)
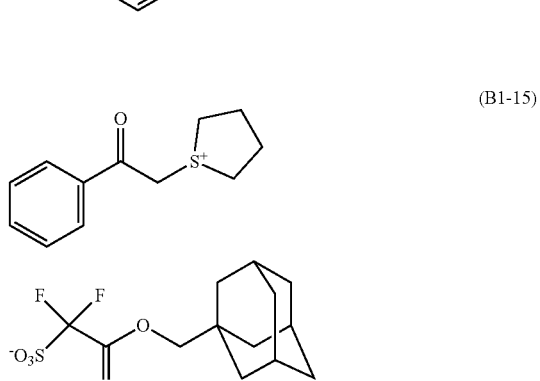
(B1-16)
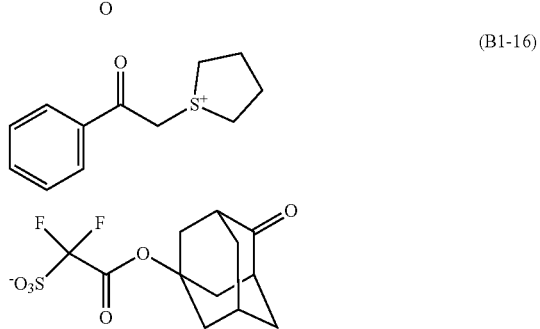

(B1-17) 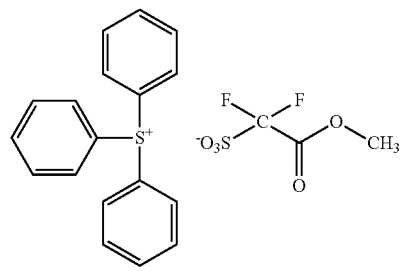
(B1-18) 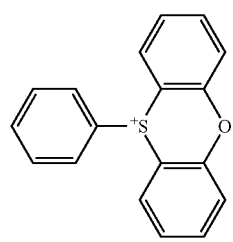
(B1-19) 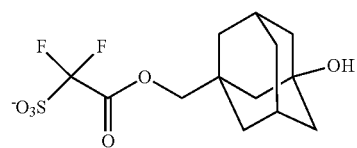
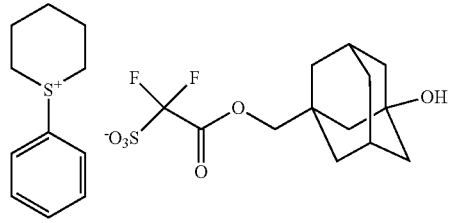
(B1-20) 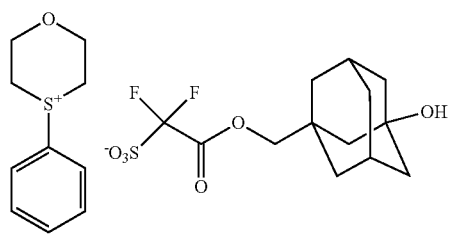
(B1-21) 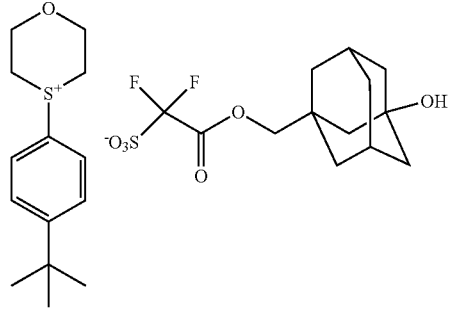
(B1-22) 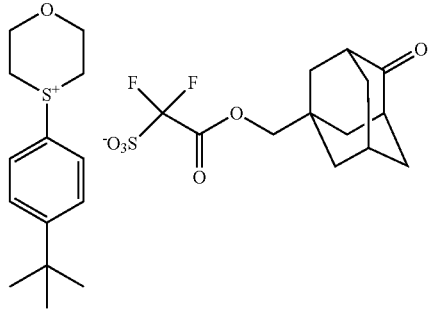
(B1-23) 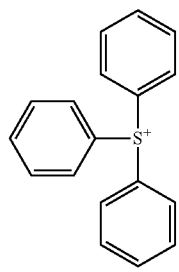
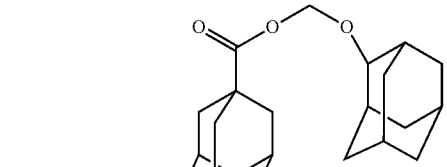
(B1-24) 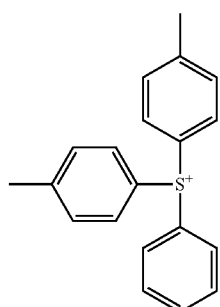
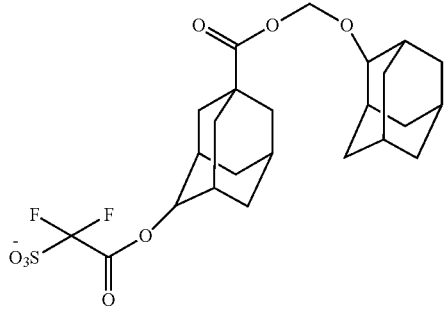

(B1-25)
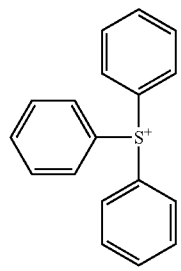
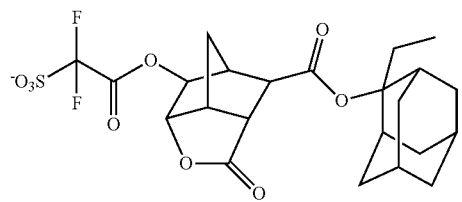
(B1-26)
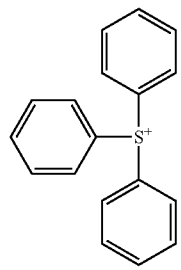
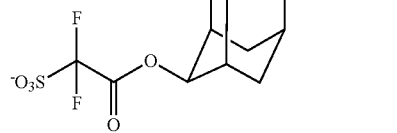
(B1-27)
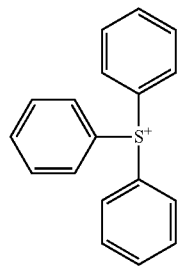
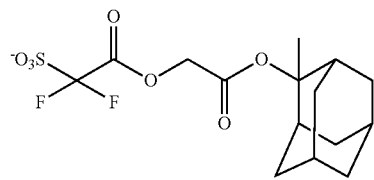
(B1-28)
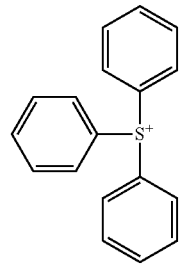
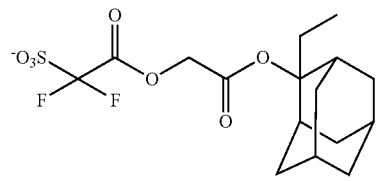
(B1-29)
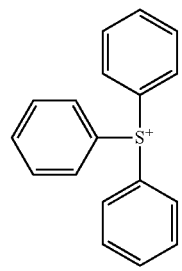
(B1-30)
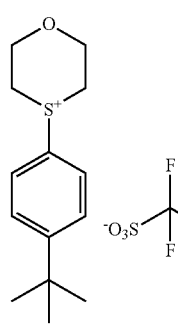
(B1-31)
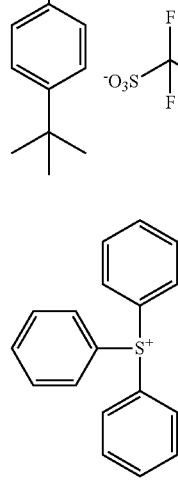
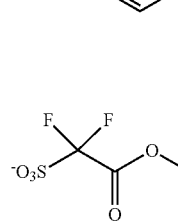

(B1-32)
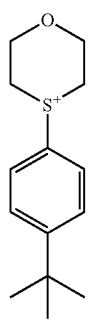
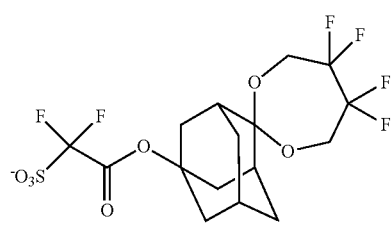
(B1-33)
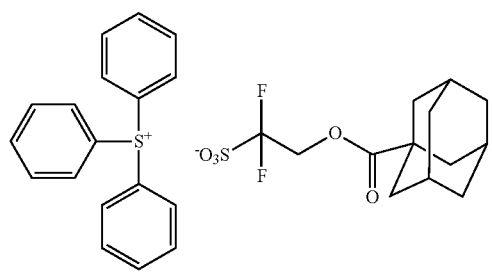
(B1-34)
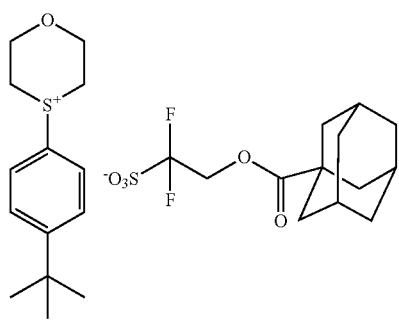
(B1-35)
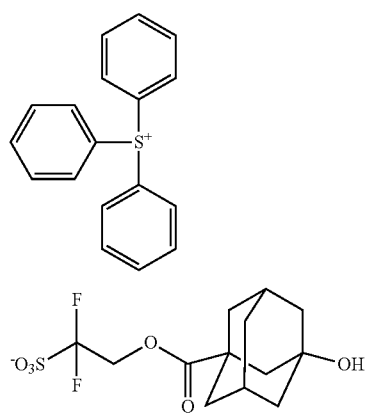
(B1-36)
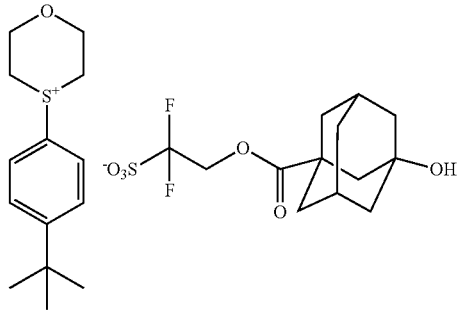
(B1-37)
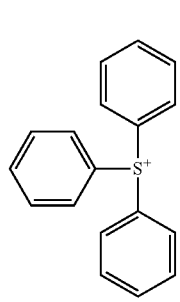
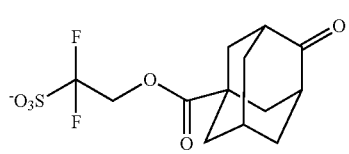
(B1-38)
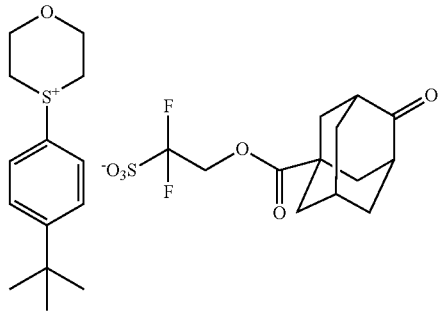
(B1-39)
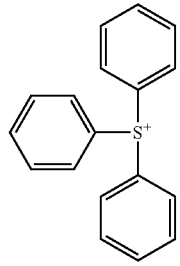
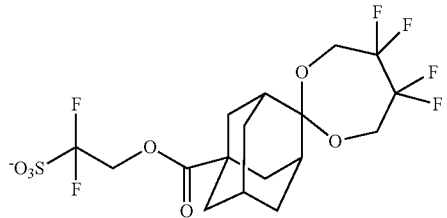

(B1-40)
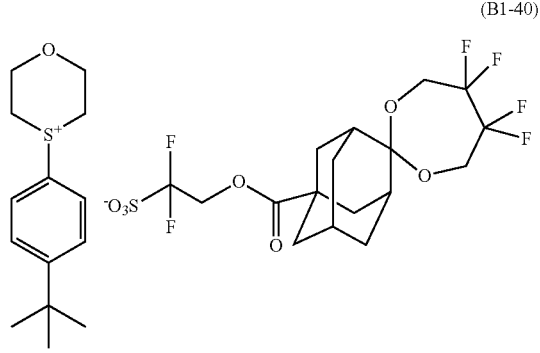
(B1-41)
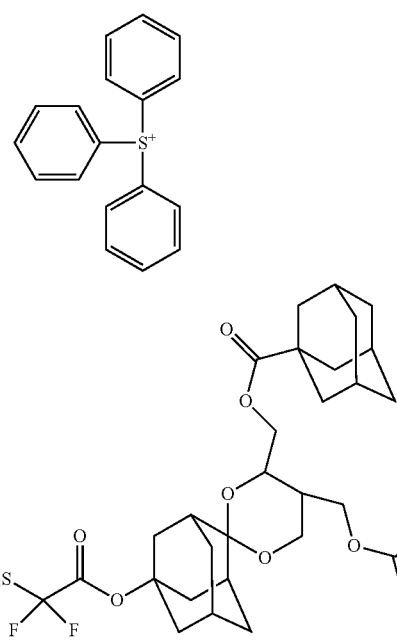
(B1-42)
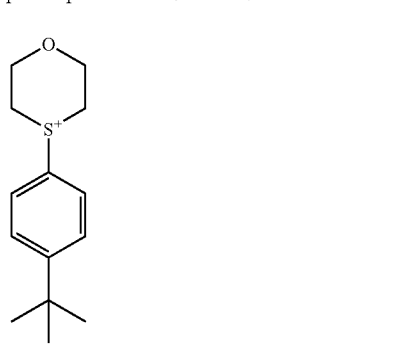
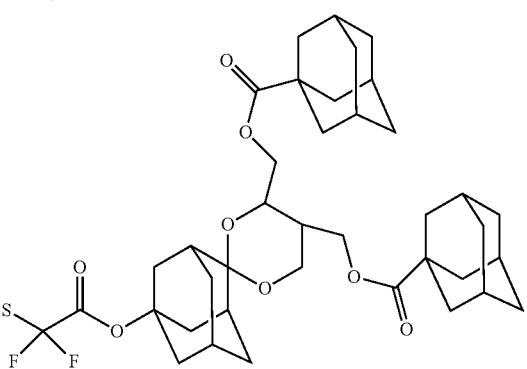
(B1-43)
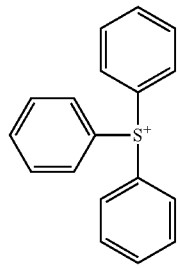
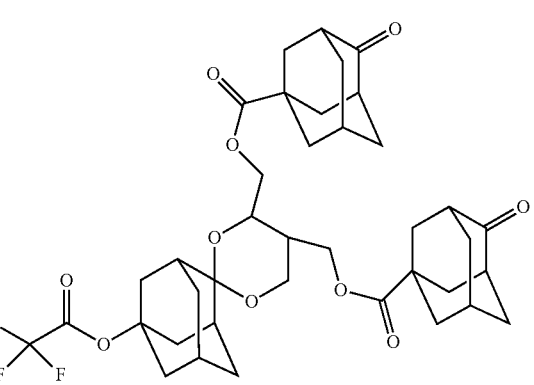
(B1-44)
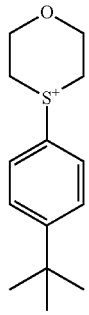
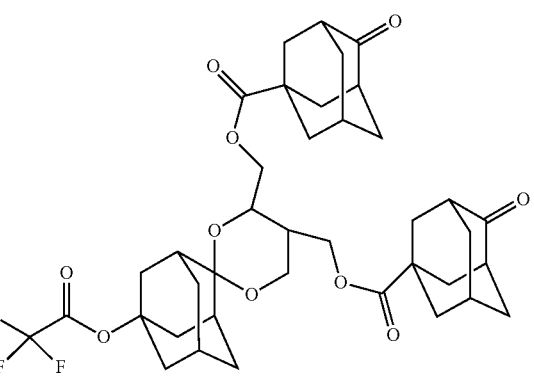
(B1-45)
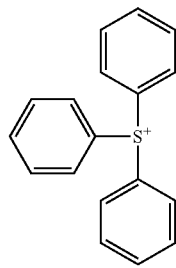

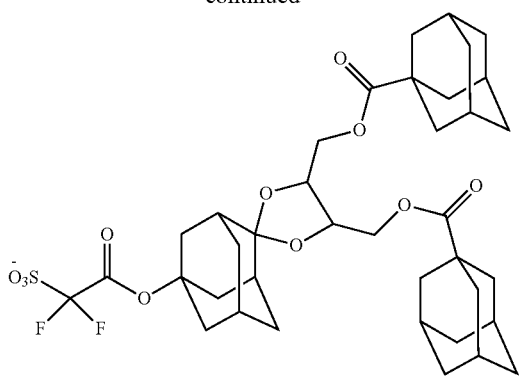

(B1-46)

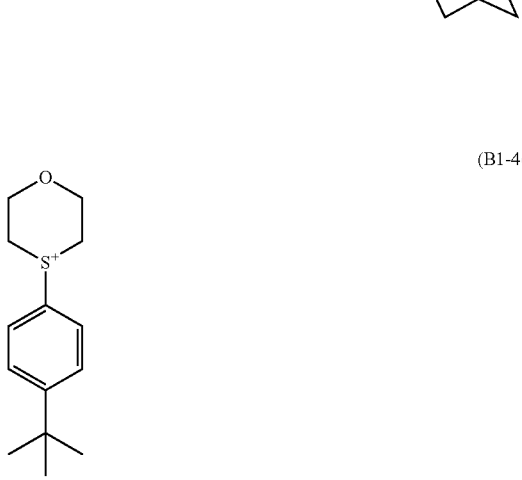

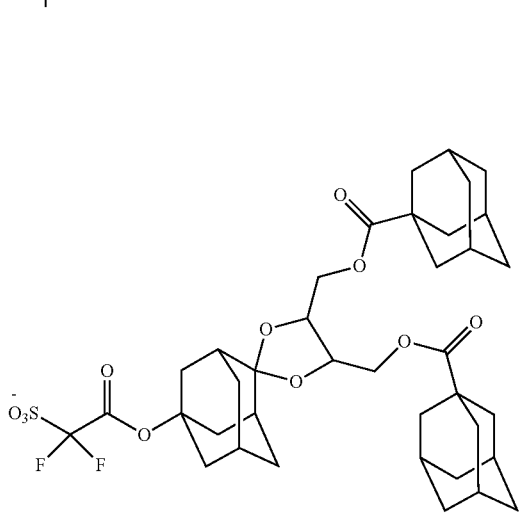

(B1-47)

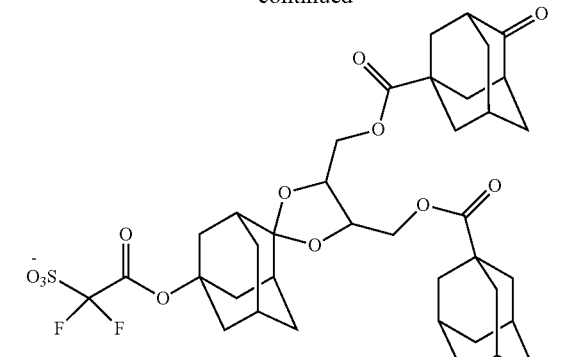

(B1-48)

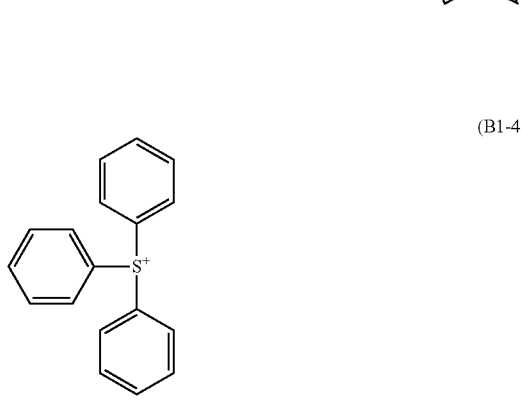

The composition of the present disclosure may contain two or more kinds of the acid generator (B).

The total content of the acid generator (B) is preferably 1 to 40 parts by mass, more preferably 3 to 35 parts by mass, per 100 parts of Resin (A)

<Salt which Generates an Acid Having Acidity Weaker than an Acid Generated from an Acid Generator>

The composition of the present disclosure can further comprise a salt which generates an acid having acidity weaker than an acid generated from an acid generator. This acid generally acts as a quencher, which has the property that it can trap an acid, especially an acid generated from an acid generator by exposure to light for lithography.

As to a salt which generates an acid having acidity weaker than an acid generated from an acid generator, the acidity in the salts is shown by the acid dissociation constant (pKa).

The acid dissociation constant of acid generated from the salt for a quencher is usually a salt of $-3<\mathrm{pKa}$.

The salt for a quencher is preferably a salt of $-1<\mathrm{pKa}<7$, and more preferably a salt of $0<\mathrm{pKa}<5$.

Specific examples of the salt for a quencher include the following ones, an onium carboxylic acid salt such as the salt of formula (D), and salts recited in US2012/328986A1, US2011/171576A1, US2011/201823A1, JP2011-39502A1, and US2011/200935A1.
The photoresist composition comprises preferably onium carboxylic acid salt, more preferably the salt of formula (D).
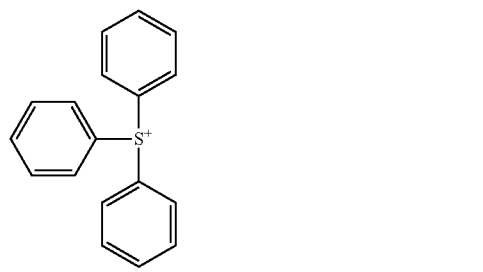
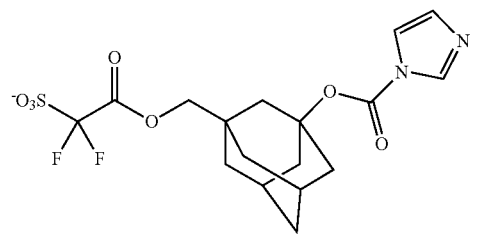
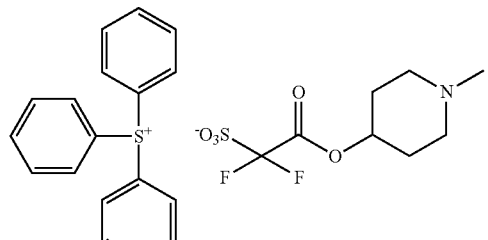
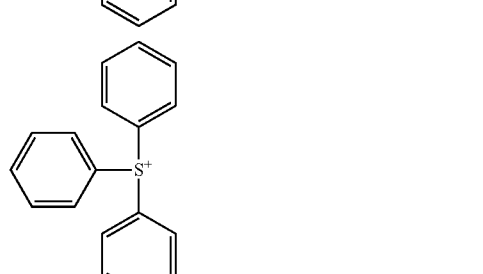
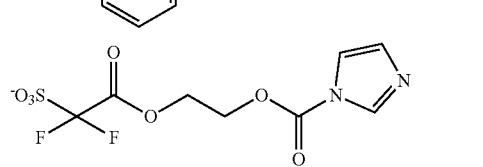
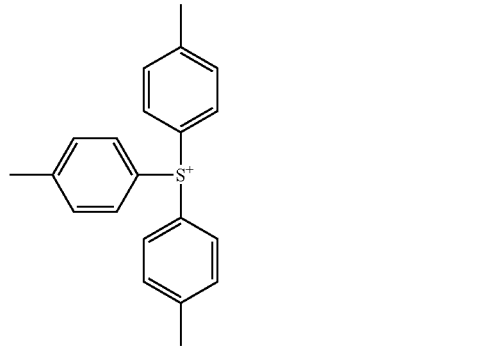
-continued
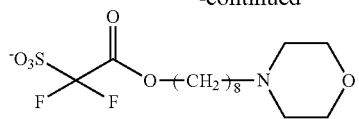
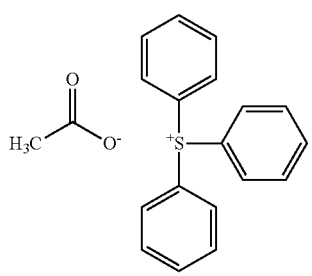
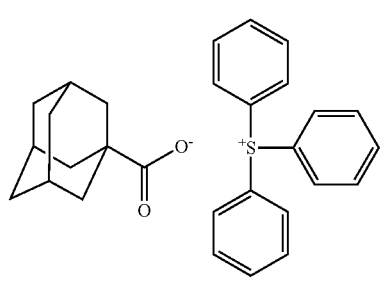
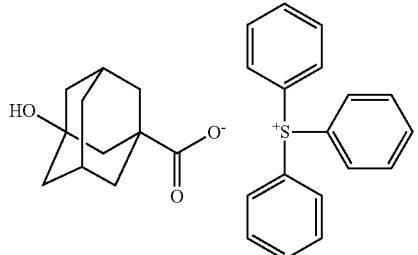
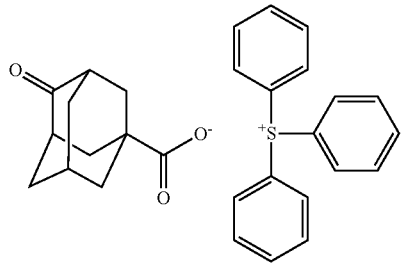
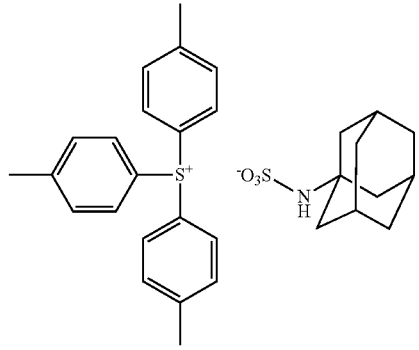

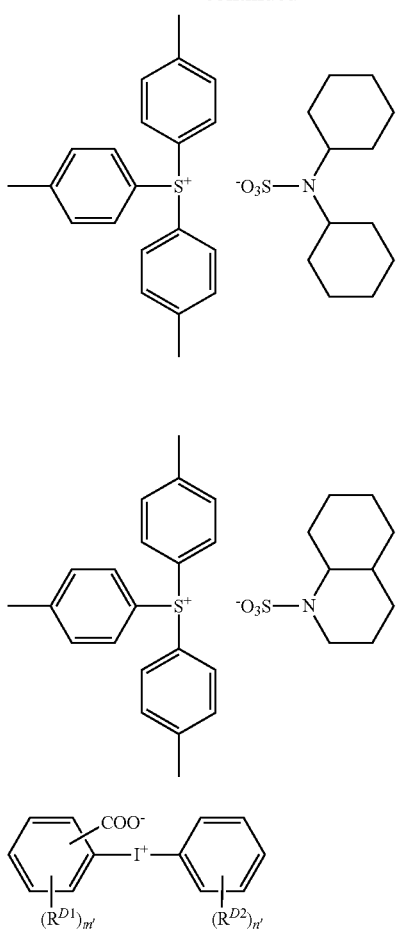

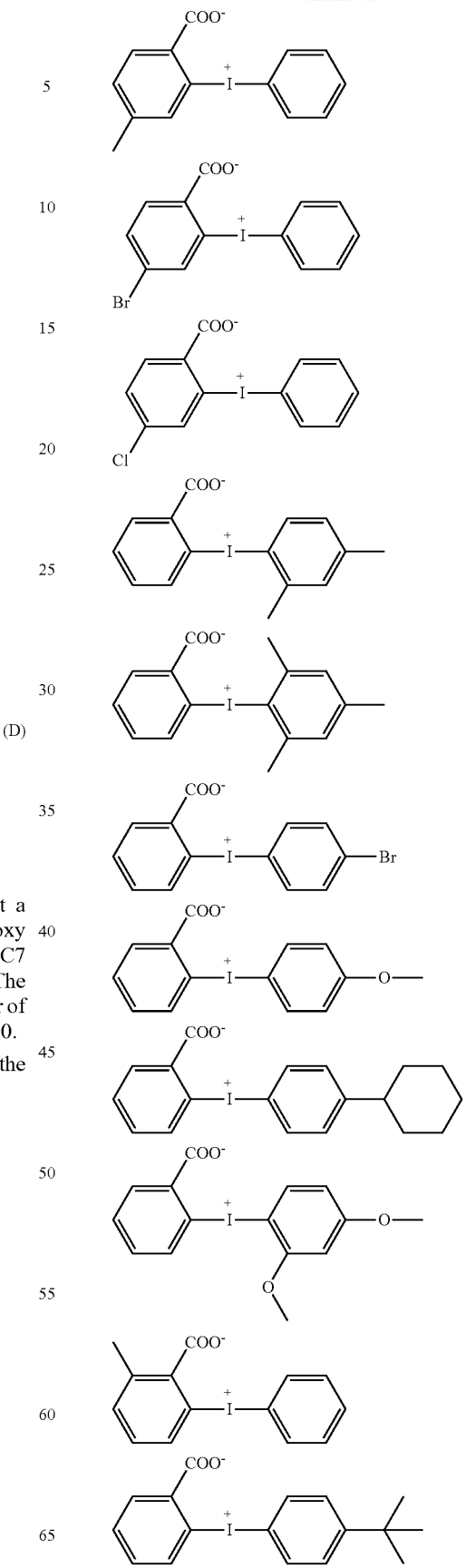

(D)

In formula (D), $R^{D1}$ and $R^{D2}$ respectively represent a C1-C12 monovalent hydrocarbon group, a C1-C6 alkoxy group, a C2-C7 acyl group, a C2-C7 acyloxy group, a C2-C7 alkoxycarbonyl group, a nitro group or a halogen atom. The symbols m' and n' each independently represent an integer of 0 to 4, preferably an integer of 0 to 2, more preferably 0.

Examples of the compounds of formula (D) include the following ones.

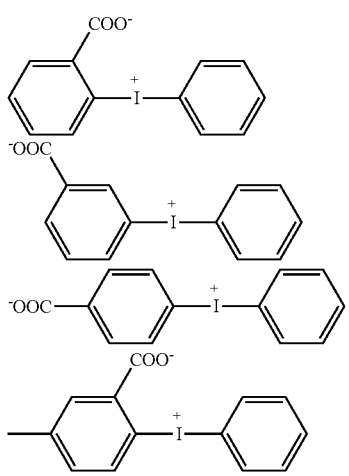

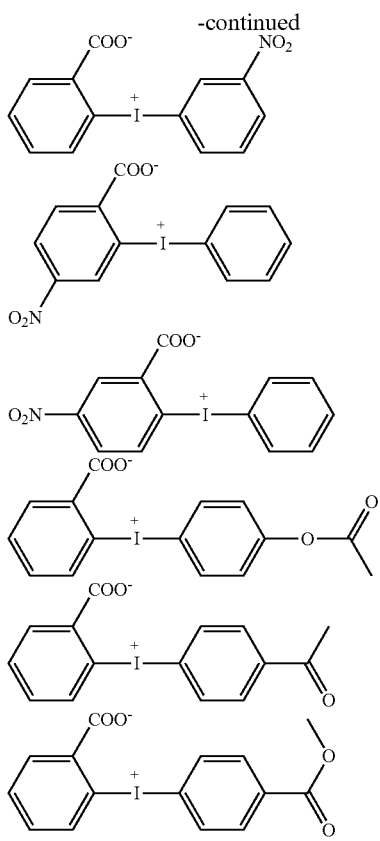

<Basic Compound>

The photoresist composition of the disclosure may further contain a basic compound. The basic compound generally has the property that it can trap an acid, especially an acid generated from an acid generator by exposure to light for lithography, and generally acts as a quencher.

Examples of the basic compound include a basic nitrogen-containing organic compound.

Examples of the basic nitrogen-containing organic compound include an amine compound such as an aliphatic amine, an aromatic amine and an ammonium salt. Examples of the aliphatic amine include a primary amine, a secondary amine and a tertiary amine.

Examples of the basic compound include 1-naphthylamine, 2-naphthylamine, aniline, diisopropylaniline, 2-, 3- or 4-methylaniline, 4-nitroaniline, N-methylaniline, N,N-dimethylaniline, diphenylamine, hexylamine, heptylamine, octylamine, nonylamine, decylamine, dibutylamine, pentylamine, dioctylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethyldipentylamine, ethyldihexylamine, ethyldiheptylamine, ethyldioctylamine, ethyldinonylamine, ethyldidecylamine, dicyclohexylmethylamine, tris [2-(2-methoxyethoxy)ethyl]amine, triisopropanolamine, ethylenediamine, tetramethylenediamine, hexamethylenediamine, 4,4'-diamino-1,2-diphenylethane, 4,4'-diamino-3,3'-dimethyldiphenylmethane, 4,4'-diamino-3,3'-diethyldiphenylmethane, piperazine, morpholine, piperidine, hindered amine compound having a piperidine structure, 2,2'-methylenebisaniline, imidazole, 4-methylimidazole, pyridine, 4-methylpyridine, 1,2-di(2-pyridyl)ethane, 1,2-di(4-pyridyl)ethane, 1,2-di(2-pyridyl) ethene, 1,2-di(4-pyridyl)ethene, 1,3-di(4-pyridyl) propane, 1,2-di(4-pyridyloxy) ethane, di(2-pyridyl) ketone, 4,4'-dipyridyl sulfide, 4,4'-dipyridyl disulfide, 2,2'-dipyridylamine, 2,2'-dipicolylamine and bipyridine.

Examples of the quaternary ammonium hydroxide include tetramethylammonium hydroxide, tetrabutylammonium hydroxide, tetrahexylammonium hydroxide, tetraoctylammonium hydroxide, phenyltrimethylammonium hydroxide, (3-trifluoromethylphenyl)trimethylammonium hydroxide and (2-hydroxyethyl)trimethylammonium hydroxide (so-called "choline").

The content of the quencher including the above-mentioned salt and a basic compound is preferably 0.01 to 5% by mass, and more preferably 0.01 to 3% by mass, based on the sum of the solid components.

<Solvent>

Preferably, the photoresist composition of the disclosure further contains a solvent.

The amount of the solvent is usually 90% by weight or more, preferably 92% by weight or more preferably 94% by weight or more based on the total amount of the photoresist composition of the present invention. The amount of the solvent is usually 99.9% by weight or less and preferably 99% by weight or less based on the total amount of the photoresist composition of the present invention.

The content can be measured with known methods such as liquid chromatography or gas chromatography.

Examples of the solvent include a glycol ether ester such as ethyl cellosolve acetate, methyl cellosolve acetate and propylene glycol monomethyl ether acetate; a glycol ether such as propylene glycol monomethyl ether; an ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone.

<Additives>

The photoresist compositions of the present invention may comprise, if necessary, a small amount of various additives such as a sensitizer, a dissolution inhibitor, other polymers, a surfactant, a stabilizer and a dye as long as the effect of the present invention is not prevented.

The photoresist compositions of the present invention can be prepared by mixing, usually in a solvent, Resin (A) and an acid generator (B), and if necessary Resin (A2), Resin (X), a quencher, and/or additives at a suitable ratio for the composition, optionally followed by filtrating the mixture with a filter having 0.003 m to 0.2 m of a pore size.

The order of mixing these components is not limited to any specific order. The temperature at mixing the components is usually 10 to 40° C., which can be selected in view of the resin or the like. The mixing time is usually 0.5 to 24 hours, which can be selected in view of the temperature. The means for mixing the components is not limited to specific one. The components can be mixed by being stirred.

The amounts of the components in the photoresist compositions can be adjusted by selecting the amount to be used for production of them.

The photoresist compositions of the disclosure are useful for a chemically amplified photoresist composition.

A photoresist pattern can be produced by the following steps (1) to (5):

(1) a step of applying the photoresist composition of the present invention on a substrate, (2) a step of forming a composition film by conducting drying, (3) a step of exposing the composition film to radiation,
(4) a step of baking the exposed composition film, and
(5) a step of developing the baked composition film.

The applying of the photoresist composition on a substrate is usually conducted using a conventional apparatus such as spin coater. Examples of the substrate include a silicon wafer or a quartz wafer on which a sensor, a circuit, a transistor or the like is formed.

The formation of the composition film is usually conducted using a heating apparatus such as hot plate or a decompressor, and the heating temperature is usually 50 to 200° C. When the pressure is reduced during heating, the operation pressure is usually 1 to $1.0 \times 10^5$ Pa. The heating time is usually 10 to 180 seconds.

The composition film obtained is exposed to radiation using an exposure system. The exposure is usually conducted through a mask having a pattern corresponding to the desired photoresist pattern. Examples of the exposure source include a light source radiating laser light in a UV-region such as a KrF excimer laser (wavelength: 248 nm), an ArF excimer laser (wavelength: 193 nm) and a $F_2$ laser (wavelength: 157 nm), a light source radiating harmonic laser light in a far UV region or a vacuum UV region by wavelength conversion of laser light from a solid laser light source (such as YAG or semiconductor laser), and a light source radiating electron beam or EUV (extreme ultraviolet) light.

The temperature of baking of the exposed composition film is usually 50 to 200° C., and preferably 70 to 150° C.

The development of the baked composition film is usually carried out using a development apparatus. The development method includes dipping methods, paddle methods, spray methods and dynamic dispense method. The developing temperature is preferably 5 to 60° C., and the developing time is preferably 5 to 300 seconds.

The positive and negative type photoresist patterns can be obtained by the development depending on a developer to be used therefor.

When a positive type photoresist pattern is prepared from the photoresist composition of the present invention, the development can be conducted with an alkaline developer. The alkaline developer to be used may be any one of various alkaline aqueous solution used in the art. Generally, an aqueous solution of tetramethylammonium hydroxide or (2-hydroxyethyl)trimethylammonium hydroxide (commonly known as "choline") is often used. The alkaline developer may comprise a surfactant.

After development, the photoresist film having photoresist pattern is preferably washed with ultrapure water, and the remained water on the photoresist film and the substrate is preferably removed therefrom.

When a negative type photoresist pattern is prepared from the photoresist composition of the present invention, the development can be conducted with a developer containing an organic solvent, such developer is sometimes referred to as "organic developer".

Examples of an organic solvent for organic developer include ketone solvents such as 2-hexanone, 2-heptanone; glycolether ester solvents such as propyleneglycolmonomethylether acetate; ester solvents such as butyl acetate; glycolether solvents such as propyleneglycolmonomethylether; amide solvents such as N,N-dimethylacetamide; and aromatic hydrocarbon solvents such as anisole.

The content of organic solvent is preferably from 90% to 100% by weight, more preferably from 95% to 100% by weight, in an organic developer. Preferred is that the organic developer essentially consists of an organic solvent.

Among them, the organic developer is preferably a developer comprising butyl acetate and/or 2-heptanone.

The total content of butyl acetate and 2-heptanone is preferably from 90% to 100% by weight, more preferably from 95% to 100% by weight. Preferred is that the organic developer essentially consists of butyl acetate and/or 2-heptanone.

The organic developer may comprise a surfactant or a very small amount of water.

Development with an organic developer can be stopped by replacing the developer by a rinse agent. The rinse agent is not limited to any specific one, as long as it does not dissolve a photoresist composition. Examples of the rinse agent include an organic solvent which contains, for example, an alcohol solvent or an ester solvent.

The photoresist composition of the present invention is suitable for KrF excimer laser lithography, ArF excimer laser lithography, EUV (extreme ultraviolet) lithography, EUV immersion lithography and EB (electron beam) lithography.

EXAMPLES

The present invention will be described more specifically by Examples, which are not construed to limit the scope of the present invention.

The "%" and "part(s)" used to represent the content of any component and the amount of any material used in the following examples and comparative examples are on a weight basis unless otherwise specifically noted.

The weight-average molecular weight of any material used in the following examples is a value found by gel permeation chromatography under the following conditions.

Column: HLC-8120GPC Type (Three Columns with guard column), TSKgel
Multipore HXL-M, manufactured by TOSOH CORPORATION
Solvent: Tetrahydrofuran, Flow rate: 1.0 mL/min.
Detector: RI detector
Column temperature: 40° C.
Injection volume: 100 μL
Standard reference material: Standard polystyrene
Structures of compounds were determined by mass spectrometry (Liquid Chromatography: 1100 Type, manufactured by AGILENT TECHNOLOGIES LTD., Mass Spectrometry: LC/MSD Type, manufactured by AGILENT TECHNOLOGIES LTD.).

In the following examples, the value of the molecular ion peak is referred to as "MASS".

Example 1

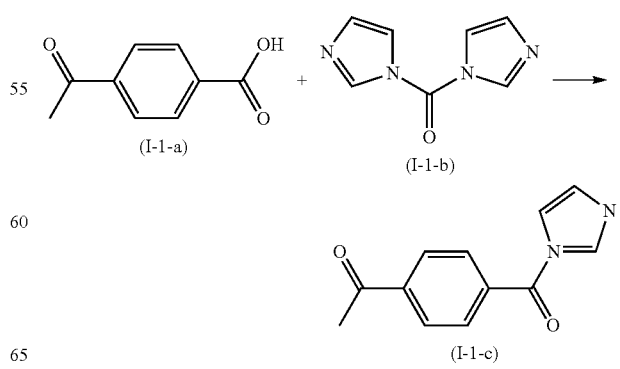

In a reactor, 9.11 parts of the compound represented by the formula (I-1-a) and 50 parts of acetonitrile were mixed and stirred at 40° C. for 30 minutes. To the obtained mixture, 10.79 parts of the compound represented by the formula (I-1-b) was added and then stirred at 23° C. for one hour to obtain a solution containing the compound represented by the formula (I-1-c).

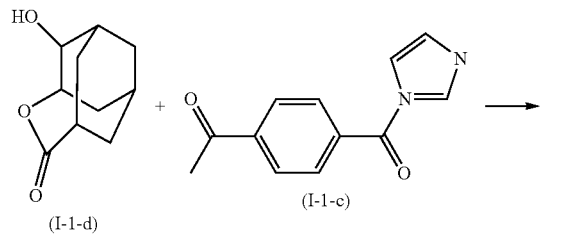

To the solution, 10.20 parts of the compound represented by the formula (I-1-d) was added and stirred at 23° C. for an hour, followed by being stirred at 70° C. for 18 hours.

To the reaction mixture, 200 parts of ethyl acetate and 100 parts of ion-exchanged water were added and then stirred, followed by conducting separation into an organic layer therefrom for washing.

This washing step was conducted five times.

Then the resultant mixture was concentrated, and the concentrates were separated by silica gel column chromatography [silica gel 60 to 200 mesh, produced by Merck, eluent: ethyl acetate] to obtain 12.84 parts of the compound represented by formula (I-1-e).

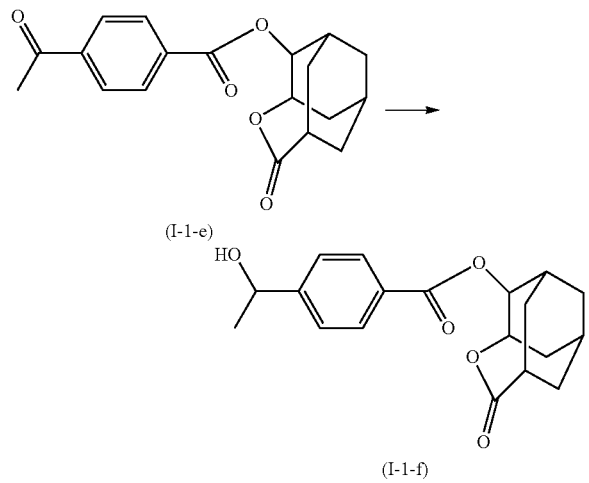

In a reactor, 60 parts of tetrahydrofuran was cooled to 5° C. and 1.59 parts of lithium aluminum hydride was added thereto. Then a mixture of 12.5 parts of the compound represented by the formula (I-1-e) and 40 parts of tetrahydrofuran was dropped thereinto at 0° C. over an hour, followed by being stirred at 23° C. for 12 hours. Then the mixture was stirred at 50° C. for 2 hours, followed by cooling to 5° C.

To the mixture, 24.54 parts of 10% sulfuric acid was dropped there into, and then 200 parts of chloroform and 100 parts of 5% aqueous sodium hydrogen carbonate solution were mixed and stirred, followed by conducting separation into an organic layer. To the organic layer, 100 parts of ion-exchanged water were added and then stirred at 23° C. for 30 minutes, followed by setting still to separate into an organic layer for washing. This washing step was conducted five times.

Then the resultant mixture was concentrated, and the concentrates were separated by silica gel column chromatography [silica gel 60 to 200 mesh, produced by Merck, eluent: ethyl acetate] to obtain 10.34 parts of the compound represented by formula (I-1-f).

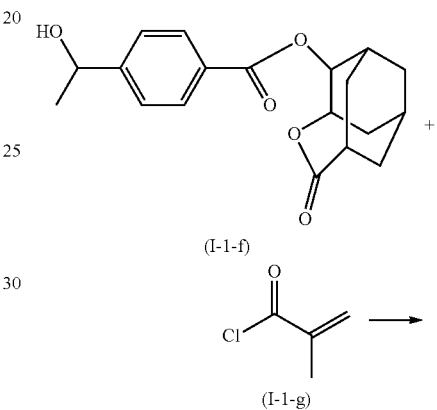

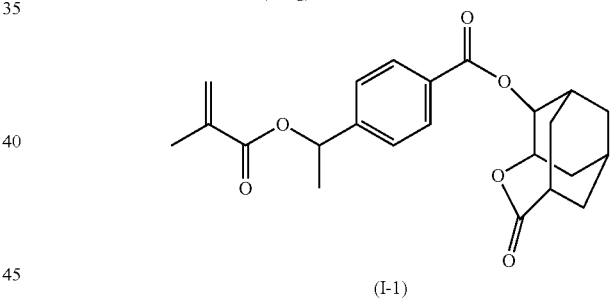

In a reactor, 2.03 parts of compound represented by formula (I-1-f) 1.83 parts of N-methylpyrrolidine and 20 parts of N-methylisobutylketone were mixed, and 0.77 parts of the compound represented by formula (I-1-g) was added thereto, followed by being stirred at 60° C. for 5 hours. Then to the reaction mixture 10 parts of ion-exchanged water were added and then stirred, followed by separating into an organic layer for washing. This washing step was conducted five times.

Then the resultant mixture was separated by silica gel column chromatography [silica gel 60 to 200 mesh, produced by Merck, eluent: ethyl acetate] to obtain 1.59 parts of the compound represented by formula (I-1).

MASS (MASS spectrum): 399.2 [M$^+$+H]

Example 2

The solution containing the compound represented by the formula (I-1-c) was prepared in the same manner as described in Example 1.

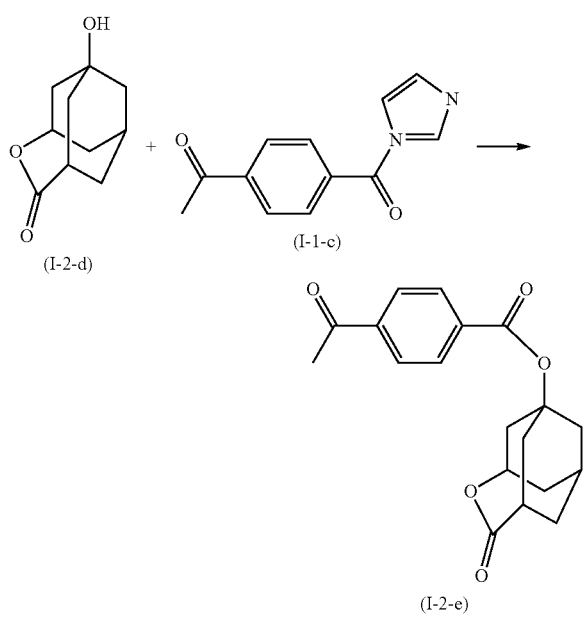

To the solution, 10.20 parts of the compound represented by the formula (I-2-d) was added and stirred at 23° C. for an hour, followed by being stirred at 70° C. for 18 hours.

To the reaction mixture, 200 parts of ethyl acetate and 100 parts of ion-exchanged water were added and then stirred, followed by conducting separation into an organic layer therefrom for washing.

This washing step was conducted five times.

Then the resultant mixture was concentrated, and the concentrates were separated by silica gel column chromatography [silica gel 60 to 200 mesh, produced by Merck, eluent: ethyl acetate] to obtain 12.66 parts of the compound represented by formula (I-2-e).

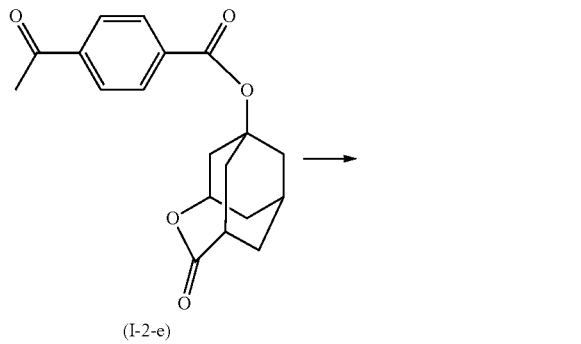

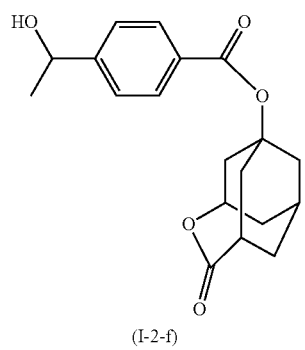

In a reactor, 60 parts of tetrahydrofuran was cooled to 5° C. and 1.59 parts of lithium aluminum hydride was added thereto. Then a mixture of 12.5 parts of the compound represented by the formula (I-1-e) and 40 parts of tetrahydrofuran was dropped thereinto at 5° C. over an hour, followed by being stirred at 23° C. for two hours. Then the mixture was stirred at 50° C. for 2 hours, followed by cooling to 5° C.

To the mixture, 24.54 parts of 10% sulfuric acid was dropped there into, and then 200 parts of chloroform and 100 parts of 5% aqueous sodium hydrogen carbonate solution were mixed and stirred, followed by conducting separation into an organic layer. To the organic layer, 100 parts of ion-exchanged water were added and then stirred at 23° C. for 30 minutes, followed by setting still to separate into an organic layer for washing. This washing step was conducted five times.

Then the resultant mixture was concentrated, and the concentrates were separated by silica gel column chromatography [silica gel 60 to 200 mesh, produced by Merck, eluent: ethyl acetate] to obtain 9.39 parts of the compound represented by formula (I-2-f).

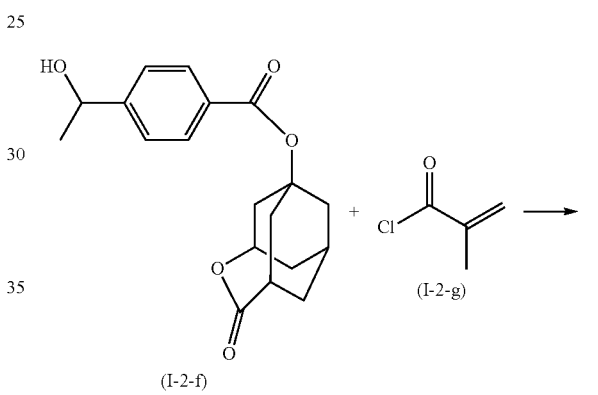

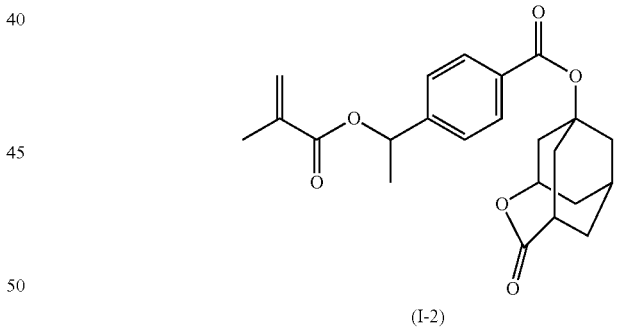

In a reactor, 2.03 parts of compound represented by formula (I-2-f) 1.83 parts of N-methylpyrrolidine and 20 parts of N-methylisobutylketone was mixed, and 0.77 parts of the compound represented by formula (I-2-g) was added thereto, followed by being stirred at 60° C. for 5 hours. Then to the reaction mixture 10 parts of ion-exchanged water were added and then stirred, followed by separating into an organic layer for washing. This washing step was conducted five times.

Then the resultant mixture was separated by silica gel column chromatography [silica gel 60 to 200 mesh, produced by Merck, eluent: ethyl acetate] to obtain 1.68 parts of the compound represented by formula (I-2).

MASS (MASS spectrum): 399.2 [M++H]

Example 3

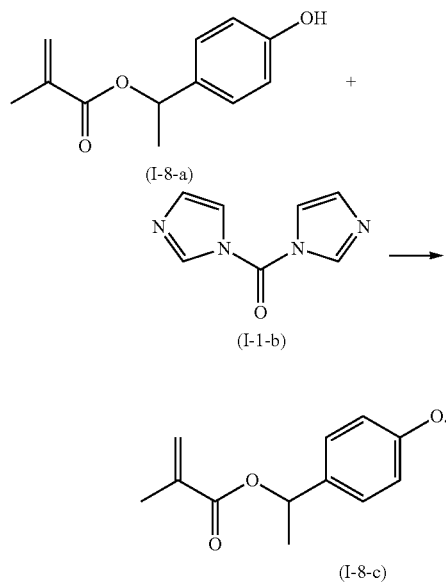

In a reactor, 11.45 parts of the compound represented by the formula (I-8-a) and 50 parts of acetonitrile were mixed and stirred at 40° C. for 30 minutes. To the obtained mixture, 10.79 parts of the compound represented by the formula (I-1-b) was added and then stirred at 60° C. for one hour to obtain a solution containing the compound represented by the formula (I-8-c).

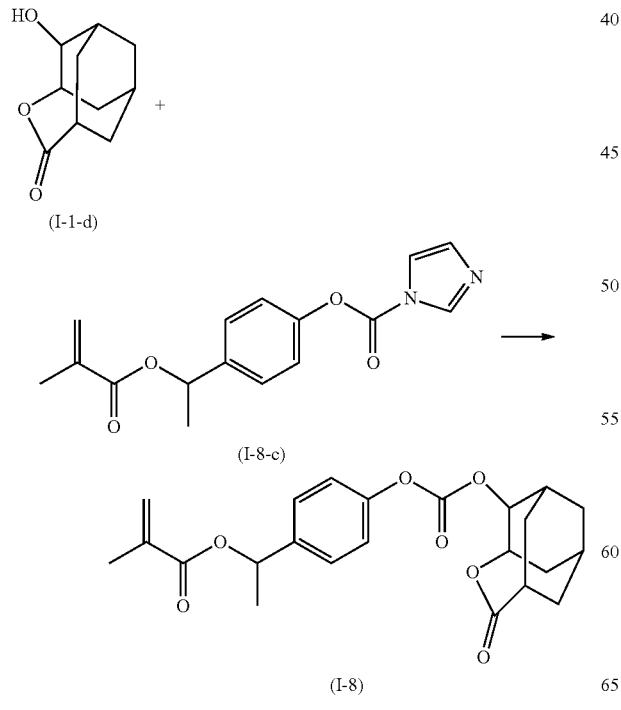

To the solution, 10.20 parts of the compound represented by the formula (I-1-d) was added and stirred at 23° C. for an hour, followed by being stirred at 60° C. for 3 hours.

To the reaction mixture, 200 parts of ethyl acetate and 100 parts of ion-exchanged water were added and then stirred, followed by conducting separation into an organic layer therefrom for washing.

This washing step was conducted five times.

Then the resultant mixture was concentrated, and the concentrates were separated by silica gel column chromatography [silica gel 60 to 200 mesh, produced by Merck, eluent: ethyl acetate] to obtain 10.19 parts of the compound represented by formula (I-8).

MASS (MASS spectrum): 415.2 [M++H]

Synthesis of Resin

Monomers used in the following Example are following monomers.

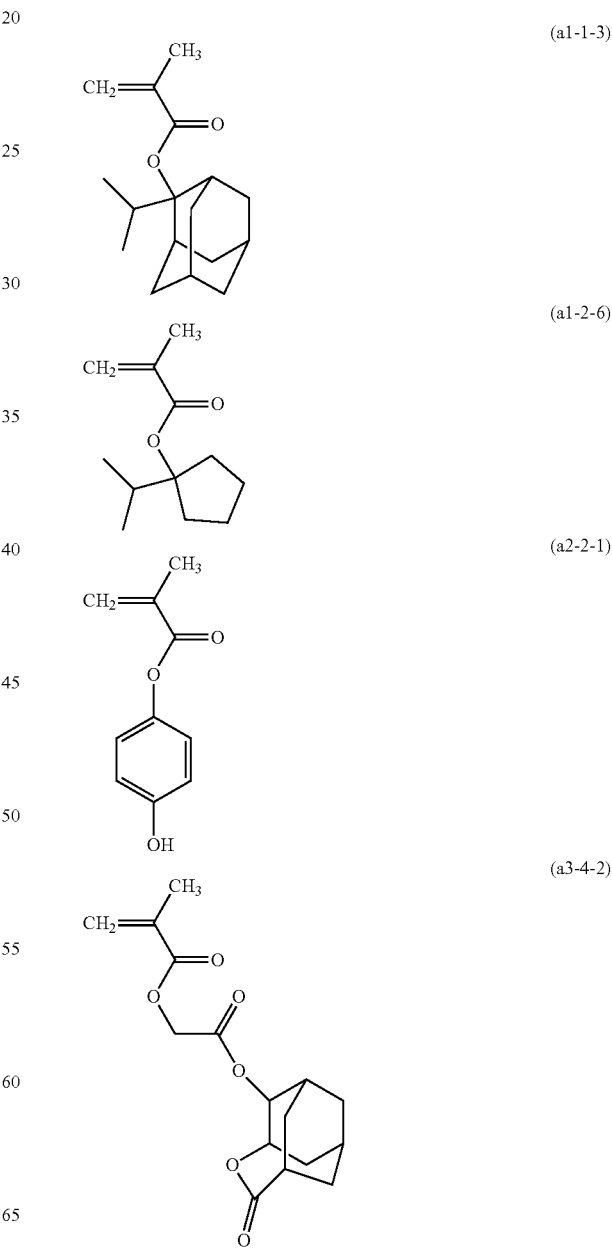

(I-1)

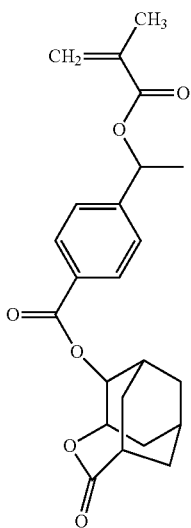

(I-2)

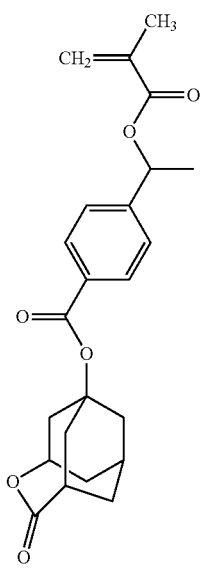

(I-8)

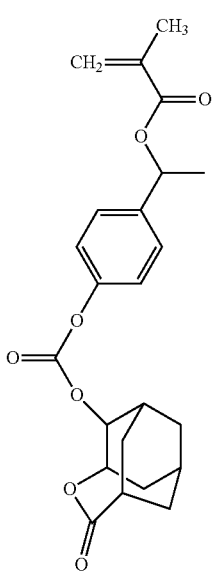

(IX-1)

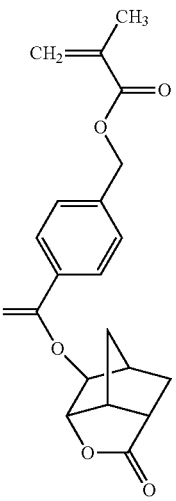

(IX-2)

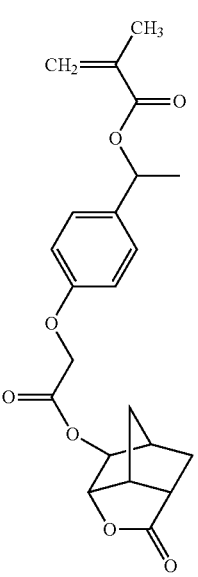

Those monomers are sometimes referred to as "Monomer (X)" in which (X) represents the sign of the formula corresponding to the monomer.

For example, the monomer represented by formula (a1-1-3) is referred to as "Monomer (a1-1-3)".

Example 4

The monomers (a2-2-1), (a1-1-3), (a1-2-6) and (I-1) were mixed in a molar ratio of 37/25/20/18 (monomer (a2-2-1)/monomer (a1-1-3)/monomer (a1-1-6)/monomer (I-1)), and methylisobutylketone was added in an amount of 1.5 times parts all the monomers to prepare a mixture. To the mixture, azobisisobutyronitrile as an initiator in a ratio of 1.2 mol % based on all monomer molar amount and azobis(2,4-dimethylvaleronitrile) as an initiator in a ratio of 3.6 mol % based on all monomer molar amount were added, and the obtained mixture was heated at 73° C. for about 5 hours.

Then to the reaction mixture, a large amount of n-heptane was added to precipitate a resin, followed by being filtrated to collect the resin. The resin had a weight-average molecular weight of about 6400, which was obtained in the yield of 64%. The polymer, which is referred to as Resin A1, had the following structural units.

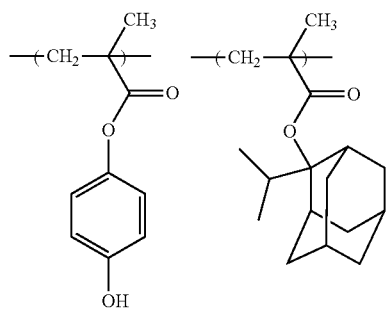
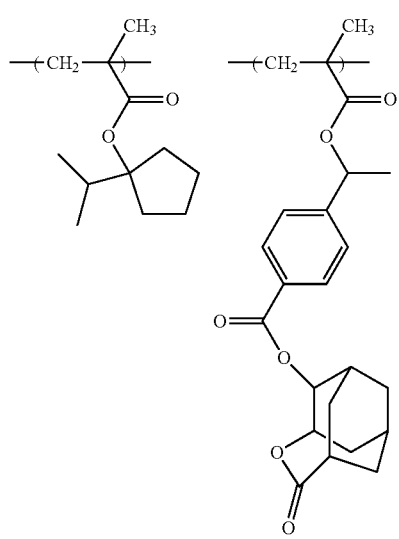

Example 5

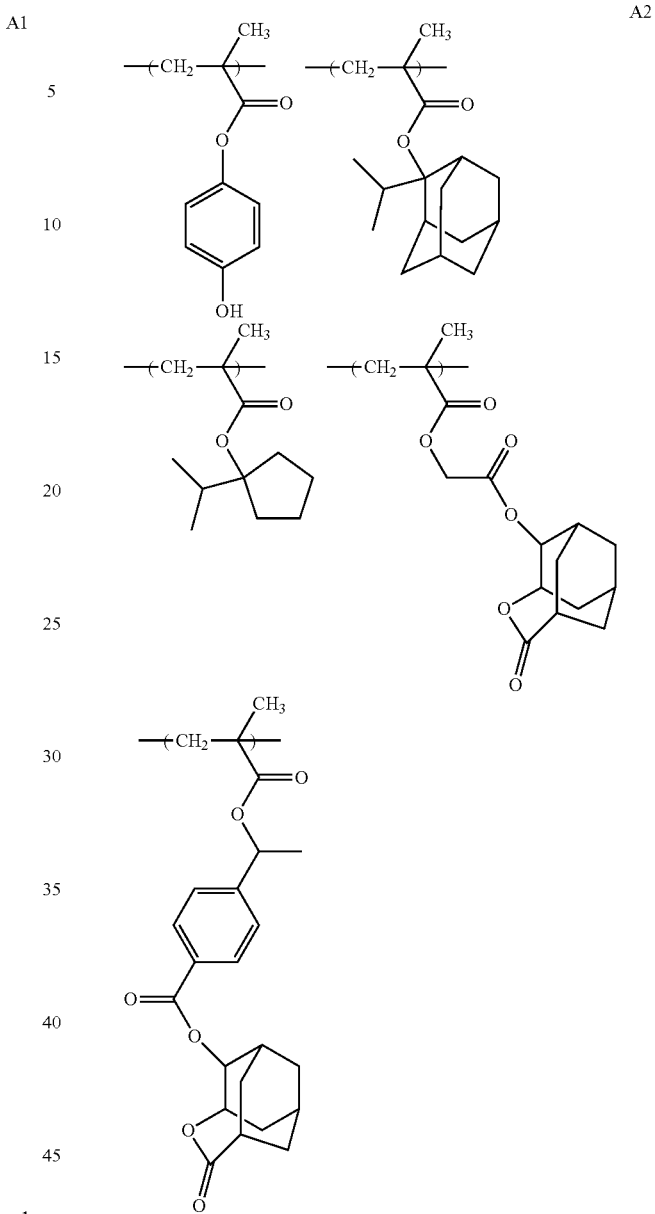

Example 6

The monomers (a2-2-1), (a1-1-3), (a1-2-6), (a3-4-2) and (I-1) were mixed in a molar ratio of 27/20/20/18/15 (monomer (a2-2-1)/monomer (a1-1-3)/monomer (a1-2-6)/monomer (a3-4-2)/monomer (I-1)), and methylisobutylketone was added in in an amount of 1.5 times parts all the monomers to prepare a mixture. To the mixture, azobisisobutyronitrile as an initiator in a ratio of 1.2 mol % based on all monomer molar amount and azobis(2,4-dimethylvaleronitrile) as an initiator in a ratio of 3.6 mol % based on all monomer molar amount were added, and the obtained mixture was heated at 73° C. for about 5 hours.

Then to the reaction mixture, a large amount of n-heptane was added to precipitate a resin, followed by being filtrated to collect the resin. The resin had a weight-average molecular weight of about 6400, which was obtained in the yield of 63%. The polymer, which is referred to as Resin A2, had the following structural units.

The monomers (a2-2-1), (a1-1-3), (a1-2-6) and (I-2) were mixed in a molar ratio of 37/25/20/18 (monomer (a2-2-1)/monomer (a1-1-3)/monomer (a1-2-6)/monomer (I-2)), and methylisobutylketone was added in in an amount of 1.5 times parts all the monomers to prepare a mixture. To the mixture, azobisisobutyronitrile as an initiator in a ratio of 1.2 mol % based on all monomer molar amount and azobis(2,4-dimethylvaleronitrile) as an initiator in a ratio of 3.6 mol % based on all monomer molar amount were added, and the obtained mixture was heated at 73° C. for about 5 hours.

Then to the reaction mixture, a large amount of n-heptane was added to precipitate a resin, followed by being filtrated to collect the resin. The resin had a weight-average molecular weight of about 6600, which was obtained in the yield of 62%. The polymer, which is referred to as Resin A3, had the following structural units.

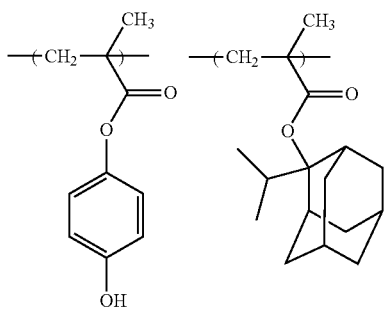

A3

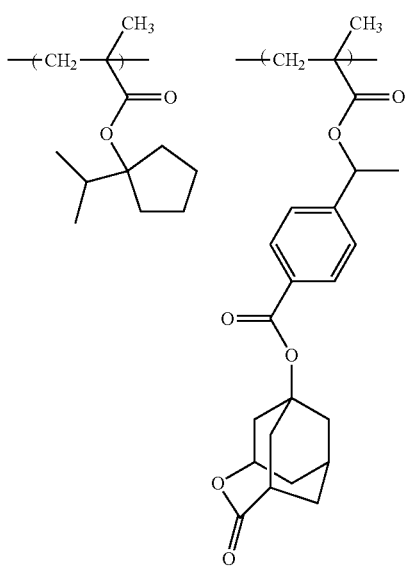

Example 7

The monomers (a2-2-1), (a1-1-3), (a1-2-6), (a3-4-2) and (I-2) were mixed in a molar ratio of 27/20/20/18/15 (monomer (a2-2-1)/monomer (a1-1-3)/monomer (a1-2-6)/monomer (a3-4-2)/monomer (I-2)), and methylisobutylketone was added in in an amount of 1.5 times parts all the monomers to prepare a mixture. To the mixture, azobisisobutyronitrile as an initiator in a ratio of 1.2 mol % based on all monomer molar amount and azobis(2,4-dimethylvaleronitrile) as an initiator in a ratio of 3.6 mol % based on all monomer molar amount were added, and the obtained mixture was heated at 73° C. for about 5 hours.

Then to the reaction mixture, a large amount of n-heptane was added to precipitate a resin, followed by being filtrated to collect the resin. The resin had a weight-average molecular weight of about 6700, which was obtained in the yield of 60%. The polymer, which is referred to as Resin A4, had the following structural units.

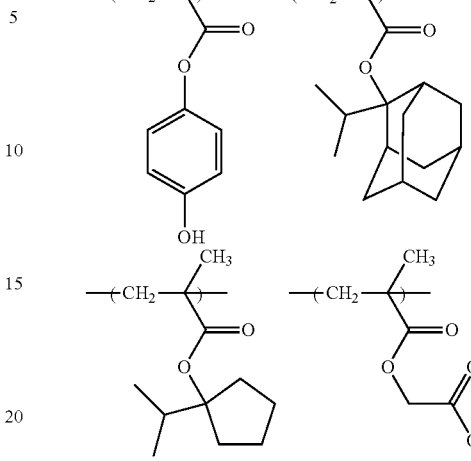

A4

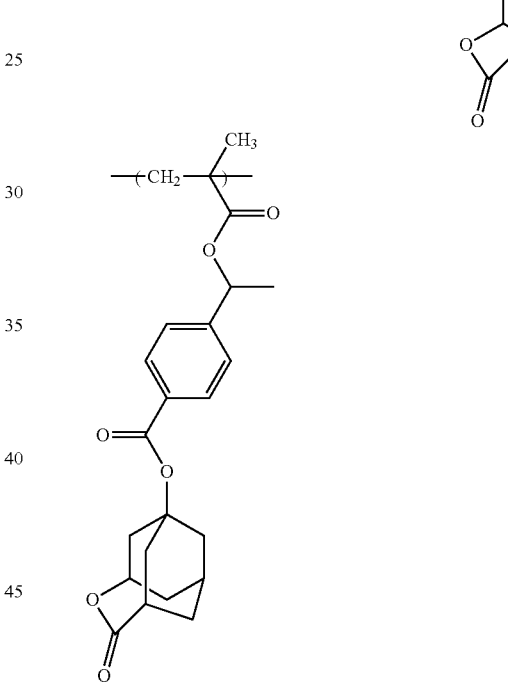

Example 8

The monomers (a2-2-1), (a1-1-3), (a1-2-6) and (I-8) were mixed in a molar ratio of 37/25/20/18 (monomer (a2-2-1)/monomer (a1-1-3)/monomer (a1-2-6)/monomer (I-8)), and methylisobutylketone was added in in an amount of 1.5 times parts all the monomers to prepare a mixture. To the mixture, azobisisobutyronitrile as an initiator in a ratio of 1.2 mol % based on all monomer molar amount and azobis(2,4-dimethylvaleronitrile) as an initiator in a ratio of 3.6 mol % based on all monomer molar amount were added, and the obtained mixture was heated at 73° C. for about 5 hours.

Then to the reaction mixture, a large amount of n-heptane was added to precipitate a resin, followed by being filtrated to collect the resin. The resin had a weight-average molecular weight of about 6200, which was obtained in the yield of 58%. The polymer, which is referred to as Resin A5, had the following structural units.

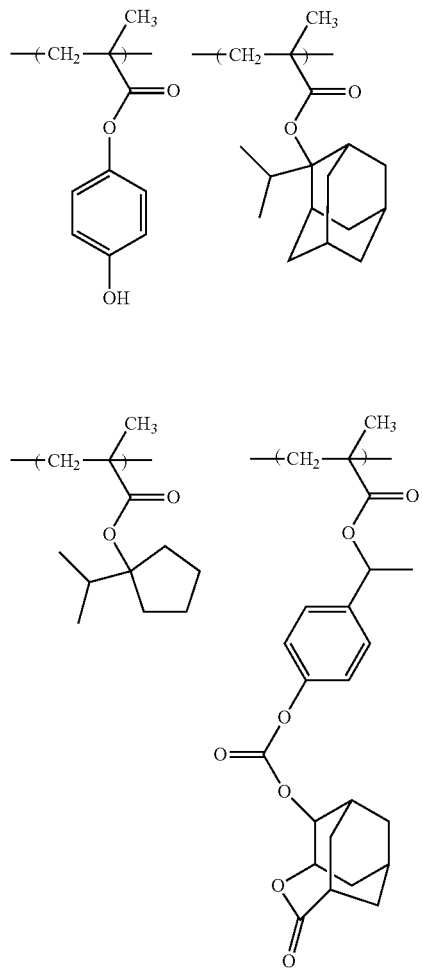

A5

Example 9

The monomers (a2-2-1), (a1-1-3), (a1-2-6), (a3-4-2) and (I-8) were mixed in a molar ratio of 27/20/20/18/15 (monomer (a2-2-1)/monomer (a1-1-3)/monomer (a1-2-6)/monomer (a3-4-2)/monomer (I-8)), and methylisobutylketone was added in in an amount of 1.5 times parts all the monomers to prepare a mixture. To the mixture, azobisisobutyronitrile as an initiator in a ratio of 1.2 mol % based on all monomer molar amount and azobis(2,4-dimethylvaleronitrile) as an initiator in a ratio of 3.6 mol % based on all monomer molar amount were added, and the obtained mixture was heated at 73° C. for about 5 hours.

Then to the reaction mixture, a large amount of n-heptane was added to precipitate a resin, followed by being filtrated to collect the resin. The resin had a weight-average molecular weight of about 6000, which was obtained in the yield of 59%. The polymer, which is referred to as Resin A6, had the following structural units.

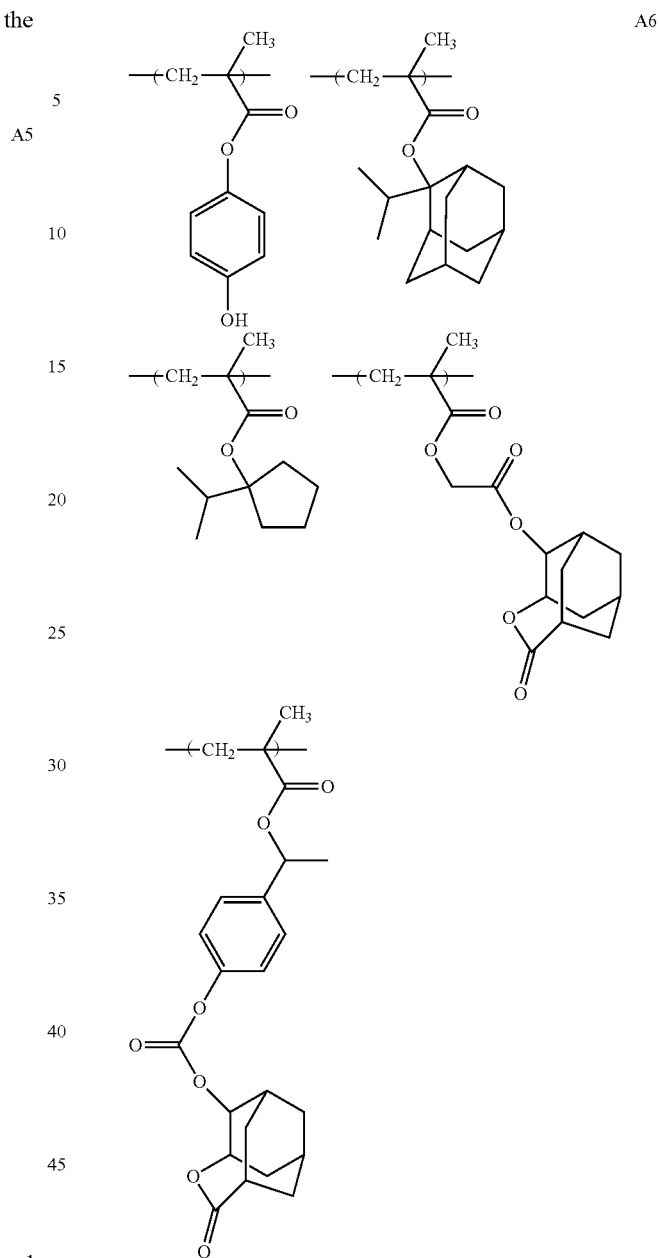

A6

Synthesis Example 1

The monomers (a2-2-1), (a1-1-3), (a1-2-6) and (IX-1) were mixed in a molar ratio of 37/25/20/18 (monomer (a2-2-1)/monomer (a1-1-3)/monomer (a1-2-6)/monomer (IX-1)), and methylisobutylketone was added in in an amount of 1.5 times parts all the monomers to prepare a mixture. To the mixture, azobisisobutyronitrile as an initiator in a ratio of 1.2 mol % based on all monomer molar amount and azobis(2,4-dimethylvaleronitrile) as an initiator in a ratio of 3.6 mol % based on all monomer molar amount were added, and the obtained mixture was heated at 73° C. for about 5 hours.

Then to the reaction mixture, a large amount of n-heptane was added to precipitate a resin, followed by being filtrated to collect the resin. The resin had a weight-average molecular weight of about 6500, which was obtained in the yield of 60%. The polymer, which is referred to as Resin AX1, had the following structural units.

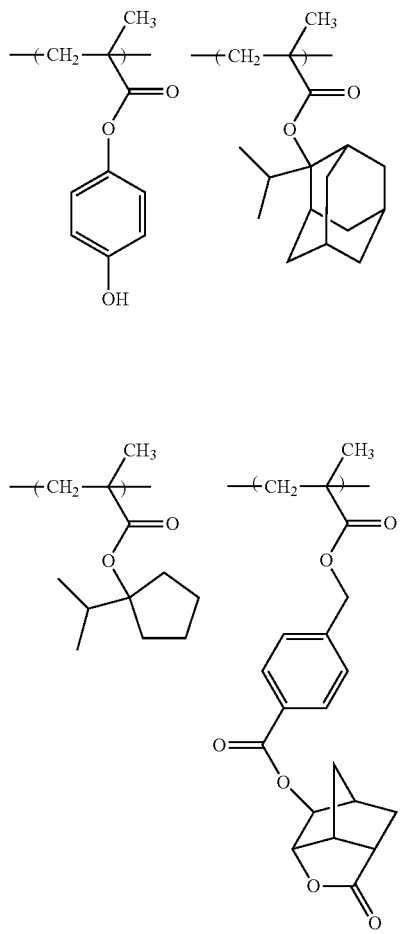

AX1

Synthesis Example 2

The monomers (a2-2-1), (a1-1-3), (a1-2-6) and (IX-2) were mixed in a molar ratio of 37/25/20/18 (monomer (a2-2-1)/monomer (a1-1-3)/monomer (a1-2-6)/monomer (IX-2)), and methylisobutylketone was added in in an amount of 1.5 times parts all the monomers to prepare a mixture. To the mixture, azobisisobutyronitrile as an initiator in a ratio of 1.2 mol % based on all monomer molar amount and azobis(2,4-dimethylvaleronitrile) as an initiator in a ratio of 3.6 mol % based on all monomer molar amount were added, and the obtained mixture was heated at 73° C. for about 5 hours.

Then to the reaction mixture, a large amount of n-heptane was added to precipitate a resin, followed by being filtrated to collect the resin. The resin had a weight-average molecular weight of about 6400, which was obtained in the yield of 66%. The polymer, which is referred to as Resin AX2, had the following structural units.

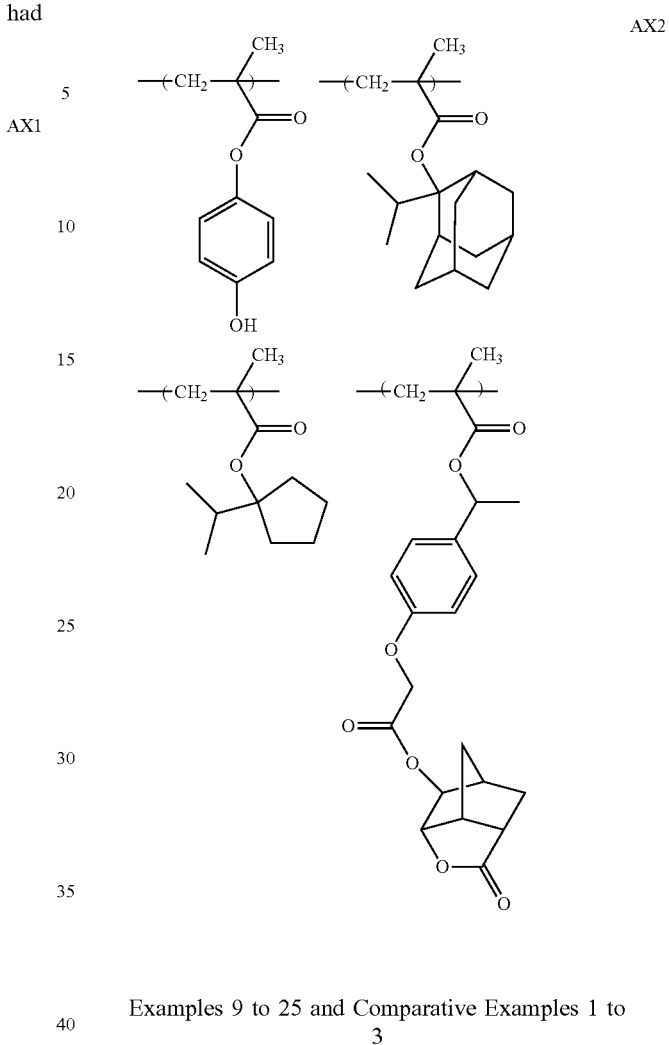

AX2

Examples 9 to 25 and Comparative Examples 1 to 3

<Producing Photoresist Compositions>

The following components as listed in the following table were mixed and dissolved in the solvent as mentioned below, and then filtrated through a fluorine resin filter having pore diameter of 0.2 μm, to prepare photoresist compositions.

TABLE 1

| Comp. No. | Resin (kind/amount (part)) | Acid generator (kind/amount (part)) | Quencher (kind/amount (part)) | PB(° C.)/ PEB (° C.) |
|---|---|---|---|---|
| 1 | A1/10 | B1-43/3.4 | D1/0.7 | 110/120 |
| 2 | A2/10 | B1-43/3.4 | D1/0.7 | 110/120 |
| 3 | A1/10 | B1-43/3.4 | D2/0.7 | 110/120 |
| 4 | A1/10 | B1-43/3.4 | C1/0.7 | 110/120 |
| 5 | A3/10 | B1-43/3.4 | D1/0.7 | 110/120 |
| 6 | A4/10 | B1-43/3.4 | D1/0.7 | 110/120 |
| 7 | A5/10 | B1-43/3.4 | D1/0.7 | 110/120 |
| 8 | A6/10 | B1-43/3.4 | D1/0.7 | 110/120 |
| Compar. comp 1 | AX1/10 | B1-43/3.4 | C1/0.7 | 110/120 |
| Compar. comp 2 | AX2/10 | B1-43/3.4 | C1/0.7 | 110/120 |

In Table 1, each of characters represents the following component:

<Resin>

A1: Resin A1, A2: Resin A2, A3: Resin A3, A4: Resin A4, A5: Resin A5, A6: Resin A6, AX1: Resin AX1, AX2: Resin AX2

<Acid Generator>

B1-43: Salt represented by formula (B1-43), produced according to the method as recited in JP2016-47815A1

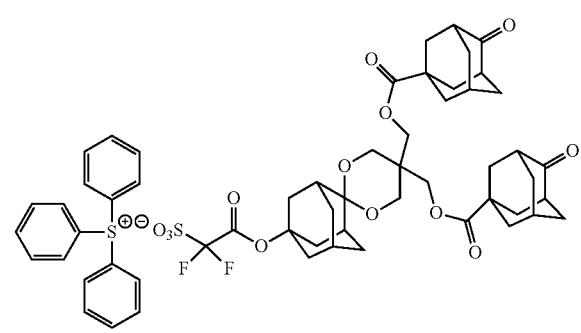

<Quencher>

D1: The compound of the following formula, produced according to the method as recited in JP2011-39502A1

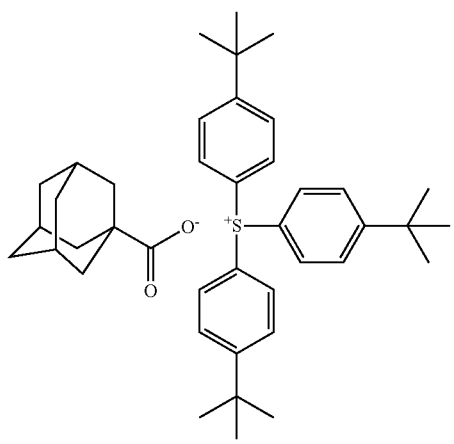 [SMILES: O=C([O-])C12CC3CC(CC(C3)C1)C2 ; CC(C)(C)c1ccc([S+](c2ccc(C(C)(C)C)cc2)c2ccc(C(C)(C)C)cc2)cc1]

D2: The compound of the following formula, produced by Tokyo Chemical Industries, Co, Ltd.

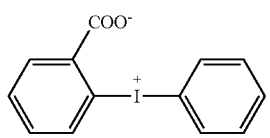

C1: The compound of the following formula, produced by Tokyo Chemical Industries, Co, Ltd.

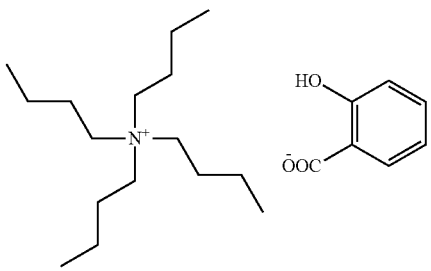

<Solvent>

Mixture of the Following Solvents

| | |
|---|---|
| propyleneglycolmonomethylether acetate | 400 parts |
| propyleneglycolmonomethylether | 150 parts |
| γ-butyrolactone | 5 parts |

<Evaluation: Alkali Development>

6 inch-diameter silicon wafers were each coated with hexamethyldisilazane and then baked at 90° C. for 60 seconds using a direct hotplate.

Each of the photoresist compositions prepared as above was spin-coated over the coating so that the thickness of the resulting film became 40 nm after drying. The silicon wafers thus coated with the respective photoresist compositions were each prebaked on a direct hotplate at the temperature as listed in the column "PB" of Table 1 for 60 seconds. Using an EB straight-writing system (HL-800D 50 keV manufactured by HITACH), line-and-space patterns were produced on the composition layer with the exposure quantity being varied stepwise.

After the exposure, each wafer was subjected to post-exposure baking on a hotplate at the temperature as listed in the column "PEB" of Table 1 for 60 seconds and then to development for 60 seconds at 23° C. with 2.38% by mass aqueous tetrametylammonium hydroxide solution in the manner of paddle development to produce positive photoresist patterns.

Effective sensitivity (ES) was defined as the exposure quantity with which exposure provides a pattern with 60 nm of the line width and 60 nm of space width after development, the pattern being observed with a scanning electron microscope.

Determining Line Edge Roughness:

The line-and-space patterns were produced according to the above-mentioned procedure in which the exposure step was conducted at the effective sensitivity.

The wall surface of the photoresist pattern was observed using a scanning electron microscope, and the irregularity in wall surface was determined. Here, the roughness width means the difference of the largest value and the smallest value as to the wall width.

Table 2 illustrates the results thereof.

TABLE 2

| Ex. No. | Composition No. | LER value (nm) |
|---|---|---|
| Ex. 10 | 1 | 3.38 |
| Ex. 11 | 2 | 3.48 |
| Ex. 12 | 3 | 3.39 |
| Ex. 13 | 4 | 3.76 |
| Ex. 14 | 5 | 3.42 |
| Ex. 15 | 6 | 3.49 |

TABLE 2-continued

| Ex. No. | Composition No. | LER value (nm) |
|---|---|---|
| Ex. 16 | 7 | 3.39 |
| Ex. 17 | 8 | 3.46 |
| Comp. Ex. 1 | Compar. Comp. 1 | 4.38 |
| Comp. Ex. 2 | Compar. Comp. 2 | 3.95 |

<Evaluation: Development Using Butyl Acetate>

6 inch-diameter Silicon wafers were each coated with hexamethyldisilazane and then baked at 90° C. for 60 seconds using a direct hotplate.

Each of the photoresist compositions prepared as above was spin-coated over the coating so that the thickness of the resulting film became 40 nm after drying. The silicon wafers thus coated with the respective photoresist compositions were each prebaked on a direct hotplate at the temperature as listed in the column "PB" of Table 1 for 60 seconds. Using an EB straight-writing system (HL-800D 50 keV manufactured by HITACH), line-and-space patterns were produced on the composition layer with the exposure quantity being varied stepwise.

After the exposure, each wafer was subjected to post-exposure baking on a hotplate at the temperature as listed in the column "PEB" of Table 1 for 60 seconds and then to development for 20 seconds at 23° C. with butyl acetate in the manner of dynamic dispense method to produce negative photoresist patterns.

Line edge roughness of the negative photoresist patterns was determined in the same manner as that of the positive photoresist patterns except that patterns were developed using the above-mentioned organic solvent.

Table 3 illustrates the results thereof.

TABLE 3

| Ex. No. | Composition No. | LER value (nm) |
|---|---|---|
| Ex. 18 | 1 | 3.32 |
| Ex. 19 | 2 | 3.22 |
| Ex. 20 | 3 | 3.33 |
| Ex. 21 | 4 | 3.74 |
| Ex. 22 | 5 | 3.38 |
| Ex. 23 | 6 | 3.25 |
| Ex. 24 | 7 | 3.33 |
| Ex. 25 | 8 | 3.24 |
| Comp. Ex. 3 | Compar. Comp. 1 | 4.28 |

The composition of the present invention can provide photoresist patterns with smaller LER, and is suitable for fine processing of semiconductors.

What is claimed is:
1. A compound represented by the formula (I):

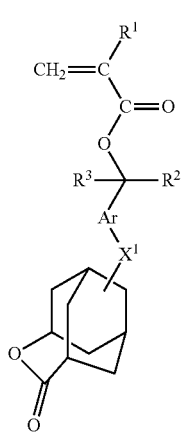

(I)

wherein $R^1$ represents a hydrogen atom or a methyl group,
$R^2$ represents a C1-C6 saturated hydrocarbon group,
$R^3$ represents a hydrogen atom or a C1-C6 saturated hydrocarbon group,
Ar represents a C6-C36 aromatic hydrocarbon group in which a hydrogen atom can be replaced by a substituent, and
$X^1$ represents a divalent group which has —CO—O—, —O—CO—, —O—CO—O— or —O—.

2. The compound according to claim 1 wherein $R^3$ represents a hydrogen atom.

3. The compound according to claim 2 wherein $R^2$ represents a C1-C6 alkyl group.

4. The compound according to claim 1 wherein $X^1$ represents *—$X^{11}$-$A^{11}$-$X^{12}$— or —$X^{18}$— where $A^{11}$ represents a C1-C6 alkanediyl group, $X^{11}$, $X^{12}$ and $X^{18}$ each independently represents —CO—O—, —O—CO—, —O—CO—O— or —O—, and * represents a binding position to Ar.

5. A resin comprising a structural unit derived from the compound according to claim 1.

6. The resin according to claim 5, further comprising a structural unit which comprises an acid-labile group and being different from the structural unit derived from the compound represented by the formula (I).

7. A photoresist composition comprising the resin according to claim 5 and an acid generator.

8. The photoresist composition according to claim 7 wherein an acid generator comprises a salt represented by the formula (B1):

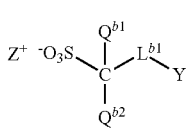

(B1)

in which $Q^{b1}$ and $Q^{b2}$ independently each represent a fluorine atom or a C1-C6 perfluoroalkyl group,
$L^{b1}$ represents a C1-C24 divalent saturated hydrocarbon group in which a methylene group can be replaced by —O— or —CO— and in which a hydrogen atom can be replaced by a fluorine atom or a hydroxyl group,
Y represents a methyl group in which a hydrogen atom can be replaced by a substituent or a C3-C18 alicyclic hydrocarbon group in which a hydrogen atom can be replaced by a substituent and in which a methylene group has been replaced by —O—, —S(O)$_2$— or —CO—, and Z$^+$ represents an organic cation.

9. The photoresist composition according to claim 7 which further comprises a salt generating an acid weaker in acidity than an acid generated from the acid generator.

10. The photoresist composition according to claim 7 which further comprises another resin, said another resin comprising a structural unit which has a fluorine atom.

11. A process for producing a photoresist pattern comprising the following steps (1) to (5):
  (1) a step of applying the photoresist composition according to claim 7 on a substrate,
  (2) a step of forming a composition film by conducting drying,
  (3) a step of exposing the composition film to radiation,
  (4) a step of baking the exposed composition film, and
  (5) a step of developing the baked composition film thereby forming a photoresist pattern.

\* \* \* \* \*